US012807691B2

(12) United States Patent
Li et al.

(10) Patent No.: US 12,807,691 B2
(45) Date of Patent: Nov. 24, 2026

(54) ANTIBODIES SPECIFICALLY RECOGNIZING NERVE GROWTH FACTOR AND USES THEREOF

(71) Applicant: STAIDSON (BEIJING) BIOPHARMACEUTICALS CO., LTD., Beijing (CN)

(72) Inventors: Cui Li, Beijing (CN); Li Yan, Beijing (CN); Qun Huang, Beijing (CN)

(73) Assignee: Staidson (Beijing) BioPharmaceuticals Co., Ltd, Beijing (CN)

( * ) Notice: Subject to any disclaimer, the term of this patent is extended or adjusted under 35 U.S.C. 154(b) by 951 days.

(21) Appl. No.: 17/928,136

(22) PCT Filed: May 25, 2021

(86) PCT No.: PCT/CN2021/095649

§ 371 (c)(1),
(2) Date: Nov. 28, 2022

(87) PCT Pub. No.: WO2021/238886

PCT Pub. Date: Dec. 2, 2021

(65) Prior Publication Data

US 2023/0220057 A1 Jul. 13, 2023

Related U.S. Application Data

(63) Continuation of application No. PCT/CN2020/092574, filed on May 27, 2020.

(30) Foreign Application Priority Data

May 27, 2020 (WO) ................ PCT/CN2020/092574

(51) Int. Cl.
*A61K 39/395* (2006.01)
*A61P 23/00* (2006.01)
(Continued)

(52) U.S. Cl.
CPC ............. *C07K 16/22* (2013.01); *A61P 23/00* (2018.01); *A61P 29/00* (2018.01);
(Continued)

(58) Field of Classification Search
None
See application file for complete search history.

(56) References Cited

U.S. PATENT DOCUMENTS

2010/0034818 A1 2/2010 Wild, Jr. et al.
2013/0336975 A1 12/2013 Dutzar
2019/0276548 A1 9/2019 Steiniger et al.

FOREIGN PATENT DOCUMENTS

CN 1849138 A 10/2006
CN 101633694 A 1/2010
(Continued)

OTHER PUBLICATIONS

Denk et al., Nerve Growth Factor and Pain Mechanisms, Ann Rev. Neurosci. 40:307-325, 2017.*
(Continued)

*Primary Examiner* — Claire Kaufman
(74) *Attorney, Agent, or Firm* — WOOD, PHILLIPS, KATZ, CLARK & MORTIMER

(57) ABSTRACT

The present application provides antibodies including antigen-binding fragment thereof that specifically recognizes Nerve Growth Factor (NGF). Also provided are methods of making and using these antibodies.

10 Claims, 9 Drawing Sheets

Specification includes a Sequence Listing.

(51) Int. Cl.

| | |
|---|---|
| ***A61P 29/00*** | (2006.01) |
| ***C07K 16/22*** | (2006.01) |
| *A61K 39/00* | (2006.01) |

(52) U.S. Cl.

CPC .... *A61K 2039/505* (2013.01); *C07K 2317/24* (2013.01); *C07K 2317/33* (2013.01); *C07K 2317/565* (2013.01); *C07K 2317/73* (2013.01); *C07K 2317/92* (2013.01)

(56) References Cited

FOREIGN PATENT DOCUMENTS

| | | | |
|---|---|---|---|
| CN | 101827609 | A | 9/2010 |
| CN | 104774265 | A | 7/2015 |
| CN | 105273087 | A | 1/2016 |
| CN | 108059676 | A | 5/2018 |
| CN | 108623687 | A | 10/2018 |
| CN | 109553683 | A | 4/2019 |
| WO | 2009023540 | A1 | 2/2009 |
| WO | 2019201133 | A1 | 10/2019 |

OTHER PUBLICATIONS

Jaffal et al., Targeting nerve growth factor for pain relief: pros and cons, Korean J. Pain, 37(4):288-298, 2024.*

Song, Mo et al. 2010. "Expressions of nerve growth factor and its receptor in breast canoer and its clinical significance." Journal of Dalian Medical University. vol. 32, Issue 02, English abstract.

International Search Report and Written Opinion issued in counterpart PCT Application No. PCT/CN2021/095649 dated Aug. 23, 2021 (fourteen (14) pages).

Xu, L., et al. "The anti-NGF antibody muMab 911 both prevents and reverses pain behaviour and subchondral osteoclast numbers in a rat model of osteoarthritis pain" Osteoarthritis and Cartilage, vol. 24, No. 9, May 18, 2016 (May 18, 2016), pp. 1587-1595.

Smith, S.A., et al. "Accession No. QAV56087" Genbank, Feb. 3, 2019 (Feb. 3, 2019), Origin.

* cited by examiner

ANTIBODIES SPECIFICALLY RECOGNIZING NERVE GROWTH FACTOR AND USES THEREOF

CROSS REFERENCE TO RELATED APPLICATIONS

This is a national stage application filed under 37 U.S.C. 371 based on International Patent Application No. PCT/CN2021/095649, filed May 25, 2021, which claims priority to International Patent Application No. PCT/CN2020/092574, filed May 27, 2020, the disclosures of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 061802-00009_Corrected_Sequence_Listing.txt, date recorded: Apr. 22, 2020, size: 33598 Bytes).

FIELD OF THE APPLICATION

This application pertains to antibodies that specifically recognize nerve growth factor, and methods of manufacture and uses thereof, including methods of treating nerve growth factor related disorders.

BACKGROUND OF THE APPLICATION

Nerve growth factor (NGF) was first recognized as a protein that has the function of promoting neuronal growth in developing chick embryos (Bueker 1948). It has been known that NGF belongs to the neurotrophin (NT) family, a group of structurally related proteins, including brain-derived neurotrophic factor (BDNF), neurotrophin-3 (NT-3), and neurotrophin-4/5 (NT-4/5). They are all secreted proteins essential for the proper development, patterning, and maintenance of the peripheral nervous system. All the neurotrophins share a common receptor, p75, while each NT is specific for a different Trk receptor subtype (A, B, and C) (Huang and Reichardt, 2003; Kalb, 2005). NGF binds the receptors of p75 and TrkA.

In healthy human, injection of NGF subcutaneously can cause pain of the local site and hyperalgesia within minutes (Petty et al. 1994). NGF given systematically even in low dose could result in myalgia. These suggest the NGF's activating or sensitizing effect on nociceptors. In transgenic mice, over-expression of NGF in vivo driven by a glial protein promoter can result in enhanced neuropathic pain behavior and sprouting of neurons after the chronic constriction injury, demonstrating a connection between NGF and neuropathic pain and sympathetic sprouting in the dorsal root ganglia (DRG). NGF promotes the sprouting of sympathetic neurons and the formation of aberrant innervation of nociceptive neurons, which is thought to contribute to the induction and maintenance of chronic nociceptive/pain states. (Ramer et al., 1998, 1999). In preclinical, NGF levels in local issue are found to be elevated in CFA- and carrageenan-injected animals (Ma et al, 2000). The NGF released from tissue injury and its subsequent action in the periphery is believed to plays a major role in the induction of thermal hyperalgesia. This process is referred as 'peripheral sensitization' (Mendell et al, 2002). NGF binds its high affinity receptor TrkA and, after internalization and retrograde transport to nociceptor cell bodies in the DRG, initiates secretion of nociceptive neuropeptides (e.g., substance P, CGRP) and PKC activation in the dorsal horn of the spinal cord (Sah et al., 2003). This is a process related as 'central sensitization'. Neutralization of NGF binding to its receptor is therefore a therapeutic approach to treating diseases and conditions mediated through NGF. Anti-NGF antibody is therefore a method of treating a condition caused by increased expression of NGF or sensitivity to NGF. The antibodies against NGF, Tanezumab (Pfizer) was described in U.S. Pat. No. 7,449,616 and Fulranumab (Amgen) in PCT Publication No. WO 2005/019266.

The disclosures of all publications, patents, patent applications and published patent applications referred to herein are hereby incorporated herein by reference in their entirety.

BRIEF SUMMARY OF THE APPLICATION

The present application provides an isolated anti-NGF antibody that specifically binds to NGF, and methods of use thereof for treating NGF related disorders.

In some embodiments according to any one of the isolated anti-NGF antibodies described above, the isolated anti-NGF antibody comprises: a heavy chain variable domain ($V_H$) comprising a heavy chain complementarity determining region (HC-CDR) 1 comprising TYWIS (SEQ ID NO: 1); an HC-CDR2 comprising AIDPSDSDARYSPSFQG (SEQ ID NO: 2); and an HC-CDR3 comprising SDPGYSGYSLLYGFDS (SEQ ID NO: 3) or a variant thereof comprising up to about 5 amino acid substitutions in the HC-CDRs; and a light chain variable domain ($V_L$) comprising a light chain complementarity determining region (LC-CDR) 1 comprising RSSQSLVQRNX$_1$NTYLS (SEQ ID NO: 30), wherein X$_1$ can be any amino acid; a LC-CDR2 comprising QVSNRYS (SEQ ID NO: 5); and a LC-CDR3 comprising GQGAHLPLT (SEQ ID NO: 6) or a variant thereof comprising up to about 5 amino acid substitutions in the LC-CDRs.

In some embodiments according to any one of the isolated anti-NGF antibodies described above, the isolated anti-NGF antibody comprises: a heavy chain variable domain ($V_H$) comprising a heavy chain complementarity determining region (HC-CDR) 1 comprising TYWIS (SEQ ID NO: 1); an HC-CDR2 comprising AIDPSDSDARYSPSFQG (SEQ ID NO: 2); and an HC-CDR3 comprising SDPGYSGYSLLYGFDS (SEQ ID NO: 3) or a variant thereof comprising up to about 5 amino acid substitutions in the HC-CDRs; and a light chain variable domain ($V_L$) comprising a light chain complementarity determining region (LC-CDR) 1 comprising RSSQSLVQRNX$_1$NTYLS (SEQ ID NO: 39), wherein X$_1$ is G, A, S, or T; a LC-CDR2 comprising QVSNRYS (SEQ ID NO: 5); and a LC-CDR3 comprising GQGAHLPLT (SEQ ID NO: 6) or a variant thereof comprising up to about 5 amino acid substitutions in the LC-CDRs.

In some embodiments according to any one of the isolated anti-NGF antibodies described above, the isolated anti-NGF antibody comprises: a heavy chain variable domain ($V_H$) comprising a heavy chain complementarity determining region (HC-CDR) 1 comprising TYWIS (SEQ ID NO: 1); an HC-CDR2 comprising AIDPSDSDARYSPSFQG (SEQ ID NO: 2); and an HC-CDR3 comprising SDPGYSGYSLLYGFDS (SEQ ID NO: 3) or a variant thereof comprising up to about 5 amino acid substitutions in the HC-CDRs; and a light chain variable domain ($V_L$) comprising a light chain complementarity determining region (LC-CDR) 1 comprising RSSQSLVQRNGNTYLS (SEQ ID NO: 4) or RSSQSLVQRNANTYLS (SEQ ID NO: 7); a LC-CDR2 comprising QVSNRYS (SEQ ID NO: 5); and a LC-CDR3 comprising GQGAHLPLT (SEQ ID NO: 6) or a variant thereof comprising up to about 5 amino acid substitutions in the LC-CDRs.

In some embodiments, there is provided an isolated anti-NGF antibody, comprising a $V_H$ comprising an HC-CDR1, an HC-CDR2, and an HC-CDR3 of a $V_H$ comprising the amino acid sequence of any one of SEQ ID NOs: 8-13; and a $V_L$ comprising a LC-CDR1, a LC-CDR2, and a LC-CDR3 of a $V_L$ comprising the amino acid sequence of any one of SEQ ID NOs: 14-24.

In some embodiments, there is provided an isolated anti-NGF antibody that binds to the human nerve growth factor with a Kd from about 0.1 μM to about 1 nM.

In some embodiments, there is provided an isolated anti-NGF antibody, comprising a $V_H$ comprising the amino acid sequence of any one of SEQ ID NOs: 8-13, or a variant thereof having at least about 90% sequence identity to the amino acid sequence of any one of SEQ ID NOs: 8-13; and a $V_L$ comprising the amino acid sequence of any one of SEQ ID NOs: 14-24, or a variant thereof having at least about 90% sequence identity to the amino acid sequence of any one of SEQ ID NOs: 14-24.

In some embodiments, according to any one of the isolated anti-NGF antibodies described above, the isolated anti-NGF antibody comprises: (i) a $V_H$ comprising the amino acid sequence of SEQ ID NO: 8; and a $V_L$ comprising the amino acid sequence of SEQ ID NO: 17; (ii) a $V_H$ comprising the amino acid sequence of SEQ ID NO: 8; and a $V_L$ comprising the amino acid sequence of SEQ ID NO: 19; (iii) a $V_H$ comprising the amino acid sequence of SEQ ID NO: 8; and a $V_L$ comprising the amino acid sequence of SEQ ID NO: 23; (iv) a $V_H$ comprising the amino acid sequence of SEQ ID NO: 9; and a $V_L$ comprising the amino acid sequence of SEQ ID NO: 19; (v) a $V_H$ comprising the amino acid sequence of SEQ ID NO: 11; and a $V_L$ comprising the amino acid sequence of SEQ ID NO: 19; (vi) a $V_H$ comprising the amino acid sequence of SEQ ID NO: 11; and a $V_L$ comprising the amino acid sequence of SEQ ID NO: 20; (vii) a $V_H$ comprising the amino acid sequence of SEQ ID NO: 12; and a $V_L$ comprising the amino acid sequence of SEQ ID NO: 17; (viii) a $V_H$ comprising the amino acid sequence of SEQ ID NO: 12; and a $V_L$ comprising the amino acid sequence of SEQ ID NO: 19; (ix) a $V_H$ comprising the amino acid sequence of SEQ ID NO: 12; and a $V_L$ comprising the amino acid sequence of SEQ ID NO: 20; (x) a $V_H$ comprising the amino acid sequence of SEQ ID NO: 13; and a $V_L$ comprising the amino acid sequence of SEQ ID NO: 17; or (xi) a $V_H$ comprising the amino acid sequence of SEQ ID NO: 8; and a $V_L$ comprising the amino acid sequence of SEQ ID NO: 24.

In some embodiments, there is provided an isolated anti-NGF antibody that specifically binds to NGF competitively with any one of the isolated anti-NGF antibodies as described above. In some embodiments, there is provided an isolated anti-NGF antibody that specifically binds to the same epitope as any one of isolated anti-NGF antibodies as described above.

In some embodiments according to any of the isolated anti-NGF antibodies described above, the isolated anti-NGF antibody comprises an Fc fragment. In some embodiments, the isolated anti-NGF antibody is a full-length IgG antibody. In some embodiments, the isolated anti-NGF antibody is a full-length IgG1 or IgG4 antibody. In some embodiments, the anti-NGF antibody is a chimeric, human, or humanized antibody. In some embodiments, the anti-NGF antibody is an antigen binding fragment selected from the group consisting of a Fab, a Fab', a F(ab)'2, a Fab'-SH, a single-chain Fv (scFv), an Fv fragment, a dAb, a Fd, a nanobody, a diabody, and a linear antibody.

In some embodiments, there is provided isolated nucleic acid molecule(s) that encodes any one of the anti-NGF antibodies described above. In some embodiments, there is provided a vector comprising any one of the nucleic acid molecules described above. In some embodiments, there is provided a host cell comprising any one of the anti-NGF antibodies described above, any one of the nucleic acid molecules described above, or any one of the vectors described above. In some embodiments, there is provided a method of producing an anti-NGF antibody, comprising: a) culturing any one of the host cells described above under conditions effective to express the anti-NGF antibody; and b) obtaining the expressed anti-NGF antibody from the host cell.

In some embodiments, there is provided a method of treating a disease or condition in an individual in need thereof, comprising administering to the individual an effective amount of any one of the anti-NGF antibodies described above. In some embodiments, use of any one of the anti-NGF antibodies described above in the manufacture of a medicament for treating a disease or condition. In some embodiments, the disease or condition is caused by increased expression of NGF or increased sensitivity to NGF. In some embodiments, the disease or condition is selected from the group consisting of inflammatory pain, post-operative incision pain, neuropathic pain, fracture pain, gout joint pain, post-herpetic neuralgia, pain resulting from burns, cancer pain, osteoarthritis or rheumatoid arthritis pain, sciatica, and pain associated with sickle cell crises.

Also provided are pharmaceutical compositions, kits and articles of manufacture comprising any one of the anti-NGF antibodies or fragments described above.

BRIEF DESCRIPTION OF THE DRAWINGS

FIG. 1A shows results of the inhibitory effect of Ab4, Ab6, Ab10, Ab16 or Ab36 on the binding of NGF to receptor TrkA. FIG. 1B shows results of the inhibitory effect of Ab37, Ab44, Ab46, Ab47 or Ab54 on the binding of NGF to receptor TrkA. FIG. 1C shows results of the inhibitory effect of Ab4 or Ab61 on the binding of NGF to receptor TrkA.

FIG. 3A shows cross reactivities of the optimized anti-NGF antibody Ab4, Ab6, Ab36, Ab44 or Ab54 with BDNF. FIG. 3B shows cross reactivities of the optimized anti-NGF antibody Ab4, Ab6, Ab36, Ab44 or Ab54 with NT-3. FIG. 3C shows cross reactivities of the optimized anti-NGF antibody Ab4, Ab6, Ab36, Ab44 or Ab54 with NT-4.

FIG. 4A shows the polyspecificity results of the optimized anti-NGF antibody Ab4, Ab6, Ab36, Ab44 or Ab54 to dsDNA. FIG. 4B shows the polyspecificity results of the optimized anti-NGF antibody Ab4, Ab6, Ab36, Ab44 or Ab54 to insulin. FIG. 4C shows the polyspecificity results of the optimized anti-NGF antibody Ab4, Ab6, Ab36, Ab44 or Ab54 to Baculovirus particles.

FIG. 5A shows results of the optimized anti-NGF antibody Ab6, Ab10 or Ab16 in inhibiting NGF-induced TF1 cell proliferation. FIG. 5B shows the results of the optimized anti-NGF antibody Ab4, Ab36, Ab37 or Ab54 in inhibiting NGF-induced TF1 cell proliferation.

DETAILED DESCRIPTION OF THE APPLICATION

Figure 1A:
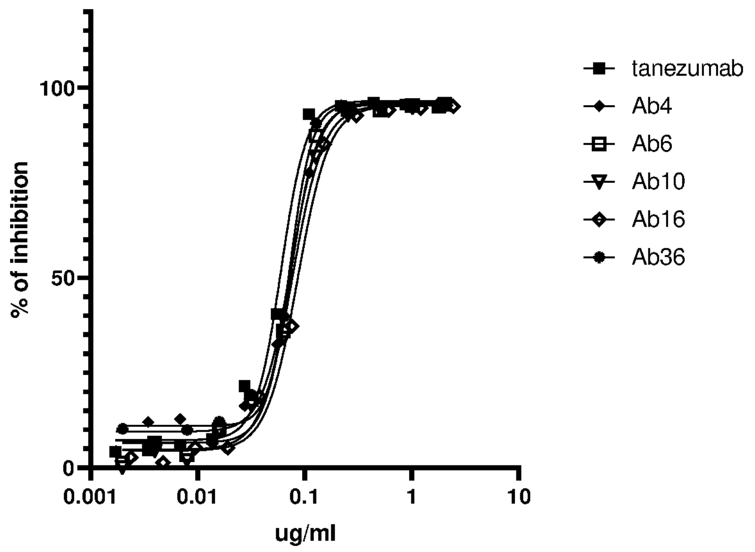
FIGS. 1A-1C show results of the inhibitory effect of the optimized anti-NGF antibodies on the binding of NGF to receptor TrkA, compared with the reference antibody Tanezumab.

The present application in one aspect provides anti-NGF antibodies. By using a combination of selections on scFv yeast display library and appropriately designed biochemical and biological assays, we have identified highly potent antibody molecules that bind to human NGF and inhibit the action of human NGF to its receptors. The results presented herein indicate that our antibodies exhibit high specificity for human NGF, for example, do not cross-react with closely related neurotrophin-3 (NT-3), neurotrophin-4 (NT-4) and Brain-derived neurotrophic factor (BDNF) compared with the known anti-NGF antibodies such as Tanezumab and Fulranumab, and surprisingly are even more potent than the known antibodies as demonstrated in a variety of biological assays (Tanezumab and Fulranumab were expressed according to the published sequences and purified, used as experiment references).

The anti-NGF antibodies or fragments provided by the present application include, for example, full-length anti-NGF antibodies, anti-NGF scFvs, anti-NGF Fc fusion proteins, multi-specific (such as bispecific) anti-NGF antibodies, anti-NGF immunoconjugates, and the like.

In some embodiments according to any one of the isolated anti-NGF antibodies described above, the isolated anti-NGF antibody comprises: a heavy chain variable domain ($V_H$) comprising a heavy chain complementarity determining region (HC-CDR) 1 comprising TYWIS (SEQ ID NO: 1); an HC-CDR2 comprising AIDPSDSDARYSPSFQG (SEQ ID NO: 2); and an HC-CDR3 comprising SDPGYSGYSLLYGFDS (SEQ ID NO: 3) or a variant thereof comprising up to about 5 amino acid substitutions in the HC-CDRs; and a light chain variable domain ($V_L$) comprising a light chain complementarity determining region (LC-CDR) 1 comprising RSSQSLVQRNX$_1$NTYLS (SEQ ID NO: 30), wherein X$_1$ can be any amino acid; a LC-CDR2 comprising QVSNRYS (SEQ ID NO: 5); and a LC-CDR3 comprising GQGAHLPLT (SEQ ID NO: 6) or a variant thereof comprising up to about 5 amino acid substitutions in the LC-CDRs.

In some embodiments according to any one of the isolated anti-NGF antibodies described above, the isolated anti-NGF antibody comprises: a heavy chain variable domain ($V_H$) comprising a heavy chain complementarity determining region (HC-CDR) 1 comprising TYWIS (SEQ ID NO: 1); an HC-CDR2 comprising AIDPSDSDARYSPSFQG (SEQ ID NO: 2); and an HC-CDR3 comprising SDPGYSGYSLLYGFDS (SEQ ID NO: 3) or a variant thereof comprising up to about 5 amino acid substitutions in the HC-CDRs; and a light chain variable domain ($V_L$) comprising a light chain complementarity determining region (LC-CDR) 1 comprising RSSQSLVQRNX$_1$NTYLS (SEQ ID NO: 39), wherein X$_1$ is G, A, S, or T; a LC-CDR2 comprising QVSNRYS (SEQ ID NO: 5); and a LC-CDR3 comprising GQGAHLPLT (SEQ ID NO: 6) or a variant thereof comprising up to about 5 amino acid substitutions in the LC-CDRs.

In one aspect, there is provided an anti-NGF antibody, wherein the anti-NGF antibody comprises a heavy chain variable domain ($V_H$) comprising a heavy chain variable domain ($V_H$) comprising an HC-CDR1 comprising TYWIS (SEQ ID NO: 1); an HC-CDR2 comprising AIDPSDSDARYSPSFQG (SEQ ID NO: 2); and an HC-CDR3 comprising SDPGYSGYSLLYGFDS (SEQ ID NO: 3); and a light chain variable domain ($V_L$) comprising a LC-CDR1 comprising RSSQSLVQRNGNTYLS (SEQ ID NO: 4) or RSSQSLVQRNANTYLS (SEQ ID NO: 7); a LC-CDR2 comprising QVSNRYS (SEQ ID NO: 5); and a LC-CDR3 comprising GQGAHLPLT (SEQ ID NO: 6).

Also provided are nucleic acids encoding the anti-NGF antibodies, compositions comprising the anti-NGF antibodies, and methods of making and using the anti-NGF antibodies.

DEFINITIONS

As used herein, "treatment" or "treating" is an approach for obtaining beneficial or desired results, including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delaying or slowing the progression of the disease, ameliorating the disease state, providing a remission (partial or total) of the disease, decreasing the dose of one or more of other medications required to treat the disease, delaying the progression of the disease, increasing or improving the quality of life, increasing weight gain, and/or prolonging survival. Also encompassed by "treatment" is a reduction of pathological consequence of the disease (such as, for example, tumor volume for cancer). The methods of the application contemplate any one or more of these aspects of treatment.

The term "antibody" includes full-length antibodies and antigen-binding fragments thereof. A full-length antibody comprises two heavy chains and two light chains. The variable regions of the light and heavy chains are responsible for antigen binding. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgAQ1 (α1 heavy chain), or IgA2 (α2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody "competes" for binding to a target NGF with a second antibody when the first antibody inhibits target NGF binding of the second antibody by at least about 50% (such as at least about any of 55%, 60%, 65%, 70%, 75%, 80%, 85%, 90%, 95%, 98% or 99%) in the presence of an equimolar concentration of the first antibody, or vice versa. A high throughput process for "binning" antibodies based upon their cross-competition is described in PCT Publication No. WO 03/48731.

As use herein, the term "specifically binds," "specifically recognizing," or "is specific for" refers to measurable and reproducible interactions, such as binding between a target and an antibody that is determinative of the presence of the target in the presence of a heterogeneous population of molecules, including biological molecules. For example, an antibody that specifically recognizes a target (which can be an epitope) is an antibody that binds this target with greater affinity, avidity, more readily, and/or with greater duration than its bindings to other targets. In some embodiments, an antibody that specifically recognizes an antigen reacts with one or more antigenic determinants of the antigen with a binding affinity that is at least about 10 times its binding affinity for other targets.

An "isolated" anti-NGF antibody as used herein refers to an anti-NGF antibody that (1) is not associated with proteins found in nature, (2) is free of other proteins from the same source, (3) is expressed by a cell from a different species, or, (4) does not occur in nature.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., *J. Mol. Biol.,* 273: 927-948 (1997); MacCallum et al., J. Mol. Biol. 262:732-745 (1996); Abhinandan and Martin, *Mol. Immunol.,* 45:3832-3839 (2008); Lefranc M. P. et al., *Dev. Comp. Immunol.,* 27:55-77 (2003); and Honegger and Plückthun, *J. Mol. Biol.,* 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, *Mol. Immunol.,* 45:3832-3839 (2008); Ehrenmann F. et al., *Nucleic Acids Res.,* 38: D301-D307 (2010); and Adolf-Bryfogle J. et al., *Nucleic Acids Res.,* 43: D432-D438 (2015). The contents of the references cited in this paragraph are incorporated herein by reference in their entireties for use in the present application and for possible inclusion in one or more claims herein.

TABLE 1

| CDR DEFINITIONS | | | | | |
|---|---|---|---|---|---|
| | Kabat[1] | Chothia[2] | MacCallum[3] | IMGT[4] | AHo[5] |
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this application (see U.S. Pat. No. 4,816,567; and Morrison et al., Proc. Natl. Acad. Sci. USA, 81:6851-6855 (1984)).

"Fv" is the minimum antibody fragment which contains a complete antigen-recognition and binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA,* 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32 (5): 1792-1797, 2004*; Edgar, R. C., BMC Bioinformatics* 5 (1): 113, 2004).

The terms "Fc receptor" or "FcR" are used to describe a receptor that binds to the Fc region of an antibody. In some embodiments, an FcR of this application is one that binds an IgG antibody (a γ receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daeron, *Annu. Rev. Immunol.* 15:203-234 (1997)). The term includes allotypes, such as FcγRIIIA allotypes: FcγRIIIA-Phe158, FcγRIIIA-Val158, FcγRIIA-R131 and/or FcγRIIA-H131. FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "FcRn" refers to the neonatal Fc receptor (FcRn). FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "CH1 domain" of a human IgG Fc region usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" comprises the stretch of residues of C-terminal to a CH2 domain in an Fc region (i.e. from about amino acid residue 341 to the C-terminal end of an antibody sequence, typically at amino acid residue 446 or 447 of an IgG).

A "functional Fc fragment" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art.

An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent Kd or $IC_{50}$ value) than the parent polypeptide or a native sequence IgG Fc. According to some embodiments, the improvement in binding compared to a parent polypeptide is about 3 fold, such as about any of 5, 10, 25, 50, 60, 100, 150, 200, or up to 500 fold, or about 25% to 1000% improvement in binding. The polypeptide variant which "exhibits decreased binding" to an FcR, binds at least one FcR with lower affinity (e.g., higher apparent Kd or higher $IC_{50}$ value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (USA) 95:652-656 (1998).

The polypeptide comprising a variant Fc region which "exhibits increased ADCC" or mediates ADCC in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g., in an animal model etc. In some embodiments, the variant is from about 5 fold to about 100 fold, e.g. from about 25 to about 50 fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See also, Idusogie et al. *J. Immunol.* 164:4178-4184 (2000).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

An "effective amount" of an anti-NGF antibody or composition as disclosed herein, is an amount sufficient to carry out a specifically stated purpose. An "effective amount" can be determined empirically and by known methods relating to the stated purpose.

An "effective amount" of drug, compound, or pharmaceutical composition is an amount sufficient to effect beneficial or desired results including clinical results such as alleviation or reduction in pain sensation. An effective amount can be administered in one or more administrations. For purposes of this invention, an effective amount of drug, compound, or pharmaceutical composition is an amount sufficient to treat, ameliorate, reduce the intensity of and/or prevent pain, including post-surgical pain, rheumatoid arthritis pain, and/or osteoarthritis pain. In some embodiments, the "effective amount" may reduce pain at rest (resting pain) or mechanically-induced pain (including pain following movement), or both, and it may be administered before, during or after an incision, cut, tear or injury and/or before, during or after painful stimulus. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, by "pharmaceutically acceptable" or "pharmacologically compatible" is meant a material that is not biological or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

It is understood that embodiments of the application described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "an," and "the" include plural referents unless the context clearly dictates otherwise.

Anti-NGF Antibodies

In one aspect, the present application provides anti-NGF antibodies that specifically bind to NGF. Anti-NGF antibodies include, but are not limited to, humanized antibodies, chimeric antibodies, mouse antibodies, human antibodies, and antibodies comprising the heavy chain and/or light chain CDRs discussed herein. In one aspect, the present application provides isolated antibodies that bind to NGF. Contemplated anti-NGF antibodies include, for example, full-length anti-NGF antibodies (e.g., full-length IgG1 or IgG4), anti-NGF scFvs, anti-NGF Fc fusion proteins, multi-specific (such as bispecific) anti-NGF antibodies, anti-NGF immunoconjugates, and the like. In some embodiments, the anti-NGF antibody is a full-length antibody (e.g., full-length IgG1 or IgG4) or antigen-binding fragment thereof, which specifically binds to NGF. In some embodiments, the anti-NGF antibody is a Fab, a Fab', a F(ab)'2, a Fab'-SH, a single-chain Fv (scFv), an Fv fragment, a dAb, a Fd, a nanobody, a diabody, or a linear antibody. In some embodiments, reference to an antibody that specifically binds to NGF means that the antibody binds to NGF with an affinity that is at least about 10 times (including for example at least about any one of 10, $10^2$, $10^3$, $10^4$, $10^5$, $10^6$, or $10^7$ times) more tightly than its binding affinity for a non-target. In some embodiments, the non-target is an antigen that is not NGF. Binding affinity can be determined by methods known in the art, such as ELISA, fluorescence activated cell sorting (FACS) analysis, or radioimmunoprecipitation assay (RIA). Kd can be determined by methods known in the art, such as surface plasmon resonance (SPR) assay or biolayer interferometry (BLI).

Although anti-NGF antibodies containing human sequences (e.g., human heavy and light chain variable domain sequences comprising human CDR sequences) are extensively discussed herein, non-human anti-NGF antibodies are also contemplated. In some embodiments, non-human anti-NGF antibodies comprise human CDR sequences from an anti-NGF antibody as described herein and non-human framework sequences. Non-human framework sequences include, in some embodiments, any sequence that can be used for generating synthetic heavy and/or light chain variable domains using one or more human CDR sequences as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. In some embodiments, a non-human anti-NGF antibody includes an anti-NGF antibody generated by grafting one or more human CDR sequences as described herein onto a non-human framework sequence (e.g., a mouse or chicken framework sequence).

In some embodiments, the anti-NGF antibody described herein specifically recognizes an epitope within human NGF. In some embodiments, the anti-NGF antibody cross-reacts with NGF from species other than human. In some embodiments, the anti-NGF antibody is completely specific for human NGF and does not exhibit cross-reactivity with NGFs from other non-human species.

In some embodiments, the anti-NGF antibody described herein specifically binds to a linear epitope within human NGF. In some embodiments, the anti-NGF antibody described herein specifically binds to a nonlinear epitope within human NGF.

In some embodiments, the anti-NGF antibody cross-reacts with at least one allelic variant of the NGF protein (or fragments thereof). In some embodiments, the allelic variant has up to about 30 (such as about any of 1, 2, 3, 4, 5, 6, 7, 8, 9, 10, 15, 20, 25, or 30) amino acid substitutions (such as a conservative substitution) when compared to the naturally occurring NGF (or fragments thereof). In some embodiments, the anti-NGF antibody does not cross-react with any allelic variants of the NGF protein (or fragments thereof).

In some embodiments, the anti-NGF antibody cross-reacts with at least one interspecies variant of the NGF protein. In some embodiments, for example, the NGF protein (or fragments thereof) is a human NGF and the interspecies variant of the NGF protein (or fragments thereof) is a cynomolgus monkey variant, mouse variant or rat variant thereof. In some embodiments, the anti-NGF antibody does not cross-react with any interspecies variant of the NGF protein.

In some embodiments, according to any of the anti-NGF antibodies described herein, the anti-NGF antibody comprises an antibody heavy chain constant region and an antibody light chain constant region. In some embodiments, the anti-NGF antibody comprises an IgG1 heavy chain constant region. In some embodiments, the anti-NGF antibody comprises an IgG2 heavy chain constant region. In some embodiments, the anti-NGF antibody comprises an IgG3 heavy chain constant region. In some embodiments, the anti-NGF antibody comprises an IgG4 heavy chain constant region. In some embodiments, the heavy chain constant region comprises (including consisting of or consisting essentially of) the amino acid sequence of SEQ ID NO: 25. In some embodiments, the heavy chain constant region comprises (including consisting of or consisting essentially of) the amino acid sequence of SEQ ID NO: 26. In some embodiments, the anti-NGF comprises a lambda light chain constant region. In some embodiments, the anti-NGF antibody comprises a kappa light chain constant region. In some embodiments, the light chain constant region comprises (including consisting of or consisting essentially of) the amino acid sequence of SEQ ID NO: 27. In some embodiments, the anti-NGF antibody comprises an antibody heavy chain variable domain and an antibody light chain variable domain.

In some embodiments, the anti-NGF antibody comprises a $V_H$ comprising: an HC-CDR1 comprising (including consisting of or consisting essentially of) the amino acid sequence of SEQ ID NO: 1, or a variant thereof comprising up to about 3 (such as about any of 1, 2, or 3) amino acid substitutions, an HC-CDR2 comprising (including consisting of or consisting essentially of) the amino acid sequence of SEQ ID NO: 2, or a variant thereof comprising up to about 3 (such as about any of 1, 2, or 3) amino acid substitutions, and an HC-CDR3 comprising (including consisting of or consisting essentially of) the amino acid sequence of any one of SEQ ID NO: 3, or a variant thereof comprising up to about 3 (such as about any of 1, 2, or 3) amino acid substitutions.

In some embodiments, the anti-NGF antibody comprises a $V_H$ comprising: an HC-CDR1 comprising (including consisting of or consisting essentially of) the amino acid sequence of SEQ ID NO: 1, an HC-CDR2 comprising (including consisting of or consisting essentially of) the amino acid sequence of SEQ ID NO: 2, and an HC-CDR3 comprising (including consisting of or consisting essentially of) the amino acid sequence of SEQ ID NO: 3.

In some embodiments, the anti-NGF antibody comprises a $V_L$ comprising: an LC-CDR1 comprising (including consisting of or consisting essentially of) the amino acid sequence of any one of SEQ ID NOs: 4 or SEQ ID NO: 7, or a variant thereof comprising up to about 3 (such as about any of 1, 2, or 3) amino acid substitutions, an LC-CDR2 comprising (including consisting of or consisting essentially of) the amino acid sequence of SEQ ID NO: 5, or a variant thereof comprising up to about 3 (such as about any of 1, 2, or 3) amino acid substitutions, and an LC-CDR3 comprising (including consisting of or consisting essentially of) the amino acid sequence of any one of SEQ ID NO: 6, or a variant thereof comprising up to about 3 (such as about any of 1, 2, or 3) amino acid substitutions.

In some embodiments, the anti-NGF antibody comprises a $V_L$ comprising: an LC-CDR1 comprising (including consisting of or consisting essentially of) the amino acid sequence of any one of SEQ ID NOs: 4 or SEQ ID NO: 7, an LC-CDR2 comprising (including consisting of or consisting essentially of) the amino acid sequence of SEQ ID NO: 5, and an LC-CDR3 comprising (including consisting of or consisting essentially of) the amino acid sequence of SEQ ID NO: 6.

In some embodiments according to any one of the isolated anti-NGF antibodies described above, the isolated anti-NGF antibody comprises: a heavy chain variable domain ($V_H$) comprising a heavy chain complementarity determining region (HC-CDR) 1 comprising TYWIS (SEQ ID NO: 1); an HC-CDR2 comprising AIDPSDSDARYSPSFQG (SEQ ID NO: 2); and an HC-CDR3 comprising SDPGYSGYSLLYGFDS (SEQ ID NO: 3) or a variant thereof comprising up to about 5 amino acid substitutions in the HC-CDRs; and a light chain variable domain ($V_L$) comprising a light chain complementarity determining region (LC-CDR) 1 comprising RSSQSLVQRNX$_1$NTYLS (SEQ ID NO: 30), wherein X$_1$ can be any amino acid; a LC-CDR2 comprising QVSNRYS (SEQ ID NO: 5); and a LC-CDR3 comprising GQGAHLPLT (SEQ ID NO: 6) or a variant thereof comprising up to about 5 amino acid substitutions in the LC-CDRs.

In some embodiments, the anti-NGF antibody comprises a $V_H$ comprising: an HC-CDR1 comprising the amino acid sequence of SEQ ID NO: 1, or a variant thereof comprising up to about 3 (such as about any of 1, 2, or 3) amino acid substitutions, an HC-CDR2 comprising the amino acid sequence of SEQ ID NO: 2, or a variant thereof comprising up to about 3 (such as about any of 1, 2, or 3) amino acid substitutions, and an HC-CDR3 comprising the amino acid sequence of SEQ ID NO: 3, or a variant thereof comprising up to about 3 (such as about any of 1, 2, or 3) amino acid substitutions; and a $V_L$ comprising: an LC-CDR1 comprising the amino acid sequence of any one of SEQ ID NO: 4 or SEQ ID NO: 7, or a variant thereof comprising up to about 3 (such as about any of 1, 2, or 3) amino acid substitutions, an LC-CDR2 comprising the amino acid sequence of SEQ ID NO: 5, or a variant thereof comprising up to about 3 (such as about any of 1, 2, or 3) amino acid substitutions, and an LC-CDR3 comprising the amino acid sequence of SEQ ID NO: 6, or a variant thereof comprising up to about 3 (such as about any of 1, 2, or 3) amino acid substitutions.

In some embodiments, the anti-NGF antibody comprises a $V_H$ comprising: an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3, or a variant thereof comprising up to about 5 amino acid substitutions in the HC-CDRs; and a $V_L$ comprising: an LC-CDR1 comprising the amino acid sequence of SEQ ID NO: 4 or SEQ ID NO: 7, an LC-CDR2 comprising the amino acid sequence of SEQ ID NO: 5, and an LC-CDR3 comprising the amino acid sequence of SEQ ID NO: 6, or a variant thereof comprising up to about 5 amino acid substitutions in the LC-CDRs.

In some embodiments, the anti-NGF antibody comprises a $V_H$ comprising: an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3; and a $V_L$ comprising an LC-CDR1 comprising the amino acid sequence of SEQ ID NO: 4, an LC-CDR2 comprising the amino acid sequence of SEQ ID NO: 5, and an LC-CDR3 comprising the amino acid sequence of SEQ ID NO: 6.

In some embodiments, the anti-NGF antibody comprises a $V_H$ comprising: an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3; and a $V_L$ comprising an LC-CDR1 comprising the amino acid sequence of SEQ ID NO: 7, an LC-CDR2 comprising the amino acid sequence of SEQ ID NO: 5, and an LC-CDR3 comprising the amino acid sequence of SEQ ID NO: 6.

In some embodiments, the anti-NGF antibody comprises a $V_H$ comprising the amino acid sequence of any one of SEQ ID NOs: 8-13, or a variant thereof comprising up to about 5 amino acid substitutions; and a $V_L$ comprising the amino acid sequence of any one of SEQ ID NOs: 14-24, or a variant thereof comprising up to about 5 amino acid substitutions. In some embodiments, the anti-NGF antibody comprises a $V_H$ comprising the amino acid sequence of any one of SEQ ID NOs: 8-13; and a $V_L$ comprising the amino acid sequence of any one of SEQ ID NOs: 14-24.

In some embodiments, the anti-NGF antibody comprises a $V_H$ comprising the amino acid sequences of SEQ ID NOs: 1, 2 and 3, or a variant thereof comprising up to about 5 amino acid substitutions; and a $V_L$ comprising the amino acid sequences of SEQ ID NOs: 4, 5 and 6, or a variant thereof comprising up to about 5 amino acid substitutions. In some embodiments, the anti-NGF antibody comprises a $V_H$ comprising the amino acid sequences of SEQ ID NOs: 1, 2 and 3; and a $V_L$ comprising the amino acid sequences of SEQ ID NOS: 4, 5 and 6.

In some embodiments, the anti-NGF antibody comprises a $V_H$ comprising the amino acid sequences of SEQ ID NOs: 1, 2 and 3, or a variant thereof comprising up to about 5 amino acid substitutions; and a $V_L$ comprising the amino acid sequences of SEQ ID NOs: 7, 5 and 6, or a variant thereof comprising up to about 5 amino acid substitutions. In some embodiments, the anti-NGF antibody comprises a $V_H$ comprising the amino acid sequences of SEQ ID NOs: 1, 2 and 3; and a $V_L$ comprising the amino acid sequences of SEQ ID NOS: 7, 5 and 6.

In some embodiments, the anti-NGF antibody heavy chain variable region comprises: a framework region FR1 comprising EVQLVQSGAEVKKPG$X_1X_2X_3$KISCK$X_4$SGY$X_5$FI (SEQ ID NO: 31), wherein $X_1$ is A or E, $X_2$ is T or S, $X_3$ is V or L, $X_4$ is V, G, or I, $X_5$ is T or S, or a variant thereof comprising up to about 5 amino acid substitutions; a framework region FR2 comprising WV$X_1$Q$X_2$PGKGLEWMG (SEQ ID NO: 32), wherein $X_1$ is Q or R, $X_2$ is A or M, or a variant thereof comprising up to about 5 amino acid substitutions; a framework region FR3 comprising $X_1$VTI$X_2$AD$X_3$S$X_4X_5$TAY$X_6X_7X_8$SSL$X_9X_{10}X_{11}$DTA$X_{12}$YYCAK (SEQ ID NO: 33), wherein $X_1$ is R or Q, $X_2$ is T or S, $X_3$ is T or K, $X_4$ is T or I, $X_5$ is D or S, $X_6$ is M or L, $X_7$ is E or Q, $X_8$ is L or W, $X_9$ is R or K, $X_{10}$ is S or A, $X_{11}$ is E or S, $X_{12}$ is V or M, or a variant thereof comprising up to about 5 amino acid substitutions; a framework region FR4 comprising WGQGTLVTVSS (SEQ ID NO: 34), or a variant thereof comprising up to about 5 amino acid substitutions.

In some embodiments, the anti-NGF antibody light chain variable region comprises: a framework region FR1 comprising D$X_1$VMTQ$X_2$PLS$X_3$PVTLGQPASISC (SEQ ID NO: 35), wherein $X_1$ is I or V, $X_2$ is T or S, $X_3$ is S or L, or a variant thereof comprising up to about 5 amino acid substitutions; a framework region FR2 comprising W$X_1$QQRPGQ$X_2$PRLLIY (SEQ ID NO: 36), wherein $X_1$ is L, Y, or F, $X_2$ is P or S, or a variant thereof comprising up to about 5 amino acid substitutions; a framework region FR3 comprising GVPDRFSGSG$X_1$GTDFTLKISRVEAEDVGVYYC (SEQ ID NO: 37), wherein $X_1$ is A or S, or a variant thereof comprising up to about 5 amino acid substitutions; a framework region FR4 comprising FGQGTKVEIK (SEQ ID NO: 38), or a variant thereof comprising up to about 5 amino acid substitutions.

In some embodiments, the anti-NGF antibody comprises heavy chain variable region comprising: a framework region FR1 comprising EVQLVQSGAEVKKPG$X_1X_2X_3$KISCK$X_4$SGY$X_5$FI (SEQ ID NO: 31), wherein $X_1$ is A or E, $X_2$ is T or S, $X_3$ is V or L, $X_4$ is V, G, or I, $X_5$ is T or S; a framework region FR2 comprising WV$X_1$Q$X_2$PGKGLEWMG (SEQ ID NO: 32), wherein $X_1$ is Q or R, $X_2$ is A or M; a framework region FR3 comprising $X_1$VTI$X_2$AD$X_3$S$X_4X_5$TAY$X_6X_7X_8$SSL$X_9X_{10}X_{11}$DTA$X_{12}$YYCAK (SEQ ID NO: 33), wherein $X_1$ is R or Q, $X_2$ is T or S, $X_3$ is T or K, $X_4$ is T or I, $X_5$ is D or S, $X_6$ is M or L, $X_7$ is E or Q, $X_8$ is L or W, $X_9$ is R or K, $X_{10}$ is S or A, $X_{11}$ is E or S, $X_{12}$ is V or M; a framework region FR4 comprising WGQGTLVTVSS (SEQ ID NO: 34); and light chain variable region comprising: a framework region FR1 comprising D$X_1$VMTQ$X_2$PLS$X_3$PVTLGQPASISC (SEQ ID NO: 35), wherein $X_1$ is I or V, $X_2$ is T or S, $X_3$ is S or L; a framework region FR2 comprising W$X_1$QQRPGQ$X_2$PRLLIY (SEQ ID NO: 36), wherein $X_1$ is L, Y, or F, $X_2$ is P or S; a framework region FR3 comprising GVPDRFSGSG$X_1$GTDFTLKISRVEAEDVGVYYC (SEQ ID NO: 37), wherein $X_1$ is A or S; a framework region FR4 comprising FGQGTKVEIK (SEQ ID NO: 38).

In some embodiments, the anti-NGF antibody comprises a $V_H$ comprising an HC-CDR1, an HC-CDR2 and an HC-CDR3 of the $V_H$ comprising the amino acid sequence of any one of SEQ ID NOs: 8-13; and a $V_L$ comprising a LC-CDR1, a LC-CDR2, and a LC-CDR3 of the $V_L$ comprising the amino acid sequence of any one of SEQ ID NOs: 14-24.

In some embodiments, the anti-NGF antibody comprises a $V_H$ comprising one, two or three HC-CDRs of SEQ ID NO: 8. In some embodiments, the anti-NGF antibody comprises a $V_H$ comprising one, two or three HC-CDRs of SEQ ID NO: 9. In some embodiments, the anti-NGF antibody comprises a $V_H$ comprising one, two or three HC-CDRs of SEQ ID NO: 11. In some embodiments, the anti-NGF antibody comprises a $V_H$ comprising one, two or three HC-CDRs of SEQ ID NO: 12. In some embodiments, the anti-NGF antibody comprises a $V_H$ comprising one, two or three HC-CDRs of SEQ ID NO: 13.

In some embodiments, the anti-NGF antibody comprises a $V_L$ comprising one, two or three LC-CDRs of SEQ ID NO: 17. In some embodiments, the anti-NGF antibody comprises a $V_L$ comprising one, two or three LC-CDRs of SEQ ID NO: 19. In some embodiments, the anti-NGF antibody comprises a $V_L$ comprising one, two or three LC-CDRs of SEQ ID NO: 20. In some embodiments, the anti-NGF antibody comprises a $V_L$ comprising one, two or three LC-CDRs of SEQ ID NO: 23. In some embodiments, the anti-NGF antibody comprises a $V_L$ comprising one, two or three LC-CDRs of SEQ ID NO: 24.

In some embodiments, the anti-NGF antibody comprises a $V_H$ comprising HC-CDR1, HC-CDR2 and HC-CDR3 of the $V_H$ of SEQ ID NO: 8, and a $V_L$ comprising LC-CDR1, LC-CDR2 and LC-CDR3 of the $V_L$ of SEQ ID NO: 17. In some embodiments, the anti-NGF antibody comprises a $V_H$ comprising HC-CDR1, HC-CDR2 and HC-CDR3 of the $V_H$ of SEQ ID NO: 8, and a $V_L$ comprising LC-CDR1, LC-CDR2 and LC-CDR3 of the $V_L$ of SEQ ID NO: 19. In some embodiments, the anti-NGF antibody comprises a $V_H$ comprising HC-CDR1, HC-CDR2 and HC-CDR3 of the $V_H$ of SEQ ID NO: 8, and a $V_L$ comprising LC-CDR1, LC-CDR2 and LC-CDR3 of the $V_L$ of SEQ ID NO: 23. In some embodiments, the anti-NGF antibody comprises a $V_H$ comprising HC-CDR1, HC-CDR2 and HC-CDR3 of the $V_H$ of SEQ ID NO: 9, and a $V_L$ comprising LC-CDR1, LC-CDR2 and LC-CDR3 of the $V_L$ of SEQ ID NO: 19. In some embodiments, the anti-NGF antibody comprises a $V_H$ comprising HC-CDR1, HC-CDR2 and HC-CDR3 of the $V_H$ of SEQ ID NO: 11, and a $V_L$ comprising LC-CDR1, LC-CDR2 and LC-CDR3 of the $V_L$ of SEQ ID NO: 19. In some embodiments, the anti-NGF antibody comprises a $V_H$ comprising HC-CDR1, HC-CDR2 and HC-CDR3 of the $V_H$ of SEQ ID NO: 11, and a $V_L$ comprising LC-CDR1, LC-CDR2 and LC-CDR3 of the $V_L$ of SEQ ID NO: 20. In some embodiments, the anti-NGF antibody comprises a $V_H$ comprising HC-CDR1, HC-CDR2 and HC-CDR3 of the $V_H$ of SEQ ID NO: 12, and a $V_L$ comprising LC-CDR1, LC-CDR2 and LC-CDR3 of the $V_L$ of SEQ ID NO: 17. In some embodiments, the anti-NGF antibody comprises a $V_H$ comprising HC-CDR1, HC-CDR2 and HC-CDR3 of the $V_H$ of SEQ ID NO: 12, and a $V_L$ comprising LC-CDR1, LC-CDR2 and LC-CDR3 of the $V_L$ of SEQ ID NO: 19. In some embodiments, the anti-NGF antibody comprises a $V_H$ comprising HC-CDR1, HC-CDR2 and HC-CDR3 of the $V_H$ of SEQ ID NO: 12, and a $V_L$ comprising LC-CDR1, LC-CDR2 and LC-CDR3 of the $V_L$ of SEQ ID NO: 20. In some embodiments, the anti-NGF antibody comprises a $V_H$ comprising HC-CDR1, HC-CDR2 and HC-CDR3 of the $V_H$ of SEQ ID NO: 13, and a $V_L$ comprising LC-CDR1, LC-CDR2 and LC-CDR3 of the $V_L$ of SEQ ID NO: 17. In some embodiments, the anti-NGF antibody comprises a $V_H$ comprising HC-CDR1, HC-CDR2 and HC-CDR3 of the $V_H$ of SEQ ID NO: 8, and a $V_L$ comprising LC-CDR1, LC-CDR2 and LC-CDR3 of the $V_L$ of SEQ ID NO: 24.

In some embodiments, the anti-NGF antibody comprises a $V_H$ comprising the amino acid sequence of any one of SEQ ID NOs: 8-13, or a variant thereof having at least about 90% (for example at least about any of 91%, 92%, 93%, 94%, 95%, 96%, 97%, 98%, or 99%) sequence identity, and a $V_L$ comprising the amino acid sequence of any one of SEQ ID NOs: 14-24, or a variant thereof having at least about 90% sequence identity. In some embodiments, the anti-NGF antibody comprises a $V_H$ comprising the amino acid sequence of any one of SEQ ID NOs: 8-13, and a $V_L$ comprising the amino acid sequence of any one of SEQ ID NOs: 14-24.

In some embodiments, the anti-NGF antibody comprises a $V_H$ comprising the amino acid sequence of SEQ ID NO: 8, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 17, or a variant thereof having at least about 90% sequence identity. In some embodiments, the anti-NGF antibody comprises a $V_H$ comprising the amino acid sequence of SEQ ID NO: 8 and a $V_L$ comprising the amino acid sequence of SEQ ID NO: 17.

In some embodiments, the anti-NGF antibody comprises a $V_H$ comprising the amino acid sequence of SEQ ID NO: 8, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 19, or a variant thereof having at least about 90% sequence identity. In some embodiments, the anti-NGF antibody comprises a $V_H$ comprising the amino acid sequence of SEQ ID NO: 8 and a $V_L$ comprising the amino acid sequence of SEQ ID NO: 19.

In some embodiments, the anti-NGF antibody comprises a $V_H$ comprising the amino acid sequence of SEQ ID NO: 8, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 23, or a variant thereof having at least about 90% sequence identity. In some embodiments, the anti-NGF antibody comprises a $V_H$ comprising the amino acid sequence of SEQ ID NO: 8 and a $V_L$ comprising the amino acid sequence of SEQ ID NO: 23.

In some embodiments, the anti-NGF antibody comprises a $V_H$ comprising the amino acid sequence of SEQ ID NO: 9, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 19, or a variant thereof having at least about 90% sequence identity. In some embodiments, the anti-NGF antibody comprises a $V_H$ comprising the amino acid sequence of SEQ ID NO: 9 and a $V_L$ comprising the amino acid sequence of SEQ ID NO: 19.

In some embodiments, the anti-NGF antibody comprises a $V_H$ comprising the amino acid sequence of SEQ ID NO: 11, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 19, or a variant thereof having at least about 90% sequence identity. In some embodiments, the anti-NGF antibody comprises a $V_H$ comprising the amino acid sequence of SEQ ID NO: 11 and a $V_L$ comprising the amino acid sequence of SEQ ID NO: 19.

In some embodiments, the anti-NGF antibody comprises a $V_H$ comprising the amino acid sequence of SEQ ID NO: 11, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 20, or a variant thereof having at least about 90% sequence identity. In some embodiments, the anti-NGF antibody comprises a $V_H$ comprising the amino acid sequence of SEQ ID NO: 11 and a $V_L$ comprising the amino acid sequence of SEQ ID NO: 20.

In some embodiments, the anti-NGF antibody comprises a $V_H$ comprising the amino acid sequence of SEQ ID NO: 12, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 17, or a variant thereof having at least about 90% sequence identity. In some embodiments, the anti-NGF antibody comprises a $V_H$ comprising the amino acid sequence of SEQ ID NO: 12 and a $V_L$ comprising the amino acid sequence of SEQ ID NO: 17.

In some embodiments, the anti-NGF antibody comprises a $V_H$ comprising the amino acid sequence of SEQ ID NO: 12, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 19, or a variant thereof having at least about 90% sequence identity. In some embodiments, the anti-NGF antibody comprises a $V_H$ comprising the amino acid sequence of SEQ ID NO: 12 and a $V_L$ comprising the amino acid sequence of SEQ ID NO: 19.

In some embodiments, the anti-NGF antibody comprises a $V_H$ comprising the amino acid sequence of SEQ ID NO: 12, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 20, or a variant thereof having at least about 90% sequence identity. In some embodiments, the anti-NGF antibody comprises a $V_H$ comprising the amino acid sequence of SEQ ID NO: 12 and a $V_L$ comprising the amino acid sequence of SEQ ID NO: 20.

In some embodiments, the anti-NGF antibody comprises a $V_H$ comprising the amino acid sequence of SEQ ID NO: 13, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 17, or a variant thereof having at least about 90% sequence identity. In some embodiments, the anti-NGF antibody comprises a $V_H$ comprising the amino acid sequence of SEQ ID NO: 13 and a $V_L$ comprising the amino acid sequence of SEQ ID NO: 17.

In some embodiments, the anti-NGF antibody comprises a $V_H$ comprising the amino acid sequence of SEQ ID NO: 8, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 24, or a variant thereof having at least about 90% sequence identity. In some embodiments, the anti-NGF antibody comprises a $V_H$ comprising the amino acid sequence of SEQ ID NO: 8 and a $V_L$ comprising the amino acid sequence of SEQ ID NO: 24.

In some embodiments, functional epitopes can be mapped by combinatorial alanine scanning. In this process, a combinatorial alanine-scanning strategy can be used to identify amino acids in the NGF protein that are necessary for interaction with NGF antibodies. In some embodiments, the epitope is conformational and crystal structure of anti-NGF antibodies bound to NGF may be employed to identify the epitopes.

In some embodiments, the present application provides antibodies which compete with any one of the NGF antibodies described herein for binding to NGF. In some embodiments, the present application provides antibodies which compete with any one of the anti-NGF antibodies provided herein for binding to an epitope on the NGF. In some embodiments, an anti-NGF antibody is provided that binds to the same epitope as an anti-NGF antibody comprising a $V_H$ comprising the amino acid sequence of any one of SEQ ID NOs: 8-13, and a $V_L$ comprising the amino acid sequence of any one of SEQ ID NOs: 14-24. In some embodiments, an anti-NGF antibody is provided that specifically binds to NGF competitively with an anti-NGF antibody comprising a $V_H$ comprising the amino acid sequence of any one of SEQ ID NOs: 8-13, and a $V_L$ comprising the amino acid sequence of any one of SEQ ID NOs: 14-24.

In some embodiments, competition assays may be used to identify a monoclonal antibody that competes with an anti-NGF antibody described herein for binding to NGF. Competition assays can be used to determine whether two antibodies bind to the same epitope by recognizing identical or sterically overlapping epitopes or one antibody competitively inhibits binding of another antibody to the antigen. In certain embodiments, such a competing antibody binds to the same epitope that is bound by an antibody described herein. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). In some embodiments, two antibodies are said to bind to the same epitope if each blocks binding of the other by 50% or more. In some embodiments, the antibody that competes with an anti-NGF antibody described herein is a chimeric, humanized or human antibody.

Exemplary anti-NGF antibody sequences are shown in Tables 2 and 3, wherein the CDR numbering is according to the EU index of Kabat. Those skilled in the art will recognize that many algorithms are known for prediction of CDR positions and for delimitation of antibody heavy chain and light chain variable regions. Anti-NGF antibodies comprising CDRs, $V_H$ and/or $V_L$ sequences from antibodies described herein, but based on prediction algorithms other than those exemplified in the tables below, are within the scope of this invention.

TABLE 2

Exemplary anti-NGF antibody CDR sequences.

| Antibody Name | HC-CDR1 | HC-CDR2 | HC-CDR3 |
|---|---|---|---|
| Ab1-Ab61 | TYWIS (SEQ ID NO: 1) | AIDPSDSDARYSPSFQG (SEQ ID NO: 2) | SDPGYSGYSLLYGFDS (SEQ ID NO: 3) |
| **Antibody Name** | **LC-CDR1** | **LC-CDR2** | **LC-CDR3** |
| Ab1-Ab60 | RSSQSLVQRNGNTYLS (SEQ ID NO: 4) | QVSNRYS (SEQ ID NO: 5) | GQGAHLPLT (SEQ ID NO: 6) |
| Ab61 | RSSQSLVQRNANTYLS (SEQ ID NO: 7) | QVSNRYS (SEQ ID NO: 5) | GQGAHLPLT (SEQ ID NO: 6) |

TABLE 3

| Exemplary sequences. | | |
|---|---|---|
| SEQ ID NO | Description | Sequence |
| 8 | Ab1-Ab10, Ab61$V_H$ | EVQLVQSGAEVKKPGATVKISCKVSGYTFITYWISWVQQAPGKGLEWMGA IDPSDSDARYSPSFQGRVTITADTSTDTAYMELSSLRSEDTAVYYCAKSDPG YSGYSLLYGFDSWGQGTLVTVSS |
| 9 | Ab11-Ab20 $V_H$ | EVQLVQSGAEVKKPGATVKISCKVSGYSFITYWISWVQQAPGKGLEWMGA IDPSDSDARYSPSFQGRVTITADTSTDTAYMELSSLRSEDTAVYYCAKSDPG YSGYSLLYGFDSWGQGTLVTVSS |
| 10 | Ab21-Ab30 $V_H$ | EVQLVQSGAEVKKPGATVKISCKVSGYSFITYWISWVQQAPGKGLEWMGA IDPSDSDARYSPSFQGRVTITADKSTDTAYMELSSLRSEDTAVYYCAKSDPG YSGYSLLYGFDSWGQGTLVTVSS |
| 11 | Ab31-Ab40 $V_H$ | EVQLVQSGAEVKKPGATVKISCKVSGYTFITYWISWVQQAPGKGLEWMGA IDPSDSDARYSPSFQGRVTITADKSTDTAYMELSSLRSEDTAVYYCAKSDPG YSGYSLLYGFDSWGQGTLVTVSS |
| 12 | Ab41-Ab50 $V_H$ | EVQLVQSGAEVKKPGESLKISCKGSGYSFITYWISWVRQMPGKGLEWMGAI DPSDSDARYSPSFQGQVTISADKSISTAYLQWSSLKASDTAMYYCAKSDPG YSGYSLLYGFDSWGQGTLVTVSS |
| 13 | Ab51-Ab60 $V_H$ | EVQLVQSGAEVKKPGESLKISCKISGYSFITYWISWVRQMPGKGLEWMGAI DPSDSDARYSPSFQGQVTISADKSISTAYLQWSSLKASDTAMYYCAKSDPG YSGYSLLYGFDSWGQGTLVTVSS |
| 14 | Ab1, 11, 21, 31, 41, 51 $V_L$ | DIVMTQTPLSSPVTLGQPASISCRSSQSLVQRNGNTYLSWLQQRPGQPPRLLI YQVSNRYSGVPDRFSGSGAGTDFTLKISRVEAEDVGVYYCGQGAHLPLTFG QGTKVEIK |
| 15 | Ab2, 12, 22, 32, 42, 52 $V_L$ | DIVMTQTPLSSPVTLGQPASISCRSSQSLVQRNGNTYLSWYQQRPGQPPRLLI YQVSNRYSGVPDRFSGSGAGTDFTLKISRVEAEDVGVYYCGQGAHLPLTFG QGTKVEIK |
| 16 | Ab3, 13, 23, 33, 43, 53 $V_L$ | DVVMTQSPLSLPVTLGQPASISCRSSQSLVQRNGNTYLSWFQQRPGQSPRLL IYQVSNRYSGVPDRFSGSGSGTDFTLKISRVEAEDVGVYYCGQGAHLPLTFG QGTKVEIK |
| 17 | Ab4, 14, 24, 34, 44, 54 $V_L$ | DVVMTQSPLSLPVTLGQPASISCRSSQSLVQRNGNTYLSWYQQRPGQSPRLL IYQVSNRYSGVPDRFSGSGSGTDFTLKISRVEAEDVGVYYCGQGAHLPLTFG QGTKVEIK |
| 18 | Ab5, 15, 25, 35, 45, 55 $V_L$ | DVVMTQSPLSLPVTLGQPASISCRSSQSLVQRNGNTYLSWYQQRPGQPPRLL IYQVSNRYSGVPDRFSGSGSGTDFTLKISRVEAEDVGVYYCGQGAHLPLTFG QGTKVEIK |
| 19 | Ab6, 16, 26, 36, 46, 56 $V_L$ | DVVMTQSPLSLPVTLGQPASISCRSSQSLVQRNGNTYLSWFQQRPGQPPRLL IYQVSNRYSGVPDRFSGSGSGTDFTLKISRVEAEDVGVYYCGQGAHLPLTFG QGTKVEIK |
| 20 | Ab7, 17, 27, 37, 47, 57 $V_L$ | DIVMTQSPLSLPVTLGQPASISCRSSQSLVQRNGNTYLSWFQQRPGQSPRLLI YQVSNRYSGVPDRFSGSGSGTDFTLKISRVEAEDVGVYYCGQGAHLPLTFG QGTKVEIK |
| 21 | Ab8, 18, 28, 38, 48, 58 $V_L$ | DIVMTQSPLSLPVTLGQPASISCRSSQSLVQRNGNTYLSWYQQRPGQSPRLLI YQVSNRYSGVPDRFSGSGSGTDFTLKISRVEAEDVGVYYCGQGAHLPLTFG QGTKVEIK |
| 22 | Ab9, 19, 29, 39, 49, 59 $V_L$ | DIVMTQSPLSLPVTLGQPASISCRSSQSLVQRNGNTYLSWYQQRPGQPPRLLI YQVSNRYSGVPDRFSGSGSGTDFTLKISRVEAEDVGVYYCGQGAHLPLTFG QGTKVEIK |
| 23 | Ab10, 20, 30, 40, 50, 60 $V_L$ | DIVMTQSPLSLPVTLGQPASISCRSSQSLVQRNGNTYLSWFQQRPGQPPRLLI YQVSNRYSGVPDRFSGSGSGTDFTLKISRVEAEDVGVYYCGQGAHLPLTFG QGTKVEIK |
| 24 | Ab61 $V_L$ | DVVMTQSPLSLPVTLGQPASISCRSSQSLVQRNANTYLSWYQQRPGQSPRLL IYQVSNRYSGVPDRFSGSGSGTDFTLKISRVEAEDVGVYYCGQGAHLPLTFG QGTKVEIK |
| 25 | IgG1 heavy chain constant region | ASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVK FNWYVDGVEVHNAKTKPREEQYNSTYRVVSVLTVLHQDWLNGKEYKCKV SNKALPAPIEKTISKAKGQPREPQVYTLPPSREEMTKNQVSLTCLVKGFYPS DIAVEWESNGQPENNYKTTPPVLDSDGSFFLYSKLTVDKSRWQQGNVFSCS VMHEALHNHYTQKSLSLSPGK |

TABLE 3-continued

Exemplary sequences.

| SEQ ID NO | Description | Sequence |
|---|---|---|
| 26 | IgG4 heavy chain constant region | ASTKGPSVFPLAPCSRSTSESTAALGCLVKDYFPEPVTVSWNSGALTSGVHT FPAVLQSSGLYSLSSVVTVPSSSLGTKTYTCNVDHKPSNTKVDKRVESKYGP PCPSCPAPEFLGGPSVFLFPPKPKDTLMISRTPEVTCVVVDVSQEDPEVQFN WYVDGVEVHNAKTKPREEQFNSTYRVVSVLTVLHQDWLNGKEYKCKVSN KGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVM HEALHNHYTQKSLSLSLGK |
| 27 | Light chain constant region | RTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFN RGEC |
| 28 | Human nerve growth factor (120 aa) | SSSHPIFHRGEFSVCDSVSVWVGDKTTATDIKGKEVMVLGEVNINNSVFKQ YFFETKCRDPNPVDSGCRGIDSKHWNSYCTTTHTFVKALTMDGKQAAWR FIRIDTACVCVLSRKAVRRA |
| 29 | Human nerve growth factor (118 aa) | SSSHPIFHRGEFSVCDSVSVWVGDKTTATDIKGKEVMVLGEVNINNSVFKQ YFFETKCRDPNPVDSGCRGIDSKHWNSYCTTTHTFVKALTMDGKQAAWR FIRIDTACVCVLSRKAVR |

Nerve Growth Factor

Nerve growth factor was first described by Rita Levi-Montalcini, who showed its importance in the development, differentiation, maturation, and preservation of the integrity of sympathetic and sensory neurons (Levi-Montalcini R, et al. Trends Neurosci (1996) 19:514-20). NGF is involved in modulating the sensitivity of peripheral nerve fibers to heat and pain in physiological and pathological events, such as genetic, metabolic (diabetes mellitus), and infectious neuropathies (Lewin G R, et al. Annu Rev Neurosci (1996) 19:289-317). Further supporting a relationship between NGF and leprosy, Scully and Otten and others by previous studies reported the involvement of NGF in sympathetic and sensory neuron apoptosis (Anand P, et al. Lancet (1994) 344:129-30; Scully J L, et al. Cell Biol Int (1995) 19:459-69; Ioannou M S, et al. Int J Mol Sci (2017) 18:599). NGF was also identified as a trophic agent for sympathetic and sensory neurons of the dorsal root ganglia (DRG) (Levi-Montalcini R, et al. Proc Natl Acad Sci USA 1956; 42:695-9). Further studies led to the discovery of a family of related growth factors, or neurotrophins, comprising brain-derived neurotrophic factor (BDNF), neurotrophin-3 (NTF3, also known as NT-3), and NTF4 (also known as NT-4) (Barde Y A, et al. EMBO J 1982; 1:549-53; Ernfors P, et al. Proc Natl Acad Sci USA 1990; 87:5454-8; Berkemeier L R, et al. Neuron 1991; 7:857-66). These proteins were subsequently determined to be essential for the development and maintenance of the mammalian nervous system.

Nerve growth factor is endogenously produced as pre-proNGF during development and into maturity by immune and nerve cells, as well as peripheral effector cells, such as keratinocytes, melanocytes, smooth muscle cells, fibroblasts, and Schwann cells (Sofroniew M V, et al. Annu Rev Neurosci (2001) 24:1217-81; Levi-Montalcini R, et al. Trends Neurosci (1996) 19:514-20; Lewin G R, et al. Annu Rev Neurosci (1996) 19:289-317). It is also synthesized in other organs, such as the gonads, thyroid, parathyroid, and exocrine glands (e.g., salivary glands) (Ioannou M S, et al. Int J Mol Sci (2017) 18:599; Vega J A, et al. J Anat (2003) 203:1-19). The expression and receptor binding affinity of NGF, as well as the duration and intensity of cellular events triggered by proNGF activation, determine its specific activity in effector cells or neurons (Ioannou M S, et al. Int J Mol Sci (2017) 18:599; Patapoutian A, et al. Curr Opin Neurobiol (2001) 11:272-80; Aloe L, et al. Curr Neuropharmacol (2015) 13:294-303).

As used herein, the term "nerve growth factor" and "NGF" refers to nerve growth factor and variants thereof that retain at least part of the biological activity of NGF. As used herein, NGF includes all mammalian species of native or modified sequence NGF, including but are not limited to human, canine, feline, equine, or bovine.

The amino acid sequence of an exemplary human NGF comprises or consists of the amino acid sequence of SEQ ID NO: 28 or SEQ ID NO: 29.

Nerve Growth Factor Receptor

The neurotrophins act through two types of cell surface receptor: the common 75 k Da neurotrophin receptor (NGFR; also known as p75NTR and TNFRSF16) and specific tyrosine kinase receptors (Trks or NTRKs) (Rodriguez-Tebar A, et al. Neuron 1990; 4:487-92; Martin-Zanca D, et al. Mol Cell Biol 1989; 9:24-33; Klein R, et al. EMBO J 1989; 8:3701-9; Lamballe F, et al. *Cell* 1991; 66:967-79). NGFR binds all neurotrophins with similar affinity. This receptor is a member of the TNF family of receptors and is a type I membrane protein containing a single transmembrane region. The extracellular portion comprises four cysteine-rich domains containing potential N- and O-linked glycoslyation sites; the intracellular section contains a cytoplasmic death domain, implicated in the induction of apoptosis. The second type of neurotrophin receptor, the Trk receptor, comprises a family of homologous proteins with specificity in their ligand binding. NGF binds preferentially to TrkA (NTRK1), BDNF and NT-4 bind to TrkB (NTRK2), and NT-3 binds to TrkC (NTRK3). The Trk receptors are approximately 140 kDa in size, each consisting of approximately 800 amino acids. Half of the total residues constitute the extracellular portion of the receptor; there are a single transmembrane region and a cytoplasmic domain that has tyrosine kinase activity. These kinase domains show approximately 87% homology among receptors at the amino acid level. Ligand binding to Trk receptors initiates receptor dimerization, closely followed by transphosphorylation of tyrosine residues in the kinase domain of each receptor.

These phosphorylation events allow interaction with downstream effectors of a series of intracellular signaling cascades, including the Ras mitogen-activated protein kinase (MAPK) pathway, the phosphatidylinositol-3-kinase (PI3K) pathway, and the recruitment of phospholipase Cγ (PLCγ), all of which lead to activation of gene expression and thereby promote neuronal survival and/or differentiation (Kaplan D R, et al. Curr Opin Neurobiol 2000; 10:381-91; Huang E J, et al. Annu Rev Biochem 2003; 72:609-42).

Full-Length Anti-NGF Antibody

The anti-NGF antibody in some embodiments is a full-length anti-NGF antibody. In some embodiments, the full-length anti-NGF antibody is an IgA, IgD, IgE, IgG, or IgM. In some embodiments, the full-length anti-NGF antibody comprises IgG constant domains, such as constant domains of any one of IgG1, IgG2, IgG3, and IgG4 including variants thereof. In some embodiments, the full-length anti-NGF antibody comprises a lambda light chain constant region. In some embodiments, the full-length anti-NGF antibody comprises a kappa light chain constant region. In some embodiments, the full-length anti-NGF antibody is a full-length human anti-NGF antibody. In some embodiments, the full-length anti-NGF antibody comprises an Fc sequence of a mouse immunoglobulin. In some embodiments, the full-length anti-NGF antibody comprises an Fc sequence that has been altered or otherwise changed so that it has enhanced antibody dependent cellular cytotoxicity (ADCC) or complement dependent cytotoxicity (CDC) effector function.

Thus, for example, in some embodiments, there is provided a full-length anti-NGF antibody comprising IgG1 constant domains, wherein the anti-NGF antibody specifically binds to NGF. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG2 constant domains, wherein the anti-NGF antibody specifically binds to NGF. In some embodiments, the IgG2 is human IgG2. In some embodiments, the light chain constant region comprises or consists of the amino acid sequence of SEQ ID NO: 27.

In some embodiments, there is provided a full-length anti-NGF antibody comprising IgG3 constant domains, wherein the anti-NGF antibody specifically binds to NGF. In some embodiments, the IgG3 is human IgG3. In some embodiments, the light chain constant region comprises or consists of the amino acid sequence of SEQ ID NO: 27.

In some embodiments, there is provided a full-length anti-NGF antibody comprising IgG4 constant domains, wherein the anti-NGF antibody specifically binds to NGF. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO: 26 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a) a heavy chain variable domain comprising an HC-CDR1 comprising the amino acid sequence of SEQ ID NO: 1, or a variant thereof comprising up to about 3 (such as about any of 1, 2, or 3) amino acid substitutions, an HC-CDR2 comprising the amino acid sequence of SEQ ID NO: 2, or a variant thereof comprising up to about 3 (such as about any of 1, 2, or 3) amino acid substitutions, and an HC-CDR3 comprising the amino acid sequence of SEQ ID NO: 3, or a variant thereof comprising up to about 3 (such as about any of 1, 2, or 3) amino acid substitutions; and b) a light chain variable domain comprising an LC-CDR1 comprising the amino acid sequence of SEQ ID NO: 4 or SEQ ID NO: 7, or a variant thereof comprising up to about 3 (such as about any of 1, 2, or 3) amino acid substitutions, an LC-CDR2 comprising the amino acid sequence of SEQ ID NO: 5, or a variant thereof comprising up to about 3 (such as about any of 1, 2, or 3) amino acid substitutions, and an LC-CDR3 comprising the amino acid sequence of SEQ ID NO: 6, or a variant thereof comprising up to about 3 (such as about any of 1, 2, or 3) amino acid substitutions. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG2 constant domains, wherein the anti-NGF antibody comprises a) a heavy chain variable domain comprising an HC-CDR1 comprising the amino acid sequence of SEQ ID NO: 1, or a variant thereof comprising up to about 3 (such as about any of 1, 2, or 3) amino acid substitutions, an HC-CDR2 comprising the amino acid sequence of SEQ ID NO: 2, or a variant thereof comprising up to about 3 (such as about any of 1, 2, or 3) amino acid substitutions, and an HC-CDR3 comprising the amino acid sequence of SEQ ID NO: 3, or a variant thereof comprising up to about 3 (such as about any of 1, 2, or 3) amino acid substitutions; and b) a light chain variable domain comprising an LC-CDR1 comprising the amino acid sequence of SEQ ID NO: 4 or SEQ ID NO: 7, or a variant thereof comprising up to about 3 (such as about any of 1, 2, or 3) amino acid substitutions, an LC-CDR2 comprising the amino acid sequence of SEQ ID NO: 5, or a variant thereof comprising up to about 3 (such as about any of 1, 2, or 3) amino acid substitutions, and an LC-CDR3 comprising the amino acid sequence of SEQ ID NO: 6, or a variant thereof comprising up to about 3 (such as about any of 1, 2, or 3) amino acid substitutions. In some embodiments, the IgG2 is human IgG2. In some embodiments, the light chain constant region comprises or consists of the amino acid sequence of SEQ ID NO: 27.

In some embodiments, there is provided a full-length anti-NGF antibody comprising IgG3 constant domains, wherein the anti-NGF antibody comprises a) a heavy chain variable domain comprising an HC-CDR1 comprising the amino acid sequence of SEQ ID NO: 1, or a variant thereof comprising up to about 3 (such as about any of 1, 2, or 3) amino acid substitutions, an HC-CDR2 comprising the amino acid sequence of SEQ ID NO: 2, or a variant thereof comprising up to about 3 (such as about any of 1, 2, or 3)

amino acid substitutions, and an HC-CDR3 comprising the amino acid sequence of SEQ ID NO: 3, or a variant thereof comprising up to about 3 (such as about any of 1, 2, or 3) amino acid substitutions; and b) a light chain variable domain comprising an LC-CDR1 comprising the amino acid sequence of SEQ ID NO: 4 or SEQ ID NO: 7, or a variant thereof comprising up to about 3 (such as about any of 1, 2, or 3) amino acid substitutions, an LC-CDR2 comprising the amino acid sequence of SEQ ID NO: 5, or a variant thereof comprising up to about 3 (such as about any of 1, 2, or 3) amino acid substitutions, and an LC-CDR3 comprising the amino acid sequence of SEQ ID NO:6, or a variant thereof comprising up to about 3 (such as about any of 1, 2, or 3) amino acid substitutions. In some embodiments, the IgG3 is human IgG3. In some embodiments, the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a) a heavy chain variable domain comprising an HC-CDR1 comprising the amino acid sequence of SEQ ID NO: 1, or a variant thereof comprising up to about 3 (such as about any of 1, 2, or 3) amino acid substitutions, an HC-CDR2 comprising the amino acid sequence of SEQ ID NO: 2, or a variant thereof comprising up to about 3 (such as about any of 1, 2, or 3) amino acid substitutions, and an HC-CDR3 comprising the amino acid sequence of SEQ ID NOs: 3, or a variant thereof comprising up to about 3 (such as about any of 1, 2, or 3) amino acid substitutions; and b) a light chain variable domain comprising an LC-CDR1 comprising the amino acid sequence of SEQ ID NO: 4 or SEQ ID NO: 7, or a variant thereof comprising up to about 3 (such as about any of 1, 2, or 3) amino acid substitutions, an LC-CDR2 comprising the amino acid sequence of SEQ ID NO: 5, or a variant thereof comprising up to about 3 (such as about any of 1, 2, or 3) amino acid substitutions, and an LC-CDR3 comprising the amino acid sequence of SEQ ID NO: 6, or a variant thereof comprising up to about 3 (such as about any of 1, 2, or 3) amino acid substitutions. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO: 26 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a) a heavy chain variable domain comprising an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3, or a variant thereof comprising up to about 3 (such as about any of 1, 2, or 3) amino acid substitutions in the HC-CDR sequences; and b) a light chain variable domain comprising an LC-CDR1 comprising the amino acid sequence of SEQ ID NO: 4 or SEQ ID NO: 7, an LC-CDR2 comprising the amino acid sequence of SEQ ID NO: 5, and an LC-CDR3 comprising the amino acid sequence of SEQ ID NO: 6, or a variant thereof comprising up to about 3 (such as about any of 1, 2, or 3) amino acid substitutions in the LC-CDR sequences. In some embodiments, the IgG1 is human IgG1. In some embodiments, the anti-NGF heavy chain constant region comprises or consists of the amino acid sequence of SEQ ID NO: 25. In some embodiments, the anti-NGF light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a) a heavy chain variable domain comprising an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3, or a variant thereof comprising up to about 3 (such as about any of 1, 2, or 3) amino acid substitutions in the HC-CDR sequences; and b) a light chain variable domain comprising an LC-CDR1 comprising the amino acid sequence of SEQ ID NO: 4 or SEQ ID NO: 7, an LC-CDR2 comprising the amino acid sequence of SEQ ID NO: 5, and an LC-CDR3 comprising the amino acid sequence of SEQ ID NO: 6, or a variant thereof comprising up to about 3 (such as about any of 1, 2, or 3) amino acid substitutions in the LC-CDR sequences. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO: 26 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a) a heavy chain variable domain comprising an HC-CDR1 comprising the amino acid sequence of SEQ ID NO: 1, an HC-CDR2 comprising the amino acid sequence of any one of SEQ ID NO: 2, and an HC-CDR3 comprising the amino acid sequence of SEQ ID NO: 3; and b) a light chain variable domain comprising an LC-CDR1 comprising the amino acid sequence of SEQ ID NO: 4 or SEQ ID NO: 7, an LC-CDR2 comprising the amino acid sequence of SEQ ID NO: 5, and an LC-CDR3 comprising the amino acid sequence of SEQ ID NO: 6. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a) a heavy chain variable domain comprising an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3; and b) a light chain variable domain comprising an LC-CDR1 comprising the amino acid sequence of SEQ ID NO: 4 or SEQ ID NO: 7, an LC-CDR2 comprising the amino acid sequence of SEQ ID NO: 5, and an LC-CDR3 comprising the amino acid sequence of SEQ ID NO: 6. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO: 26 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of any one of SEQ ID NOs: 8-13, or a variant thereof having at least about 90% (for example at least about any of 91%, 92%, 93%, 94%, 95%, 96%, 97%, 98%, or 99%) sequence identity, and a light chain variable domain comprising the amino acid sequence of any one of SEQ ID NOs: 14-24, or a variant thereof having at least about 90% (for example at least about any of 91%, 92%, 93%, 94%, 95%, 96%, 97%, 98%, or 99%) sequence identity. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG2 constant domains, wherein the anti-NGF antibody comprises a heavy chain variable domain comprising the amino acid sequence of any one of SEQ ID NOs: 8-13, or a variant thereof having at least about 90% (for example at least about any of 91%, 92%, 93%, 94%, 95%, 96%, 97%, 98%, or 99%) sequence identity, and a light chain variable domain comprising the amino acid sequence of any one of SEQ ID NOs: 14-24, or a variant thereof having at least about 90% (for example at least about any of 91%, 92%, 93%, 94%, 95%, 96%, 97%, 98%, or 99%) sequence identity. In some embodiments, the IgG2 is human IgG2. In some embodiments, the light chain constant region comprises or consists of the amino acid sequence of SEQ ID NO: 27.

In some embodiments, there is provided a full-length anti-NGF antibody comprising IgG3 constant domains, wherein the anti-NGF antibody comprises a heavy chain variable domain comprising the amino acid sequence of any one of SEQ ID NOs: 8-13, or a variant thereof having at least about 90% (for example at least about any of 91%, 92%, 93%, 94%, 95%, 96%, 97%, 98%, or 99%) sequence identity, and a light chain variable domain comprising the amino acid sequence of any one of SEQ ID NOs: 14-24, or a variant thereof having at least about 90% (for example at least about any of 91%, 92%, 93%, 94%, 95%, 96%, 97%, 98%, or 99%) sequence identity. In some embodiments, the IgG3 is human IgG3. In some embodiments, the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of any one of SEQ ID NOs: 8-13, or a variant thereof having at least about 90% (for example at least about any of 91%, 92%, 93%, 94%, 95%, 96%, 97%, 98%, or 99%) sequence identity, and a light chain variable domain comprising the amino acid sequence of any one of SEQ ID NOs: 14-24, or a variant thereof having at least about 90% (for example at least about any of 91%, 92%, 93%, 94%, 95%, 96%, 97%, 98%, or 99%) sequence identity. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO: 26 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of any one of SEQ ID NOs: 8-13, and a light chain variable domain comprising the amino acid sequence of any one of SEQ ID NOs: 14-24. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of any one of SEQ ID NOs: 8-13, and a light chain variable domain comprising the amino acid sequence of any one of SEQ ID NOs: 14-24. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO:26 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of SEQ ID NO: 8 and a light chain variable domain comprising the amino acid sequence of SEQ ID NO: 17. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of SEQ ID NO: 8 and a light chain variable domain comprising the amino acid sequence of SEQ ID NO: 19. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of SEQ ID NO: 8 and a light chain variable domain comprising the amino acid sequence of SEQ ID NO: 23. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of SEQ ID NO: 9 and a light chain variable domain comprising the amino acid sequence of SEQ ID NO: 19. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of SEQ ID NO: 11 and a light chain variable domain comprising the amino acid sequence of SEQ ID NO: 19. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of SEQ ID NO: 11 and a light chain variable domain comprising the amino acid sequence of SEQ ID NO: 20. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of SEQ ID NO: 12 and a light chain variable domain comprising the amino acid sequence of SEQ ID NO: 17. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of SEQ ID NO: 12 and a light chain variable domain comprising the amino acid sequence of SEQ ID NO: 19. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of SEQ ID NO: 12 and a light chain variable domain comprising the amino acid sequence of SEQ ID NO: 20. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of SEQ ID NO: 13 and a light chain variable domain comprising the amino acid sequence of SEQ ID NO: 17. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG1 constant domains, wherein the anti-NGF antibody comprises a heavy chain variable domain comprising the amino acid sequence of SEQ ID NO: 8 and a light chain variable domain comprising the amino acid sequence of SEQ ID NO: 24. In some embodiments, the IgG1 is human IgG1. In some embodiments, the heavy chain constant region comprises or consists of the amino acid sequence of SEQ ID NO: 25. In some embodiments, the light chain constant region comprises or consists of the amino acid sequence of SEQ ID NO: 27. In some embodiments, the heavy chain constant region comprises or consists of the amino acid sequence of SEQ ID NO: 25 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of SEQ ID NO: 8 and a light chain variable domain comprising the amino acid sequence of SEQ ID NO: 17. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO:26 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of SEQ ID NO: 8 and a light chain variable domain comprising the amino acid sequence of SEQ ID NO: 19. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO:26 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of SEQ ID NO: 8 and a light chain variable domain comprising the amino acid sequence of SEQ ID NO: 23. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO:26 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of SEQ ID NO: 9 and a light chain variable domain comprising the amino acid sequence of SEQ ID NO: 19. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO:26 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of SEQ ID NO: 11 and a light chain variable domain comprising the amino acid sequence of SEQ ID NO: 19. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO:26 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of SEQ ID NO: 11 and a light chain variable domain comprising the amino acid sequence of SEQ ID NO: 20. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO:26 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of SEQ ID NO: 12 and a light chain variable domain comprising the amino acid sequence of SEQ ID NO: 17. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO:26 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of SEQ ID NO: 12 and a light chain variable domain comprising the amino acid sequence of SEQ ID NO: 19. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO:26 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of SEQ ID NO: 12 and a light chain variable domain comprising the amino acid sequence of SEQ ID NO: 20. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO:26 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of SEQ ID NO: 13 and a light chain variable domain comprising the amino acid sequence of SEQ ID NO: 17. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO:26 and the light chain constant region comprises or consists of the amino acid sequence of SEQ ID NO: 27.

In some embodiments, there is provided a full-length anti-NGF antibody comprising IgG4 constant domains, wherein the anti-NGF antibody comprises a heavy chain variable domain comprising the amino acid sequence of SEQ ID NO: 8 and a light chain variable domain comprising the amino acid sequence of SEQ ID NO: 24. In some embodiments, the IgG4 is human IgG4. In some embodiments, the heavy chain constant region comprises or consists of the amino acid sequence of SEQ ID NO: 26. In some embodiments, the light chain constant region comprises or consists of the amino acid sequence of SEQ ID NO: 27. In some embodiments, the heavy chain constant region comprises or consists of the amino acid sequence of SEQ ID NO:26 and the light chain constant region comprises or consists of the amino acid sequence of SEQ ID NO: 27.

Binding Affinity

Binding affinity can be indicated by Kd, Koff, Kon, or Ka. The term "Koff", as used herein, is intended to refer to the off-rate constant for dissociation of an antibody from the antibody/antigen complex, as determined from a kinetic selection set up. The term "Kon", as used herein, is intended to refer to the on-rate constant for association of an antibody to the antigen to form the antibody/antigen complex. The term dissociation constant "Kd", as used herein, refers to the dissociation constant of a particular antibody-antigen interaction, and describes the concentration of antigen required to occupy one half of all of the antibody-binding domains present in a solution of antibody molecules at equilibrium, and is equal to Koff/Kon. The measurement of Kd presupposes that all binding agents are in solution. In the case where the antibody is tethered to a cell wall, e.g., in a yeast expression system, the corresponding equilibrium rate constant is expressed as EC50, which gives a good approximation of Kd. The affinity constant, Ka, is the inverse of the dissociation constant, Kd.

The dissociation constant (Kd) is used as an indicator showing affinity of antibody moieties to antigens. For example, easy analysis is possible by the Scatchard method using antibodies marked with a variety of marker agents, as well as by using Biacore (made by Amersham Biosciences), analysis of biomolecular interactions by surface plasmon resonance, according to the user's manual and attached kit. The Kd value that can be derived using these methods is expressed in units of M. An antibody that specifically binds to a target may have a Kd of, for example, $\leq 10^{-7}$ M, $\leq 10^{-8}$ M, $\leq 10^{-9}$ M, $\leq 10^{-10}$ M, $\leq 10^{-11}$ M, $\leq 10^{-12}$ M, or $\leq 10^{-13}$ M.

Binding specificity of the antibody can be determined experimentally by methods known in the art. Such methods comprise, but are not limited to, Western blots, ELISA-, RIA-, ECL-, IRMA-, EIA-, BIAcore-tests and peptide scans.

In some embodiments, the anti-NGF antibody specifically binds to a target NGF with a Kd of about $10^{-7}$M to about $10^{-13}$ M (such as about $10^{-7}$ M to about $10^{-13}$ M, about $10^{-8}$ M to about $10^{-13}$ M, about $10^{-9}$ M to about $10^{-13}$ M, or about $10^{-10}$ M to about $10^{-12}$ M). Thus in some embodiments, the Kd of the binding between the anti-NGF antibody and NGF, is about $10^{-7}$M to about $10^{-13}$ M, about $1\times10^{-7}$M to about $5\times10^{-13}$ M, about $10^{-7}$M to about $10^{-12}$ M, about $10^{-7}$M to about $10^{-11}$ M, about $10^{-7}$M to about $10^{-10}$ M, about $10^{-7}$M to about $10^{-9}$M, about $10^{-8}$ M to about $10^{-13}$ M, about $1\times10^{-8}$ M to about $5\times10^{-13}$ M, about $10^{-8}$ M to about $10^{-12}$ M, about $10^{-8}$ M to about $10^{-11}$ M, about $10^{-8}$ M to about $10^{-10}$ M, about $10^{-8}$ M to about $10^{-9}$M, about $5\times10^{-9}$ M to about $1\times10^{-13}$ M, about $5\times10^{-9}$ M to about $1\times10^{-12}$ M, about $5\times10^{-9}$ M to about $1\times10^{-11}$ M, about $5\times10^{-9}$ M to about $1\times10^{-10}$ M, about $10^{-9}$ M to about $10^{-13}$ M, about $10^{-9}$ M to about $10^{-12}$ M, about $10^{-9}$ M to about $10^{-11}$ M, about $10^{-9}$ M to about $10^{-10}$ M, about $5\times10^{-10}$ M to about $1\times10^{-13}$ M, about $5\times10^{-10}$ M to about $1\times10^{-12}$ M, about $5\times10^{-10}$ M to about $1\times10^{-11}$ M, about $10^{-10}$ M to about $10^{-13}$ M, about $1\times10^{-10}$ M to about $5\times10^{-13}$ M, about $1\times10^{-10}$ M to about $1\times10^{-12}$ M, about $1\times10^{-10}$ M to about $5\times10^{-12}$ M, about $1\times10^{-10}$ M to about $1\times10^{-11}$ M, about $10^{-11}$ M to about $10^{-13}$ M, about $1\times10^{-11}$ M to about $5\times10^{-13}$ M, about $10^{-11}$ M to about $10^{-12}$ M, or about $10^{-12}$ M to about $10^{-13}$ M. In some embodiments, the Kd of the binding between the anti-NGF antibody and a NGF is about $10^{-7}$ M to about $10^{-13}$ M.

In some embodiments, the Kd of the binding between the anti-NGF antibody and a non-target is more than the Kd of the binding between the anti-NGF antibody and the target, and is herein referred to in some embodiments as the binding affinity of the anti-NGF antibody to the target (e.g., NGF) is higher than that to a non-target. In some embodiments, the non-target is an antigen that is not NGF. In some embodiments, the Kd of the binding between the anti-NGF antibody (against NGF) and a non-NGF target can be at least about 10 times, such as about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the Kd of the binding between the anti-NGF antibody and a target NGF.

In some embodiments, the anti-NGF antibody binds to a non-target with a Kd of about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the non-target is an antigen that is not NGF. Thus in some embodiments, the Kd of the binding between the anti-NGF antibody and a non-NGF target is about $10^{-1}$ M to about $10^{-6}$ M, about $1\times10^{-1}$ M to about $5\times10^{-6}$ M, about $10^{-1}$ M to about $10^{-5}$ M, about $1\times10^{-1}$ M to about $5\times10^{-5}$ M, about $10^{-1}$ M to about $10^{-4}$ M, about $1\times10^{-1}$ M to about $5\times10^{-4}$ M, about $10^{-1}$ M to about $10^{-3}$ M, about $1\times10^{-1}$ M to about $5\times10^{-3}$ M, about $10^{-1}$ M to about $10^{-2}$ M, about $10^{-2}$ M to about $10^{-6}$ M, about $1\times10^{-2}$ M to about $5\times10^{-6}$ M, about $10^{-2}$ M to about $10^{-5}$ M, about $1\times10^{-2}$ M to about $5\times10^{-5}$ M, about $10^{-2}$ M to about $10^{-4}$ M, about $1\times10^{-2}$ M to about $5\times10^{-4}$ M, about $10^{-2}$ M to about $10^{-3}$ M, about $10^{-3}$ M to about $10^{-6}$ M, about $1\times10^{-3}$ M to about $5\times10^{-6}$ M, about $10^{-3}$ M to about $10^{-5}$ M, about $1\times10^{-3}$ M to about $5\times10^{-5}$ M, about $10^{-3}$ M to about $10^{-4}$ M, about $10^{-4}$ M to about $10^{-6}$ M, about $1\times10^{-4}$ M to about $5\times10^{-6}$ M, about $10^{-4}$ M to about $10^{-5}$ M, or about $10^{-5}$ M to about $10^{-6}$ M.

In some embodiments, when referring to that the anti-NGF antibody specifically recognizes a target NGF at a high binding affinity, and binds to a non-target at a low binding affinity, the anti-NGF antibody will bind to the target NGF with a Kd of about $10^{-7}$ M to about $10^{-13}$ M (such as about $10^{-7}$ M to about $10^{-13}$ M, about $10^{-8}$ M to about $10^{-13}$ M, about $10^{-9}$ M to about $10^{-13}$ M, or about $10^{-10}$ M to about $10^{-12}$ M), and will bind to the non-target with a Kd of about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M).

In some embodiments, when referring to that the anti-NGF antibody specifically recognizes NGF, the binding affinity of the anti-NGF antibody is compared to that of a control anti-NGF antibody (such as Tanezumab). In some embodiments, the Kd of the binding between the control anti-NGF antibody and NGF can be at least about 2 times, such as about 2 times, about 3 times, about 4 times, about 5 times, about 6 times, about 7 times, about 8 times, about 9 times, about 10 times, about 10-100 times, about 100-1000 times, about $10^3$-$10^4$ times of the Kd of the binding between the anti-NGF antibody described herein and NGF.

Nucleic Acids

Nucleic acid molecules encoding the anti-NGF antibodies are also contemplated. In some embodiments, there is provided a nucleic acid (or a set of nucleic acids) encoding a full-length anti-NGF antibody, including any of the full-length anti-NGF antibodies described herein. In some embodiments, the nucleic acid (or a set of nucleic acids) encoding the anti-NGF antibody described herein may further comprises a nucleic acid sequence encoding a peptide tag (such as protein purification tag, e.g., His-tag, HA tag).

Also contemplated here are isolated host cells comprising an anti-NGF antibody, an isolated nucleic acid encoding the polypeptide components of the anti-NGF antibody, or a vector comprising a nucleic acid encoding the polypeptide components of the anti-NGF antibody described herein.

The present application also includes variants to these nucleic acid sequences. For example, the variants include nucleotide sequences that hybridize to the nucleic acid sequences encoding the anti-NGF antibodies of the present application under at least moderately stringent hybridization conditions.

The present application also provides vectors in which a nucleic acid of the present application is inserted.

In brief summary, the expression of an anti-NGF antibody (e.g., full-length anti-NGF antibody) by a natural or synthetic nucleic acid encoding the anti-NGF antibody can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequences.

The nucleic acids of the present application may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the application provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Green and Sambrook (2013, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-la (EGF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the application should not be limited to the use of constitutive promoters. Inducible promoters are also contemplated as part of the application. The use of an inducible promoter provides a molecular switch capable of turning on expression of the polynucleotide sequence to which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the expression of the anti-NGF antibody is inducible. In some embodiments, a nucleic acid sequence encoding the anti-NGF antibody is operably linked to an inducible promoter, including any inducible promoter described herein.

Inducible Promoters

The use of an inducible promoter provides a molecular switch capable of turning on expression of the polynucleotide sequence which it is operatively linked when such expression is desired, or turning off the expression when expression is not desired. Exemplary inducible promoter systems for use in eukaryotic cells include, but are not limited to, hormone-regulated elements (e.g., see Mader, S. and White, J. H. (1993) Proc. Natl. Acad. Sci. USA 90:5603-5607), synthetic ligand-regulated elements (see, e.g., Spencer, D. M. et al 1993) Science 262:1019-1024) and ionizing radiation-regulated elements (e.g., see Manome, Y. et al. (1993) Biochemistry 32:10607-10613; Datta, R. et al. (1992) Proc. Natl. Acad. Sci. USA 89:1014-10153). Further exemplary inducible promoter systems for use in in vitro or in vivo mammalian systems are reviewed in Gingrich et al. (1998) Annual Rev. Neurosci 21:377-405. In some embodiments, the inducible promoter system for use to express the anti-NGF antibody is the Tet system. In some embodiments, the inducible promoter system for use to express the anti-NGF antibody is the lac repressor system from *E. coli.*

An exemplary inducible promoter system for use in the present application is the Tet system. Such systems are based on the Tet system described by Gossen et al. (1993). In an exemplary embodiment, a polynucleotide of interest is under the control of a promoter that comprises one or more Tet operator (TetO) sites. In the inactive state, Tet repressor (TetR) will bind to the TetO sites and repress transcription from the promoter. In the active state, e.g., in the presence of an inducing agent such as tetracycline (Tc), anhydrotetracycline, doxycycline (Dox), or an active analog thereof, the inducing agent causes release of TetR from TetO, thereby allowing transcription to take place. Doxycycline is a member of the tetracycline family of antibiotics having the chemical name of 1-dimethylamino-2,4a,5,7,12-pentahydroxy-11-methyl-4,6-dioxo-1,4a,11,11a,12,12a-hexahydrotetracene-3-carboxamide.

In one embodiment, a TetR is codon-optimized for expression in mammalian cells, e.g., murine or human cells. Most amino acids are encoded by more than one codon due to the degeneracy of the genetic code, allowing for substantial variations in the nucleotide sequence of a given nucleic acid without any alteration in the amino acid sequence encoded by the nucleic acid. However, many organisms display differences in codon usage, also known as "codon bias" (i.e., bias for use of a particular codon(s) for a given amino acid). Codon bias often correlates with the presence of a predominant species of tRNA for a particular codon, which in turn increases efficiency of mRNA translation. Accordingly, a coding sequence derived from a particular organism (e.g., a prokaryote) may be tailored for improved expression in a different organism (e.g., a eukaryote) through codon optimization.

Other specific variations of the Tet system include the following "Tet-Off" and "Tet-On" systems. In the Tet-Off system, transcription is inactive in the presence of Tc or Dox. In that system, a tetracycline-controlled transactivator protein (tTA), which is composed of TetR fused to the strong transactivating domain of VP16 from Herpes simplex virus, regulates expression of a target nucleic acid that is under transcriptional control of a tetracycline-responsive promoter element (TRE). The TRE is made up of TetO sequence concatamers fused to a promoter (commonly the minimal promoter sequence derived from the human cytomegalovirus (hCMV) immediate-early promoter). In the absence of Tc or Dox, tTA binds to the TRE and activates transcription of the target gene. In the presence of Tc or Dox, tTA cannot bind to the TRE, and expression from the target gene remains inactive.

Conversely, in the Tet-On system, transcription is active in the presence of Tc or Dox. The Tet-On system is based on a reverse tetracycline-controlled transactivator, rtTA. Like tTA, rtTA is a fusion protein comprised of the TetR repressor and the VP16 transactivation domain. However, a four amino acid change in the TetR DNA binding moiety alters rtTA's binding characteristics such that it can only recognize the tetO sequences in the TRE of the target transgene in the presence of Dox. Thus, in the Tet-On system, transcription of the TRE-regulated target gene is stimulated by rtTA only in the presence of Dox.

Another inducible promoter system is the lac repressor system from *E. coli* (See Brown et al., Cell 49:603-612 (1987)). The lac repressor system functions by regulating transcription of a polynucleotide of interest operably linked to a promoter comprising the lac operator (lacO). The lac repressor (lacR) binds to LacO, thus preventing transcription of the polynucleotide of interest. Expression of the polynucleotide of interest is induced by a suitable inducing agent, e.g., isopropyl-β-D-thiogalactopyranoside (IPTG).

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 *FEBS Letters* 479:79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, there is provided nucleic acid encoding a full-length anti-NGF antibody according to any of the full-length anti-NGF antibodies described herein. In some embodiments, the nucleic acid comprises one or more nucleic acid sequences encoding the heavy and light chains of the full-length anti-NGF antibody. In some embodiments, each of the one or more nucleic acid sequences are contained in separate vectors. In some embodiments, at least some of the nucleic acid sequences are contained in the same vector. In some embodiments, all of the nucleic acid sequences are contained in the same vector. Vectors may be selected, for example, from the group consisting of mammalian expression vectors and viral vectors (such as those derived from retroviruses, adenoviruses, adeno-associated viruses, herpes viruses, and lentiviruses).

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Green and Sambrook (2013, Molecular Cloning:

A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method of inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present application, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the application.

Preparation of Anti-NGF Antibodies

In some embodiments, the anti-NGF antibody is a monoclonal antibody or derived from a monoclonal antibody. In some embodiments, the anti-NGF antibody comprises $V_H$ and $V_L$ domains, or variants thereof, from the monoclonal antibody. In some embodiments, the anti-NGF antibody further comprises $C_H1$ and $C_L$ domains, or variants thereof, from the monoclonal antibody. Monoclonal antibodies can be prepared, e.g., using known methods in the art, including hybridoma methods, phage display methods, or using recombinant DNA methods. Additionally, exemplary phage display methods are described herein and in the Examples below.

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of human monoclonal antibodies.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones can be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In some embodiments, according to any of the anti-NGF antibodies described herein, the anti-NGF antibody comprises sequences from a clone selected from an antibody library (such as a phage library or yeast library presenting scFv or Fab fragments). The following general methods can be used to generate antibody display library. Libraries were generated by PCR cassette mutagenesis with degenerate oligonucleotides as described in Kay et al. (1996), Phage display of peptides and proteins: a laboratory manual, *San Diego*, Academic Press (see, pages pg 277-291). The doping codon NNK was used to randomize one amino acid position to include 20 possible amino acids. To randomize one amino acid position to include only a subset of amino acids with specific properties, doping codons were used as described in Balint et al, (1993) Gene 137(1):109-18). Site directed mutagenesis was performed using recombinant PCR as described in Innis et al, (1990) PCR protocols: A guide to methods and applications (see, pp. 177-183). The clone may be identified by screening combinatorial libraries for antibody fragments with the desired activity or activities. For example, a variety of methods are known in the art for generating phage display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N.J., 2001) and further described, e.g., in McCafferty et al., *Nature* 348:552-554; Clackson et al., *Nature* 352: 624-628 (1991); Marks et al., *J. Mol. Biol.* 222:581-597 (1992); Marks and Bradbury, *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); *Fellouse, Proc. Natl. Acad. Sci. USA* 101(34): 12467-12472 (2004); and Lee et al., *J. Immunol. Methods* 284(1-2): 119-132 (2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12:433-455 (1994). Phage typically display antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12:725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227:381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

The anti-NGF antibodies can be prepared using phage display to screen libraries for anti-NGF antibody moieties specific to the target NGF. The library can be a human scFv phage display library having a diversity of at least one$\times10^9$ (such as at least about any of $1\times10^9$, $2.5\times10^9$, $5\times10^9$, $7.5\times10^9$, $1\times10^{10}$, $2.5\times10^{10}$, $5\times10^{10}$, $7.5\times10^{10}$, or $1\times10^{11}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al., *Nat. Biotechnol.* 23 (3): 344-348, 2005). In some embodiments, the heavy chain CDR3 of the semi-synthetic human library has a length from about 5 to about 24 (such as about any of 5, 6, 7, 8, 9, 10, 11, 12, 13, 14, 15, 16, 17, 18, 19, 20, 21, 22, 23, or 24) amino acids. In some embodiments, the library is a fully-synthetic phage display library. In some embodiments, the library is a non-human phage display library.

Phage clones that bind to the target NGF with high affinity can be selected by iterative binding of phage to the target NGF, which is bound to a solid support (such as, for example, beads for solution panning or mammalian cells for cell panning), followed by removal of non-bound phage and by elution of specifically bound phage. The bound phage clones are then eluted and used to infect an appropriate host cell, such as *E. coli* XL1-Blue, for expression and purification. The panning can be performed for multiple (such as about any of 2, 3, 4, 5, 6 or more) rounds with solution panning, cell panning, or a combination of both, to enrich for phage clones binding specifically to the target NGF. Enriched phage clones can be tested for specific binding to the target NGF by any methods known in the art, including for example ELISA and FACS.

An alternative method for screening antibody libraries is to display the protein on the surface of yeast cells. Wittrup et al. (U.S. Pat. Nos. 6,699,658 and 6,696,251) have developed a method for a yeast cell display library. In this yeast display system, a component involves the yeast agglutinin protein (Aga1), which is anchored to the yeast cell wall. Another component involves a second subunit of the agglutinin protein Aga2, which can display on the surface yeast cells through disulfide bonds to Aga1 protein. The protein Aga1 is expressed from a yeast chromosome after the Aga1 gene integration. A library of single chain variable fragments (scFv) is fused genetically to Aga2 sequence in the yeast display plasmid, which, after transformation, is maintained in yeast episomally with a nutritional marker. Both of the Aga1 and Aga2 proteins were expressed under the control of the galactose-inducible promoter.

Human antibody V gene repertoire (VH and VK fragments) are obtained by PCR method using a pool of degenerate primers (Sblattero, D. & Bradbury, A. Immunotechnology 3, 271-278 1998). The PCR templates are from the commercially available RNAs or CDNAs, including PBMC, spleen, lymph nodes, bone marrow and tonsils. Separate VH and VK PCR libraries were combined, then assembled together in the scFv format by overlap extension PCR (Sheets, M. D. et al. Proc. Natl. Acad. Sci. USA 95, 6157-6162 1998.). To construct the yeast scFv display library, the resultant scFv PCR products are cloned into the yeast display plasmid in the yeasts by homologous recombination. (Chao, G, et al, Nat Protoc. 2006; 1 (2): 755-68. Miller K D, et al. Current Protocols in Cytometry 4.7.1-4.7.30, 2008).

The anti-NGF antibodies can be discovered using mammalian cell display systems in which antibody moieties are displayed on the cell surface and those specific to the target NGF are isolated by the antigen-guided screening method, as described in U.S. Pat. No. 7,732,195B2. A Chinese hamster ovary (CHO) cell library representing a large set of human IgG antibody genes can be established and used to discover the clones expressing high-affinity antibody genes. Another display system has been developed to enable simultaneous high-level cell surface display and secretion of the same protein through alternate splicing, where the displayed protein phenotype remains linked to genotype, allowing soluble secreted antibody to be simultaneously characterized in biophysical and cell-based functional assays. This approach overcomes many limitations of previous mammalian cell display, enabling direct selection and maturation of antibodies in the form of full-length, glycosylated IgGs (Peter M. Bowers, et al, Methods 2014, 65:44-56). Transient expression systems are suitable for a single round of antigen selection before recovery of the antibody genes and therefore most useful for the selection of antibodies from smaller libraries. Stable episomal vectors offer an attractive alternative. Episomal vectors can be transfected at high efficiency and stably maintained at low copy number, permitting multiple rounds of panning and the resolution of more complex antibody libraries.

The IgG library is based on germline sequence V-gene segments joined to rearranged (D) J regions isolated from a panel of human donors. RNA collected from 2000 human blood samples was reverse-transcribed into cDNA, and the $V_H$ and $V_K$ fragments were amplified using $V_H$- and $V_K$-specific primers and purified by gel extraction. IgG libraries were generated by sub-cloning the $V_H$ and $V_K$ fragments into the display vectors containing IgG1 or K constant regions respectively and then electroporating into or transducing 293T cells. To generate the scFv antibody display library, scFvs were generated by linking VH and VK, and then sub-cloned into the display vector, which were then electroporated into or transduce 293T cells. As we known, the IgG library is based on germline sequence V-gene segments joined to rearranged (D)J regions isolated from a panel of donors, the donor can be a mouse, rat, rabbit, or monkey.

Monoclonal antibodies can also be made by recombinant DNA methods, such as those described in U.S. Pat. No. 4,816,567. DNA encoding the monoclonal antibodies of the application can be readily isolated and sequenced using conventional procedures (e.g., by using oligonucleotide probes that are capable of binding specifically to genes encoding the heavy and light chains of murine antibodies). Hybridoma cells as described above or NGF-specific phage clones of the application or other source of the NGF-specific clones can serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains and/or framework regions in place of the homologous non-human sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the application, or can be substituted for the variable domains of one antigen-combining site of an antibody of the application to create a chimeric bivalent antibody.

The antibodies can be monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using any method known in the art.

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. In some embodiments, the first heavy-chain constant region (CH1) containing the site necessary for light-chain binding is present in at least one of the fusions. DNAs encoding the immunoglobulin heavy-chain fusions and, if desired, the immunoglobulin light chain, are inserted into separate expression vectors, and are co-transfected into a suitable host organism.

Human and Humanized Antibodies

The anti-NGF antibodies (e.g., full-length anti-NGF antibodies) can be humanized antibodies or human antibodies. Humanized forms of non-human (e.g., murine) antibody moieties are chimeric immunoglobulins, immunoglobulin chains, or fragments thereof (such as Fv, Fab, Fab', $F(ab')_2$, scFv, or other antigen-binding subsequences of antibodies) that typically contain minimal sequence derived from non-human immunoglobulin. Humanized antibody moieties include human immunoglobulins, immunoglobulin chains, or fragments thereof (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibody moieties can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence.

Generally, a humanized antibody has one or more amino acid residues introduced into it from a source that is non-human. These non-human amino acid residues are often referred to as "import" residues, which are typically taken from an "import" variable domain. According to some embodiments, humanization can be essentially performed following the method of Winter and co-workers (Jones et al., *Nature,* 321: 522-525 (1986); Riechmann et al., *Nature,* 332: 323-327 (1988); Verhoeyen et al., *Science,* 239: 1534-1536 (1988)), by substituting rodent CDRs or CDR sequences for the corresponding sequences of a human antibody. Accordingly, such "humanized" antibody moieties are antibody moieties (U.S. Pat. No. 4,816,567), wherein substantially less than an intact human variable domain has been substituted by the corresponding sequence from a non-human species. In practice, humanized antibody moieties are typically human antibody moieties in which some CDR residues and possibly some FR residues are substituted by residues from analogous sites in rodent antibodies.

As an alternative to humanization, human antibody moieties can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *PNAS USA,* 90:2551 (1993); Jakobovits et al., *Nature,* 362:255-258 (1993); Bruggemann et al., *Year in Immunol.,* 7:33 (1993); U.S. Pat. Nos. 5,545,806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and Marks et al., *Bio/Technology,* 10:779-783 (1992); Lonberg et al., *Nature,* 368:856-859 (1994); Morrison, *Nature,* 368:812-813 (1994); Fishwild et al., *Nature Biotechnology,* 14:845-851 (1996); Neuberger, *Nature Biotechnology,* 14:826 (1996); Lonberg and Huszar, *Intern. Rev. Immunol.,* 13:65-93 (1995).

Human antibodies may also be generated by in vitro activated B cells (see U.S. Pat. Nos. 5,567,610 and 5,229,275) or by using various techniques known in the art, including phage display libraries. Hoogenboom and Winter, *J. Mol. Biol.,* 227:381 (1991); Marks et al., *J. Mol. Biol.,* 222:581 (1991). The techniques of Cole et al. and Boerner et al. are also available for the preparation of human monoclonal antibodies. Cole et al., *Monoclonal Antibodies and Cancer Therapy, Alan R. Liss*, p. 77 (1985) and Boerner et al., *J. Immunol.,* 147(1): 86-95 (1991).

Anti-NGF Antibody Variants

In some embodiments, amino acid sequences of the anti-NGF antibodies variants (e.g., full-length anti-NGF antibody) provided herein are contemplated. For example, it may be desirable to improve the binding affinity and/or other biological properties of the antibody. Amino acid sequences of an antibody variants may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, anti-NGF antibody variants having one or more amino acid substitutions are provided. Sites of interest for substitutional mutagenesis include the HVRs and FRs. Amino acid substitutions may be introduced into an antibody of interest and the products screened for a desired activity, e.g., improved bioactivity, retained/improved antigen binding, decreased immunogenicity, or improved ADCC or CDC.

Conservative substitutions are shown in Table 4 below.

TABLE 4

CONSERVATIVE SUBSTITUTIONS

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:

a. hydrophobic: Norleucine, Met, Ala, Val, Leu, Ile;

b. neutral hydrophilic: Cys, Ser, Thr, Asn, Gln;

c. acidic: Asp, Glu;

d. basic: His, Lys, Arg;

e. residues that influence chain orientation: Gly, Pro;

f. aromatic: Trp, Tyr, Phe.

Non-conservative substitutions will entail exchanging a member of one of these classes for another class.

An exemplary substitutional variant is an affinity matured antibody, which may be conveniently generated, e.g., using phage display-based affinity maturation techniques. Briefly, one or more CDR residues are mutated and the variant antibody moieties displayed on phage or yeast and screened for a particular biological activity (e.g., bioactivity based on TF-1 cell proliferation assay or binding affinity). Alterations (e.g., substitutions) may be made in HVRs, e.g., to improve bioactivity based on TF-1 cell proliferation assay or antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant $V_H$ and $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001)).

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant $V_H$ and $V_L$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine, or glu) to determine whether the interaction of the antibody with antigen is affected. Further substitutions may be introduced at the amino acid locations to demonstrate functional sensitivity to the initial substitutions. Alternatively, or additionally, a crystal structure of an antigen-antibody complex can be determined to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Fc Region Variants

In some embodiments, one or more amino acid modifications may be introduced into the Fc region of an antibody (e.g., a full-length anti-NGF antibody or anti-NGF Fc fusion protein) provided herein, thereby generating an Fc region variant. In some embodiments, the Fc region variant has enhanced ADCC effector function, often related to binding to Fc receptors (FcRs). In some embodiments, the Fc region variant has decreased ADCC effector function. There are many examples of changes or mutations to Fc sequences that can alter effector function. For example, WO 00/42072 and Shields et al. *J Biol. Chem.* 9 (2): 6591-6604 (2001) describe antibody variants with improved or diminished binding to FcRs. The contents of those publications are specifically incorporated herein by reference.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., an anti-NGF antibody). The typical ADCC involves activation of NK cells by antibodies. An NK cell expresses CD16 which is an Fc receptor. This receptor recognizes, and binds to, the Fc portion of an antibody bound to the surface of a target cell. The most common Fc receptor on the surface of an NK cell is called CD16 or FcγRIII. Binding of the Fc receptor to the Fc region of an antibody results in NK cell activation, release of cytolytic granules and consequent target cell apoptosis. The contribution of ADCC to tumor cell killing can be measured with a specific test that uses NK-92 cells that have been transfected with a high-affinity FcR. Results are compared to wild-type NK-92 cells that do not express the FcR.

In some embodiments, the application contemplates an anti-NGF antibody variant (such as a full-length anti-NGF antibody variant) comprising an Fc region that possesses some but not all effector functions, which makes it a desirable candidate for applications in which the half-life of the anti-NGF antibody in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CYTOTOX 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., *Int'l. Immunol.* 18(12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, there is provided an anti-NGF antibody (such as a full-length anti-NGF antibody) variant comprising a variant Fc region comprising one or more amino acid substitutions which improve ADCC. In some embodiments, the variant Fc region comprises one or more amino acid substitutions which improve ADCC, wherein the substitutions are at positions 298, 333, and/or 334 of the variant Fc region (EU numbering of residues). In some embodiments, the anti-NGF antibody (e.g., full-length anti-NGF antibody) variant comprises the following amino acid substitution in its variant Fc region: S298A, E333A, and K334A.

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164:4178-4184 (2000).

In some embodiments, there is provided an anti-NGF antibody (such as a full-length anti-NGF antibody) variant comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-NGF antibodies (such as full-length anti-NGF antibodies) comprising any of the Fc variants described herein, or combinations thereof, are contemplated.

Glycosylation Variants

In some embodiments, an anti-NGF antibody (such as a full-length anti-NGF antibody) provided herein is altered to increase or decrease the extent to which the anti-NGF antibody is glycosylated. Addition or deletion of glycosylation sites to an anti-NGF antibody may be conveniently accomplished by altering the amino acid sequence of the anti-NGF antibody or polypeptide portion thereof such that one or more glycosylation sites is created or removed.

Wherein the anti-NGF antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-NGF antibody of the application may be made in order to create anti-NGF antibody variants with certain improved properties.

The N-glycans attached to the CH2 domain of Fc is heterogeneous. Antibodies or Fc fusion proteins generated in CHO cells are fucosylated by fucosyltransferase activity. See Shoji-Hosaka et al., J. Biochem. 2006, 140:777-83. Normally, a small percentage of naturally occurring afucosylated IgGs may be detected in human serum. N-glycosylation of the Fc is important for binding to FcγR; and afucosylation of the N-glycan increases Fc's binding capacity to FcγRIIIa. Increased FcγRIIIa binding can enhance ADCC, which can be advantageous in certain antibody therapeutic applications in which cytotoxicity is desirable.

In some embodiments, an enhanced effector function can be detrimental when Fc-mediated cytotoxicity is undesirable. In some embodiments, the Fc fragment or CH2 domain is not glycosylated. In some embodiments, the N-glycosylation site in the CH2 domain is mutated to prevent from glycosylation.

In some embodiments, anti-NGF antibody (such as a full-length anti-NGF antibody) variants are provided comprising an Fc region wherein a carbohydrate structure attached to the Fc region has reduced fucose or lacks fucose, which may improve ADCC function. Specifically, anti-NGF antibodies are contemplated herein that have reduced fucose relative to the amount of fucose on the same anti-NGF antibody produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In some embodiments, the anti-NGF antibody is one wherein less than about 50%, 40%, 30%, 20%, 10%, or 5% of the N-linked glycans thereon comprise fucose. For example, the amount of fucose in such an anti-NGF antibody may be from 1% to 80%, from 1% to 65%, from 5% to 65% or from 20% to 40%. In some embodiments, the anti-NGF antibody is one wherein none of the N-linked glycans thereon comprise fucose, i.e., wherein the anti-NGF antibody is completely without fucose, or has no fucose or is afucosylated. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such asa-1,6-fucosyltransferase gene, FUT8, knockout CHO cells (see, e.g., Yamane-Ohnuki et al. *Biotech. Bioeng.* 87:614 (2004); Kanda, Y. et al., *Biotechnol. Bioeng.,* 94(4): 680-688 (2006); and WO2003/085107).

Anti-NGF antibody (such as a full-length anti-NGF antibody) variants are further provided with bisected oligosaccharides, e.g., in which a biantennary oligosaccharide attached to the Fc region of the anti-NGF antibody is bisected by GlcNAc. Such anti-NGF antibody (such as a full-length anti-NGF antibody) variants may have reduced fucosylation and/or improved ADCC function. Examples of such antibody variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering,* 93(5): 851-861 (2006). Anti-NGF antibody (such as full-length anti-NGF antibody) variants with at least one galactose residue in the oligosaccharide attached to the Fc region are also provided. Such anti-NGF antibody variants may have improved CDC function. Such antibody variants are described, e.g., in WO 1997/30087 (Patel et al.); WO 1998/58964 (Raju, S.); and WO 1999/22764 (Raju, S.).

In some embodiments, the anti-NGF antibody (such as a full-length anti-NGF antibody) variants comprising an Fc region are capable of binding to an FcγRIII. In some embodiments, the anti-NGF antibody (such as a full-length anti-NGF antibody) variants comprising an Fc region have ADCC activity in the presence of human effector cells (e.g., T cell) or have increased ADCC activity in the presence of human effector cells compared to the otherwise same anti-NGF antibody (such as a full-length anti-NGF antibody) comprising a human wild-type IgG1Fc region.

Cysteine Engineered Variants

In some embodiments, it may be desirable to create cysteine engineered anti-NGF antibodies (such as a full-length anti-NGF antibody) in which one or more amino acid residues are substituted with cysteine residues. In some embodiments, the substituted residues occur at accessible sites of the anti-NGF antibody. By substituting those residues with cysteine, reactive thiol groups are thereby positioned at accessible sites of the anti-NGF antibody and may be used to conjugate the anti-NGF antibody to other moieties, such as drug moieties or linker-drug moieties, to create an anti-NGF immunoconjugate, as described further herein. Cysteine engineered anti-NGF antibodies (e.g., full-length anti-NGF antibodies) may be generated as described, e.g., in U.S. Pat. No. 7,521,541.

Derivatives

In some embodiments, an anti-NGF antibody (such as a full-length anti-NGF antibody) provided herein may be further modified to contain additional non-proteinaceous moieties that are known in the art and readily available. The moieties suitable for derivatization of the anti-NGF antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the anti-NGF antibody may vary, and if more than one polymer are attached, they can be the same or different molecules. In general, the number and/or type of polymers used for derivatization can be determined based on considerations including, but not limited to, the particular properties or functions of anti-NGF antibody to be improved, whether the anti-NGF antibody derivative will be used in a therapy under defined conditions, etc.

Pharmaceutical Compositions

Also provided herein are compositions (such as pharmaceutical compositions, also referred to herein as formulations) comprising any of the anti-NGF antibodies (such as a full-length anti-NGF antibody), nucleic acids encoding the antibodies, vectors comprising the nucleic acids encoding the antibodies, or host cells comprising the nucleic acids or vectors described herein. In some embodiments, there is provided a pharmaceutical composition comprising any one of the anti-NGF antibodies described herein and a pharmaceutically acceptable carrier.

Suitable formulations of the anti-NGF antibodies are obtained by mixing an anti-NGF antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be treated herein. Lipofectins or liposomes can be used to deliver the anti-NGF antibodies of this application into cells.

The formulation herein may also contain one or more active compounds in addition to the anti-NGF antibody (such as a full-length anti-NGF antibody) as necessary for the particular indication being treated, preferably those with complementary activities that do not adversely affect each other. For example, it may be desirable to further provide an anti-inflammatory drug, an opioid analgesic, or NSAIDs in addition to the anti-NGF antibody. Such molecules are suitably present in combination in amounts that are effective for the purpose intended. The effective amount of such other agents depends on the amount of anti-NGF antibody present in the formulation, the type of disease or disorder or treatment, and other factors discussed above. These are generally used in the same dosages and with administration routes as described herein or about from 1 to 99% of the heretofore employed dosages.

The anti-NGF antibodies (e.g., full-length anti-NGF antibodies) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Sustained-release preparations may be prepared.

Sustained-release preparations of the anti-NGF antibodies (e.g., full-length anti-NGF antibodies) can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D (−)-3-hydroxybutyric acid. While polymers such as ethylene-vinyl acetate and lactic acid-glycolic acid enable release of molecules for over 100 days, certain hydro gels release proteins for shorter time periods. When encapsulated antibody remain in the body for a long time, they can denature or aggregate as a result of exposure to moisture at 37 °C, resulting in a loss of biological activity and possible changes in immunogenicity. Rational strategies can be devised for stabilization of anti-NGF antibodies depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In some embodiments, the anti-NGF antibody (such as a full-length anti-NGF antibody) is formulated in a buffer comprising a citrate, NaCl, acetate, succinate, glycine, polysorbate 80 (Tween 80), or any combination of the foregoing.

The formulations to be used for in vivo administration must be sterile. This is readily accomplished by, e.g., filtration through sterile filtration membranes.

Methods of Treatment Using Anti-NGF Antibodies

The anti-NGF antibodies (e.g., full-length anti-NGF antibodies) and/or compositions of the application can be administered to individuals (e.g., mammals such as humans) to treat a disease and/or disorder associated with high expression levels of NGF, and disease and/or disorder with increased sensitivity to NGF and/or pathological conditions associated with endogenous NGF, including, but not limited to, acute pain, dental pain, pain from trauma, Surgical pain, pain resulting from amputation or abscess, causalgia, demyelinating diseases, trigeminal neuralgia, cancer, chronic alcoholism, stroke, thalamic pain syndrome, diabetes, acquired immune deficiency syndrome (AIDS), toxins and chemotherapy, general headache, migraine, cluster headache, mixed-vascular and nonvascular syndromes, tension headache, general inflammation, arthritis, rheumatic diseases, lupus, osteoarthritis, inflammatory bowel disorders, irritable bowel syndrome, inflammatory eye disorders, inflammatory or unstable bladder disorders, psoriasis, skin complaints with inflammatory components, Sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skinreactions, pruritis, vitiligo, general gastrointestinal disorders, colitis, gastric ulceration, duodenal ulcers, vasomotor or allergic rhinitis, or bronchial disorders, dysmenorrhoea, dyspepsia, gastroesophageal reflux, pancreatitis, and visceralgia. In some embodiments, the individual is human. The present application thus in some embodiments provides a method of treating a disease and/or disorder characterized by high NGF expression and/or abnormal NGF function (such as pain) in an individual comprising administering to the individual an effective amount of a composition (such as a pharmaceutical composition) comprising an anti-NGF antibody (e.g., a full-length anti-NGF antibody), such as any one of the anti-NGF antibodies (e.g., full-length anti-NGF antibodies) described herein.

In some embodiments, there is provided a method of treating an individual having a disease and/or disorder characterized by high NGF expression and/or abnormal NGF function (such as pain) comprising administering to the individual an effective amount of a composition comprising an anti-NGF antibody comprising: a $V_H$ comprising an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3, or a variant thereof comprising up to 5 amino acid substitutions; and a $V_L$ comprising an LC-CDR1 comprising the amino acid sequence of SEQ ID NO: 4 or SEQ ID NO: 7, an LC-CDR2 comprising the amino acid sequence of SEQ ID NO: 5, and an LC-CDR3 comprising the amino acid sequence of SEQ ID NO: 6, or a variant thereof comprising up to 5 amino acid substitutions.

In some embodiments, there is provided a method of treating an individual having a disease and/or disorder characterized by high NGF expression and/or abnormal NGF function (such as pain) comprising administering to the individual an effective amount of a pharmaceutical composition comprising an anti-NGF antibody (e.g., full-length anti-NGF antibody) comprising a heavy chain variable domain ($V_H$) comprising an HC-CDR1 comprising TYWIS (SEQ ID NO: 1); an HC-CDR2 comprising AID-PSDSDARYSPSFQG (SEQ ID NO: 2); and an HC-CDR3 comprising SDPGYSGYSLLYGFDS (SEQ ID NO: 3); and a $V_L$ comprising a LC-CDR1 comprising RSSQSLVQRNG-NTYLS (SEQ ID NO: 4) or RSSQSLVQRNANTYLS (SEQ ID NO: 7); a LC-CDR2 comprising QVSNRYS (SEQ ID NO: 5); and a LC-CDR3 comprising GQGAHLPLT (SEQ ID NO: 6).

In some embodiments, there is provided a method of treating an individual having a disease and/or disorder characterized by high NGF expression and/or abnormal NGF function (such as pain) comprising administering to the individual an effective amount of a composition comprising an anti-NGF antibody comprising a $V_H$ comprising the amino acid sequence of SEQ ID NOs: 8-13, or a variant thereof having at least about 90% sequence identity to the amino acid sequence of any one of SEQ ID NOs: 8-13, and a $V_L$ comprising the amino acid sequence of SEQ ID NOs: 14-24, or a variant thereof having at least about 90% sequence identity to the amino acid sequence of any one of SEQ ID NOs: 14-24.

In some embodiments, the anti-NGF antibody provided herein is a full-length anti-NGF antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 25. In some embodiments, the heavy chain constant region comprises or consists of the amino acid sequence of SEQ ID NO: 26. In some embodiments, the light chain constant region comprises or consists of the amino acid sequence of SEQ ID NO: 27.

In some embodiments, there is provided a method of treating an individual having a disease and/or disorder characterized by high NGF expression and/or abnormal NGF function (such as pain) comprising administering to the individual an effective amount of a composition comprising an anti-NGF antibody comprising a $V_H$ comprising the amino acid sequence of SEQ ID NO: 8 and a $V_L$ comprising the amino acid sequence of SEQ ID NO: 17. In some embodiments, the anti-NGF antibody provided herein is a full-length anti-NGF antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 25. In some embodiments, the heavy chain constant region comprises or consists of the amino acid sequence of SEQ ID NO: 26. In some embodiments, the light chain constant region comprises or consists of the amino acid sequence of SEQ ID NO: 27.

In some embodiments, the anti-NGF antibody provided herein comprises a $V_H$ comprising the amino acid sequence of SEQ ID NO: 8 and a $V_L$ comprising the amino acid sequence of SEQ ID NO: 19. In some embodiments, the anti-NGF antibody provided herein is a full-length anti-NGF antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 25. In some embodiments, the heavy chain constant region comprises or consists of the amino acid sequence of SEQ ID NO: 26. In some embodiments, the light chain constant region comprises or consists of the amino acid sequence of SEQ ID NO: 27.

In some embodiments, the anti-NGF antibody provided herein comprises a $V_H$ comprising the amino acid sequence of SEQ ID NO: 8 and a $V_L$ comprising the amino acid sequence of SEQ ID NO: 23. In some embodiments, the anti-NGF antibody provided herein is a full-length anti-NGF antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 25. In some embodiments, the heavy chain constant region comprises or consists of the amino acid sequence of SEQ ID NO: 26. In some embodiments, the light chain constant region comprises or consists of the amino acid sequence of SEQ ID NO: 27.

In some embodiments, the anti-NGF antibody provided herein comprises a $V_H$ comprising the amino acid sequence of SEQ ID NO: 9 and a $V_L$ comprising the amino acid sequence of SEQ ID NO: 19. In some embodiments, the anti-NGF antibody provided herein is a full-length anti-NGF antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 25. In some embodiments, the heavy chain constant region comprises or consists of the amino acid sequence of SEQ ID NO: 26. In some embodiments, the light chain constant region comprises or consists of the amino acid sequence of SEQ ID NO: 27.

In some embodiments, the anti-NGF antibody provided herein comprises a $V_H$ comprising the amino acid sequence of SEQ ID NO: 11 and a $V_L$ comprising the amino acid sequence of SEQ ID NO: 19. In some embodiments, the anti-NGF antibody provided herein is a full-length anti-NGF antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 25. In some embodiments, the heavy chain constant region comprises or consists of the amino acid sequence of SEQ ID NO: 26. In some embodiments, the light chain constant region comprises or consists of the amino acid sequence of SEQ ID NO: 27.

In some embodiments, the anti-NGF antibody provided herein comprises a $V_H$ comprising the amino acid sequence of SEQ ID NO: 11 and a $V_L$ comprising the amino acid sequence of SEQ ID NO: 20. In some embodiments, the anti-NGF antibody provided herein is a full-length anti-NGF antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 25. In some embodiments, the heavy chain constant region comprises or consists of the amino acid sequence of SEQ ID NO: 26. In some embodiments, the light chain constant region comprises or consists of the amino acid sequence of SEQ ID NO: 27.

In some embodiments, the anti-NGF antibody provided herein comprises a $V_H$ comprising the amino acid sequence of SEQ ID NO: 12 and a $V_L$ comprising the amino acid sequence of SEQ ID NO: 17. In some embodiments, the anti-NGF antibody provided herein is a full-length anti-NGF antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 25. In some embodiments, the heavy chain constant region comprises or consists of the amino acid sequence of SEQ ID NO: 26. In some embodiments, the light chain constant region comprises or consists of the amino acid sequence of SEQ ID NO: 27.

In some embodiments, the anti-NGF antibody provided herein comprises a $V_H$ comprising the amino acid sequence of SEQ ID NO: 12 and a $V_L$ comprising the amino acid sequence of SEQ ID NO: 19. In some embodiments, the anti-NGF antibody provided herein is a full-length anti-NGF antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 25. In some embodiments, the heavy chain constant region comprises or consists of the amino acid sequence of SEQ ID NO: 26. In some embodiments, the light chain constant region comprises or consists of the amino acid sequence of SEQ ID NO: 27.

In some embodiments, the anti-NGF antibody provided herein comprises a $V_H$ comprising the amino acid sequence of SEQ ID NO: 12 and a $V_L$ comprising the amino acid sequence of SEQ ID NO: 20. In some embodiments, the anti-NGF antibody provided herein is a full-length anti-NGF antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 25. In some embodiments, the heavy chain constant region comprises or consists of the amino acid sequence of SEQ ID NO: 26. In some embodiments, the light chain constant region comprises or consists of the amino acid sequence of SEQ ID NO: 27.

In some embodiments, the anti-NGF antibody provided herein comprises a $V_H$ comprising the amino acid sequence of SEQ ID NO: 13 and a $V_L$ comprising the amino acid sequence of SEQ ID NO: 17. In some embodiments, the anti-NGF antibody provided herein is a full-length anti-NGF antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 25. In some embodiments, the heavy chain constant region comprises or consists of the amino acid sequence of SEQ ID NO: 26. In some embodiments, the light chain constant region comprises or consists of the amino acid sequence of SEQ ID NO: 27.

In some embodiments, the anti-NGF antibody provided herein comprises a $V_H$ comprising the amino acid sequence of SEQ ID NO: 8 and a $V_L$ comprising the amino acid sequence of SEQ ID NO: 24. In some embodiments, the anti-NGF antibody provided herein is a full-length anti-NGF antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 25. In some embodiments, the heavy chain constant region comprises or consists of the amino acid sequence of SEQ ID NO: 26. In some embodiments, the light chain constant region comprises or consists of the amino acid sequence of SEQ ID NO: 27.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old). In some embodiments, the individual is diagnosed with or genetically prone to one or more of the diseases or disorders described herein (such as inflammatory condition, rheumatoid arthritis, post-surgical pain, rheumatoid arthritis pain, and osteoarthritis pain). In some embodiments, the individual has one or more risk factors associated with one or more diseases or disorders described herein.

The present application in some embodiments provides a method of delivering an anti-NGF antibody (such as any one of the anti-NGF antibodies described herein, e.g., an isolated anti-NGF antibody) to a cell expressing NGF on its surface in an individual, the method comprising administering to the individual a composition comprising the anti-NGF antibody.

Antibodies and polypeptides of the invention can be used in the detection, diagnosis and monitoring of a disease, condition, or disorder associated with altered or aberrant NGF expression (in some embodiments, increased or decreased NGF expression (relative to a normal sample), and/or inappropriate expression, such as presence of expression in tissue(s) and/or cell(s) that normally lack NGF expression, or absence of NGF expression in tissue(s) or cell(s) that normally possess NGF expression). The antibodies and polypeptides of the invention are further useful for detection of NGF expression, for example, in a disease associated with altered or aberrant sensitivity or responsiveness to NGF. In some embodiments, NGF expression is detected in a sample from an individual suspected of having a disease, disorder featuring or associated with an altered or aberrant sensitivity or responsiveness to NGF expression (e.g., a cancer in which NGF promotes growth and/or metastasis)

Many diagnostic methods for any disease exhibiting abnormal NGF expression and the clinical delineation of those diseases are known in the art. Such methods include, but are not limited to, e.g., immunohistochemistry, PCR, and fluorescent in situ hybridization (FISH).

In some embodiments, the anti-NGF antibodies (e.g., full-length anti-NGF antibodies) and/or compositions of the application are administered in combination with a second, third, or fourth agent (including, e.g., an anti-inflammatory drug, an opioid analgesic, or NSAIDs) to treat diseases or disorders involving abnormal NGF expression (e.g., rheumatoid arthritis pain, and osteoarthritis pain).

In some embodiments, diagnosis or assessment of rheumatoid arthritis pain is well-established in the art. Assessment may be performed based on measures known in the art, such as patient characterization of pain using various pain scales. See, e.g., Katz et al, Surg Clin North Am. (1999) 79 (2): 231-52; Caraceni et al JPain Symptom Manage (2002) 23(3): 239-55. There are also commonly used scales to measure disease state such as the American College of Rheumatology (ACR) (Felson, et al., Arthritis and Rheumatism (1993) 36(6): 729-740), the Health Assessment Questionnaire (HAQ) (Fries, et al., (1982) J. Rheumatol. 9:789-793), the Paulus Scale (Paulus, et al., Arthritis and Rheumatism (1990) 33:477-484), and the Arthritis Impact Measure Scale (AIMS) (Meenam, et al., Arthritis and Rheumatology (1982) 25:1048-1053). Anti-NGF antagonist antibody may be administered to an individual via any suitable route. Examples of different administration route are described herein.

In some embodiments, diagnosis or assessment of osteoarthritis pain is well-established in the art. Assessment may be performed based on measures known in the art, such as patient characterization of pain using various pain scales. See, e.g., Katz et al, Surg Clin North Am. (1999) 79 (2): 231-52; Caraceni et al. J Pain Symptom Manage (2002) 23(3): 239-55. For example, WOMAC Ambulation Pain Scale (including pain, stiffness, and physical function) and 100 mm Visual Analogue Scale (VAS) may be employed to assess pain and evaluate response to the treatment.

Dosing and Method of Administering the Anti-NGF Antibodies

The dose of the anti-NGF antibody (such as isolated anti-NGF antibody) compositions administered to an individual (such as a human) may vary with the particular composition, the mode of administration, and the type of disease being treated. In some embodiments, the amount of the composition (such as composition comprising isolated anti-NGF antibody) is effective to result in an objective response (such as a partial response or a complete response) in the treatment of pain. In some embodiments, the amount of the anti-NGF antibody composition is sufficient to result in a complete response in the individual. In some embodiments, the amount of the anti-NGF antibody composition is sufficient to result in a partial response in the individual. In some embodiments, the amount of the anti-NGF antibody composition administered (for example when administered alone) is sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the anti-NGF antibody composition. Responses of an individual to the treatment of the methods described herein can be determined, for example, based on a reduction of pain score.

In some embodiments, the amount of the composition (such as composition comprising isolated anti-NGF antibody) is sufficient to reduce the intensity of pain. In some embodiments, the amount of the composition is sufficient to prolong overall survival of the individual. In some embodiments, the amount of the composition (for example when administered along) is sufficient to produce clinical benefit of more than about any of 50%, 60%, 70%, or 77% among a population of individuals treated with the anti-NGF antibody composition.

In some embodiments, the amount of the composition (such as composition comprising isolated anti-NGF antibody), alone or in combination with a second, third, and/or fourth agent, is an amount sufficient to reduce the intensity of pain by at least about any of 10%, 20%, 30%, 40%, 50%, 60%, 70%, 80%, 90%, 95% or 100% compared to the prior treatment in the same subject or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of the anti-NGF antibody (such as a full-length anti-NGF antibody) in the composition is below the level that induces a toxicological effect (i.e., an effect above a clinically acceptable level of toxicity) or is at a level where a potential side effect can be controlled or tolerated when the composition is administered to the individual.

In some embodiments, the amount of the composition is close to a maximum tolerated dose (MTD) of the composition following the same dosing regimen. In some embodiments, the amount of the composition is more than about any of 80%, 90%, 95%, or 98% of the MTD.

In some embodiments, the amount of an anti-NGF antibody (such as a full-length anti-NGF antibody) in the composition is included in a range of about 0.001 μg to about 1000 μg.

In some embodiments of any of the above aspects, the effective amount of anti-NGF antibody (such as a full-length anti-NGF antibody) in the composition is in the range of about 0.1 μg/kg to about 100 mg/kg of total body weight.

The anti-NGF antibody compositions can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal or transdermal. In some embodiments, sustained continuous release formulation of the composition may be used. In some embodiments, the composition is administered intravenously. In some embodiments, the composition is administered intraportally. In some embodiments, the composition is administered intraarterially. In some embodiments, the composition is administered intraperitoneally. In some embodiments, the composition is administered intrahepatically. In some embodiments, the composition is administered by hepatic arterial infusion. In some embodiments, the administration is to an injection site distal to a first disease site.

Articles of Manufacture and Kits

In some embodiments of the application, there is provided an article of manufacture containing materials useful for the treatment of an individual with pain or inflammatory conditions characterized by high NGF expression and/or abnormal NGF function (e.g., rheumatoid arthritis, post-surgical pain, rheumatoid arthritis pain, and osteoarthritis pain), or for delivering an anti-NGF antibody (such as a full-length anti-NGF antibody) to a cell expressing NGF on its surface. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is an anti-NGF antibody of the application. The label or package insert indicates that the composition is used for treating the particular condition. The label or package insert will further comprise instructions for administering the anti-NGF antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating an individual with pain or inflammatory conditions (e.g., rheumatoid arthritis, post-surgical pain, rheumatoid arthritis pain or osteoarthritis pain). In some embodiments, the package insert indicates that the composition is used for treating pain (e.g. rheumatoid arthritis pain).

Additionally, the article of manufacture may further comprise a second container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

Kits are also provided that are useful for various purposes, e.g., for treatment of an inflammatory condition or disease characterized by high NGF expression and/or abnormal NGF function (e.g., rheumatoid arthritis, post-surgical pain, rheumatoid arthritis pain, and osteoarthritis pain), or for delivering an anti-NGF antibody (such as a full-length anti-NGF antibody) to a cell expressing NGF on its surface, optionally in combination with the articles of manufacture. Kits of the application include one or more containers comprising anti-NGF antibody composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the application are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an anti-NGF antibody (such as a full-length anti-NGF antibody). In some embodiments, the kit comprises a) a composition comprising any one of the anti-NGF antibodies described herein, and b) an effective amount of at least one other agent, wherein the other agent enhances the effect (e.g., treatment effect, detecting effect) of the anti-NGF antibody. In some embodiments, the kit comprises a) a composition comprising any one of the anti-NGF antibodies described herein, and b) instructions for administering the anti-NGF antibody composition to an individual for treatment of an individual with pain or inflammatory conditions characterized by high NGF expression and/or abnormal NGF function (e.g., rheumatoid arthritis, post-surgical pain, rheumatoid arthritis pain, and osteoarthritis pain). In some embodiments, the kit comprises a) a composition comprising any one of the anti-NGF antibodies described herein, b) an effective amount of at least one other agent, wherein the other agent enhances the effect (e.g., treatment effect, detecting effect) of the anti-NGF antibody, and c) instructions for administering the anti-NGF antibody composition and the other agent(s) to an individual for treatment of an individual with pain or inflammatory conditions characterized by high NGF expression and/or abnormal NGF function (e.g., rheumatoid arthritis, post-surgical pain, rheumatoid arthritis pain, and osteoarthritis pain). The anti-NGF antibody and the other agent(s) can be present in separate containers or in a single container. For example, the kit may comprise one distinct composition or two or more compositions wherein one composition comprises an anti-NGF antibody and another composition comprises another agent.

In some embodiments, the kit comprises a nucleic acid (or a set of nucleic acids) encoding an anti-NGF antibody (such as a full-length anti-NGF antibody). In some embodiments, the kit comprises a) a nucleic acid (or set of nucleic acids) encoding an anti-NGF antibody, and b) a host cell for expressing the nucleic acid (or set of nucleic acids). In some embodiments, the kit comprises a) a nucleic acid (or set of nucleic acids) encoding an anti-NGF antibody, and b) instructions for i) expressing the anti-NGF antibody in a host cell, ii) preparing a composition comprising the anti-NGF antibody, and iii) administering the composition comprising the anti-NGF antibody to an individual for the treatment of an individual with pain or inflammatory conditions characterized by high NGF expression and/or abnormal NGF function (e.g., rheumatoid arthritis, post-surgical pain, rheumatoid arthritis pain, and osteoarthritis pain). In some embodiments, the kit comprises a) a nucleic acid (or a set of nucleic acids) encoding an anti-NGF antibody, b) a host cell for expressing the nucleic acid (or set of nucleic acids), and c) instructions for i) expressing the anti-NGF antibody in the host cell, ii) preparing a composition comprising the anti-NGF antibody, and iii) administering the composition comprising the anti-NGF antibody to an individual for the treatment of an individual with pain or inflammatory conditions characterized by high NGF expression and/or abnormal NGF function (e.g., rheumatoid arthritis, post-surgical pain, rheumatoid arthritis pain, and osteoarthritis pain).

The kits of the application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the anti-NGF antibody compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of an anti-NGF antibody (such as a full-length anti-NGF antibody) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the anti-NGF antibody and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this application. The application will now be described in greater detail by reference to the following non-limiting examples. The following examples further illustrate the application but, of course, should not be construed as in any way limiting its scope.

EXAMPLES

In the experimental disclosure which follows, the following abbreviations apply: NGF (Nerve growth factor).

Example 1: Generation of Recombinant Human and Mouse NGF and Selection of Anti-NGF scFv Antibodies Generation of Recombinant NGF-Fc Fusion Proteins The full-length sequence of human NGF gene or mouse NGF gene was synthesized (Generay, Shanghai) and subcloned into the expression vectors pTT5 containing human IgG1 Fc or IgG4 Fc gene using proper restriction enzyme recognition sites. Expression of these two human NGF-Fc fusion proteins were carried out according to manufacturer's protocol. Briefly, 293F cells were transfected with the expression vectors mixed with transfectant, and the cells were cultured at 37 °C, under 8% $CO_2$ and 120 rpm for 5 days. The culture media was collected and the NGF-Fc proteins were purified using protein A resin based on the protocol provided by manufacturer's guide. Briefly, Protein A column was first equilibrated with a PBS buffer containing 50 mM PBS and 0.15M NaCl (pH7.2), at a flow rate of 150 cm/h and with a volume that is 6 times the volume of the column. The supernatant of the culture media (pH was adjusted to 7.2) was passed through the column at the flow rate of 150 cm/h. Upon full equilibration, to the column 50 mM sodium citrate (pH3.5) was added and the elution containing NGF-Fc was collected.

Generation of Biotinylated NGF Antigen

Biotinylation of NGF-Fc fusion protein was carried out using EZ-Link™ NHS-PEG4-Biotin (ThermoFisher) according to the manufacturer's protocol. Briefly, the NHS-PEG4-biotin was mixed with the NGF-Fc protein by the ratio of 10:1 and incubated at 25 °C for 1 hour, followed by dialysis in PBS to remove the free NHS-PEG4-biotin. The biotinylated NGF-Fc protein is referred to as NGF-PEG4-biotin. The efficiency of biotinylation was measured using ELISA. Briefly, NGF-PEG4-biotin was serially diluted at a 1:2 ratio, from a starting concentration of 500 ng/mL, before being used to coat the ELISA plate. SA-HRP was used for signal detection and standard biotinylation products were used as control. The biotinylation efficiency was estimated to be more than 70%.

Selection of Anti-NGF scFv Antibodies

ScFvs specific to NGF were enriched and selected from the yeast surface display library of the company after several round of panning. The yeast surface display library was constructed with the size of diversity of greater than $10^{10}$. The library was enriched by NGF using magnetic-activated cell sorting (MACS) first. Briefly, after expansion, the scFv yeast library was induced in SGCAA culture media for 40-48 hours at 20 °C. 1 μM of PEG4-biotinylated NGF-Fc protein was used in the first round of panning. After incubation for an hour at 4 °C, the yeasts were centrifugated at 2500 g for 5 minutes to remove the unbound antigens and re-suspended in 10 ml PBSM per $10^9$ yeast. Magnetic Streptavidin beads were then added and mixed thoroughly. After 30 min incubation on ice, the yeasts were diluted by 5-10 times volume of PBSM and passed through the MACS LS column (Miltenyi Biotec). Bound cells were eluted and collected for culture and subsequent FACS sorting.

Selection of anti-NGF scFv antibodies using flow cytometry sorting: The yeasts enriched from the previous MACS panning were subjected to flow cytometry sorting. Briefly, the yeast cells induced by SGCAA media were pelleted and washed at 14,000 g for 30 seconds in 1 mL PBSM buffer. The yeasts were then resuspended in 100 μl PBSM buffer containing NGF-Fc and incubated at room temperature for an hour. After washing, the cells were stained with DyLight®-650-Goat anti-Human IgG-Fc (1:100 dilution) and FITC-anti-V5 (1:100 dilution) in 100 μL PBSM buffer by incubation on ice for 20 mins. The top 1% of double-positively stained cells were gated and sorted into culture media for cell expansion. The antigen-guided selection was repeated 2-3 cycles, with the antigen concentration reducing from 500 nM to 100 nM. Single colonies were assayed by further FACS analysis. For the high binders to NGF, scFv genes was obtained by PCR from the yeasts and re-formatted into full-length IgG1 constructs in mammalian expression vector. A panel of positive antibodies were obtained at the end of the selection process, and subjected to NGF binding ELISA assay and functional testing for the ability to inhibit human NGF binding to TrkA receptor and p75 receptor.

NGF binding ELISA assay: In human NGF binding ELISA, Corning 3366 high binding 96 well plates were coated with recombinantly produced human-NGF at 1 μg per ml, 50 μl/well in 1×PBS, and incubated overnight at 4 °C. The plates were washed and blocked with 250 μl of 1×PBS/1% BSA at least 30 minutes at room temperature. 50 μl of culture supernatants, after 1:1 diluted by the PBS/BSA diluent, or the purified antibodies diluted serially from a certain concentration with the diluent, were added per well, and incubated at 37 °C for 2 hours. After washing, a secondary antibody, goat anti-human IgG Fc AP (Southern biotech) was applied at a dilution of 1:3000 in PBS/BSA. The plates were incubated for 1 hour at RT and washed. After adding the PNPP substrate, the ODs at 405 nm were read.

TrkA inhibition ELISA assay: The TrkA inhibition ELISA assay was designed to identify the anti-NGF antibodies that have the capability of blocking NGF binding to its receptor TrkA. In this assay, human TrkA-Fc (IgG1-Fc, Sinobiological) was coated at 1 μg/ml in the 96-well plates and incubated overnight at 4 °C. Antibodies, from cell culture supernatants or after purified, in different dilutions, were pre-incubated with human NGF-Fc4 (IgG4-Fc) at a final concentration of 70 ng/mL for 2 hours in 37 °C. A total of 50 μl of the reaction mixtures were then transferred into the TrkA-Fc coated 96-well plates and incubated in room temperature for 2 hours. After washing, a secondary mouse anti-human IgG4-AP (Southern biotech) was added at a dilution of 1:1000 After one hour in room temperature, the plates were washed, and after adding PNPP substrate, ODs at 405 nm were read.

p75 inhibition ELISA assay: The p75 inhibition assay was designed to identify anti-NGF antibodies that were capable of inhibiting NGF binding to p75. In this assay, human p75-Fc (IgG1-Fc, Sinobiological) was coated at 1 μg/mL in the 96-well plates and incubated overnight at 4 °C. Anti-NGF antibodies, from supernatants directly or after purified, in different dilutions, were pre-incubated with human NGF-Fc4 (IgG4-Fc) at a final concentration of 350 ng/ml for 2 hours in 37 °C. A total of 50 μl of the reaction mixtures were then transferred into the p75-Fc coated 96-well plates and incubated in room temperature for 2 hrs. After washing, a secondary mouse anti-human IgG4-AP (Southern biotech) was added at a dilution of 1:1000. After 1 hour in room temperature, the plates were washed, and after adding PNPP substrate, ODs at 405 nm were read.

Example 2: Generation and Characterization of Full-Length Anti-NGF Antibodies Generation of Full-Length Anti-NGF Antibodies The most potent scFv antibodies were reformatted as human IgG1 antibody molecules with a human IgG1 heavy chain constant domain, and a human kappa light chain constant domain. $V_L$ and $V_H$ were amplified from the yeast expression vector and introduced into eukaryotic expression vectors pTT5-L (containing kappa constant domain) and pTT5-H1 (containing IgG1 heavy chain constant domain) separately. Plasmids containing the light or heavy chain genes were extracted and used to co-transfect 293F cells.

After the cells were cultured at 37 °C, 8% $CO_2$ and 120 rpm for 5 days, the culture media of the 293F cells was purified using Protein A affinity chromatography. Briefly, Protein A column was first equilibrated with a 50 mM PBS buffer containing 0.15M NaCl (pH7.2), at a flow rate of 150 cm/h and with a volume that is 6 times the volume of the column. The supernatant of the culture media (pH was adjusted to 7.2) was passed through the column at a flow rate of 150 cm/h. Upon further equilibration, the column was washed using 50 mM sodium citrate (pH3.5) and the elution containing anti-NGF antibodies was collected. Out of the full-length antibodies that were generated, Abl was selected as the lead antibody based on its functionalities in both NGF binding, TrkA and p75 inhibition activities (The method was described in example 1).

Optimization of the Lead Anti-NGF Antibody

A small scale of antibody expression was performed in Expi293™ Expression System (Thermo Fisher) by following the manual. The yield of Abl is 55.4 mg/L, as reported in the literature, the low expression yield was believed to be related with its poor biophysical property, because the protein aggregate appears as shown by SEC analysis (data not shown). To improve the developability of antibody, a framework re-engineering method was used, in which several mutants were introduced into the antibody framework region at the sites that might be responsible for the protein solubility or stability based on antibody structure analysis. In addition, the antibody frameworks from different VH or VK family with high homology to the parent framework were chosen for the same purpose. As a result, two frameworks for each VH or VK of the following antibodies were used for this antibody, i.e. human VH1-69*01 and VH5-51*01 for VH gene, and VK2-24*01 and VK2-30*01 for VK gene (www.IMGT.org). The expression level and NGF-binding EC50 of antibodies with different combinations of antibody frameworks and mutations were measured, the results of which are listed in the table 5. The Numbering is according to the EU index of Kabat.

TABLE 5

| Antibody | Yield(mg/L) | NGF binding EC50(ng/mL) |
|---|---|---|
| Ab1 | 55.4 | 0.01848 |
| Ab2 | 160.3 | 0.01967 |
| Ab3 | 35.8 | 0.01699 |
| Ab4 | 177.8 | 0.01239 |
| Ab5 | 207.6 | 0.01393 |
| Ab6 | 158.0 | 0.02101 |
| Ab7 | 77.7 | 0.00988 |
| Ab8 | 156.0 | 0.02047 |
| Ab9 | 198.5 | 0.08756 |
| Ab10 | 146.6 | 0.01343 |
| Ab11 | 57.5 | 0.03203 |
| Ab12 | 108.2 | 0.0365 |
| Ab13 | 34.0 | 0.04299 |
| Ab14 | 145.8 | 0.03512 |
| Ab15 | 157.6 | 0.04604 |
| Ab16 | 184.5 | 0.01731 |
| Ab17 | 208.7 | 0.01601 |
| Ab18 | 169.4 | 0.02714 |
| Ab19 | 157.5 | 0.03241 |
| Ab20 | 143.7 | 0.02152 |
| Ab21 | 65.2 | 0.04033 |
| Ab22 | 134.7 | 0.03822 |
| Ab23 | 42.5 | 0.04051 |
| Ab24 | 112.0 | 0.03995 |
| Ab25 | 199.8 | 0.03311 |
| Ab26 | 138.8 | 0.02338 |
| Ab27 | 150.2 | 0.02062 |
| Ab28 | 150.8 | 0.03309 |

TABLE 5-continued

| Antibody | Yield(mg/L) | NGF binding EC50(ng/mL) |
|---|---|---|
| Ab29 | 158.7 | 0.02916 |
| Ab30 | 112.8 | 0.02536 |
| Ab31 | 67.9 | 0.0502 |
| Ab32 | 110.8 | 0.04026 |
| Ab33 | 43.3 | 0.03425 |
| Ab34 | 202.1 | 0.1097 |
| Ab35 | 157.6 | 0.03081 |
| Ab36 | 168.4 | 0.02185 |
| Ab37 | 156.0 | 0.03168 |
| Ab38 | 165.8 | 0.02521 |
| Ab39 | 190.6 | 0.02082 |
| Ab40 | 179.1 | 0.01719 |
| Ab41 | 70.0 | 0.01925 |
| Ab42 | 106.1 | 0.01323 |
| Ab43 | 68.4 | 0.02214 |
| Ab44 | 111.3 | 0.01285 |
| Ab45 | 100.0 | 0.01664 |
| Ab46 | 110.9 | 0.01693 |
| Ab47 | 117.0 | 0.00942 |
| Ab48 | 115.3 | 0.01563 |
| Ab49 | 123.2 | 0.00957 |
| Ab50 | 133.4 | 0.00629 |
| Ab51 | 92.2 | 0.02207 |
| Ab52 | 183.9 | 0.02057 |
| Ab53 | 128.4 | 0.0482 |
| Ab54 | 176.5 | 0.02566 |
| Ab55 | 170.5 | 0.01852 |
| Ab56 | 123.4 | 0.01446 |
| Ab57 | 138.6 | 0.01099 |
| Ab58 | 147.1 | 0.01529 |
| Ab59 | 163.5 | 0.01224 |
| Ab60 | 135.0 | 0.00896 |
| Ab61 | 145.2 | 0.01398 |
| Tanezumab | 144.9 | 0.00937 |

NGF binding ELISA assay: NGF binding ELISA assay was performed as described in Example 1. As shown in Table 5, all the anti-NGF antibodies and the reference antibody Tanezumab (Pfizer) bind NGF with high affinity.

TrkA inhibition ELISA assay: The optimized anti-NGF antibodies Ab4, Ab6, Ab10, Ab16, Ab36, Ab37, Ab44, Ab45, Ab46, Ab47, Ab48, Ab49, Ab52, Ab54, Ab55, Ab56, Ab57, Ab58, Ab59, Ab60, Ab61 and the reference antibody Tanezumab (Pfizer), a humanized antibody from mouse hybridoma were further analyzed for their abilities to block NGF binding to its receptor TrkA. TrkA inhibition assay was performed as described in Example 1.

Figure 1B:
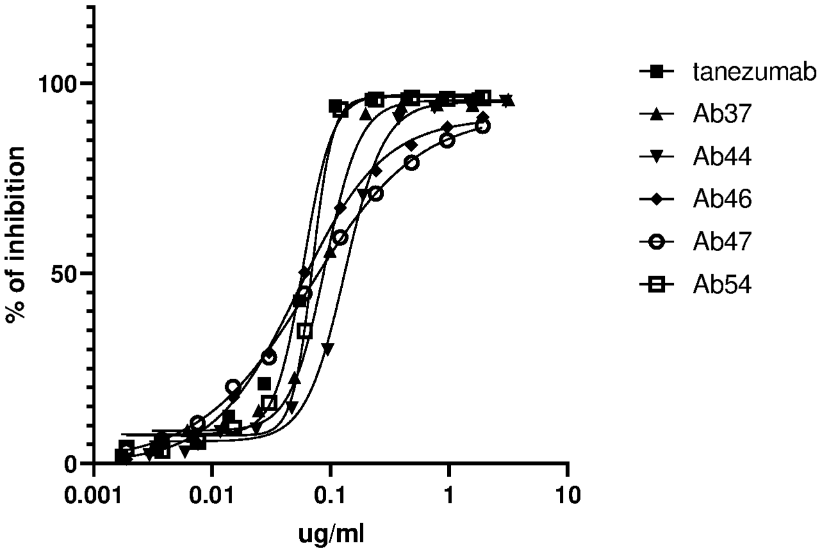
Figure 1C:
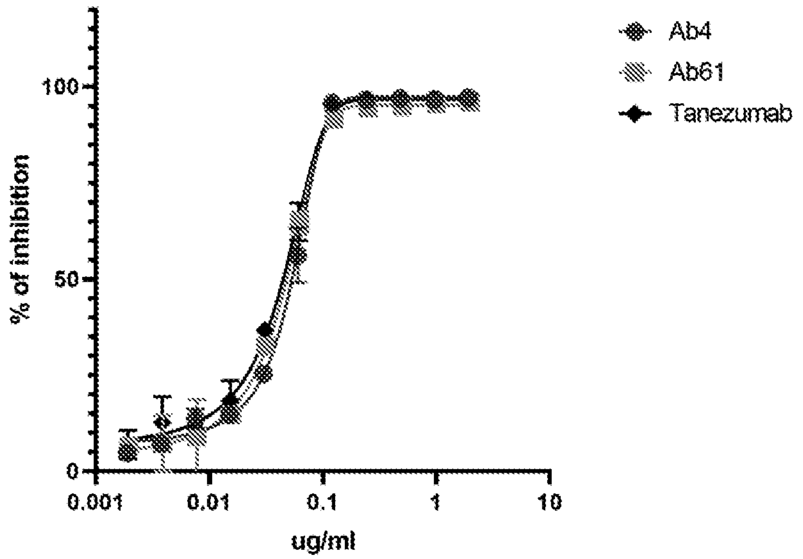

As shown in FIGS. 1A-1C and Table 6, all the optimized anti-NGF antibodies exhibited better or comparable efficacy in blocking NGF binding to its receptor TrkA when compared with the reference antibody Tanezumab.

TABLE 6

| TrkA Inhibition Assay | |
|---|---|
| Antibody | IC50 (ng/mL) |
| Ab4 | 74.6 |
| Ab6 | 76.9 |
| Ab10 | 80.4 |
| Ab16 | 73.5 |
| Ab36 | 89.9 |
| Ab37 | 132.3 |
| Ab42 | 77.3 |
| Ab44 | 130.0 |
| Ab45 | 89.8 |
| Ab46 | 53.3 |
| Ab47 | 66.2 |
| Ab48 | 93.5 |
| Ab49 | 87.8 |

TABLE 6-continued

| TrkA Inhibition Assay | |
|---|---|
| Antibody | IC50 (ng/mL) |
| Ab52 | 70.2 |
| Ab54 | 70.2 |
| Ab55 | 75.7 |
| Ab56 | 66.5 |
| Ab57 | 73.2 |
| Ab58 | 80.0 |
| Ab59 | 74.7 |
| Ab60 | 43.4 |
| Ab61 | 70.0 |
| Tanezumab | 60.2 |

p75 inhibition ELISA assay: The optimized anti-NGF antibodies Ab4, Ab61, and the reference antibody Tanezumab, a humanized antibody from mouse hybridoma were further analyzed for their abilities to block NGF binding to its receptor p75. P75 inhibition assay was performed as described in Example 1.

Figure 2:
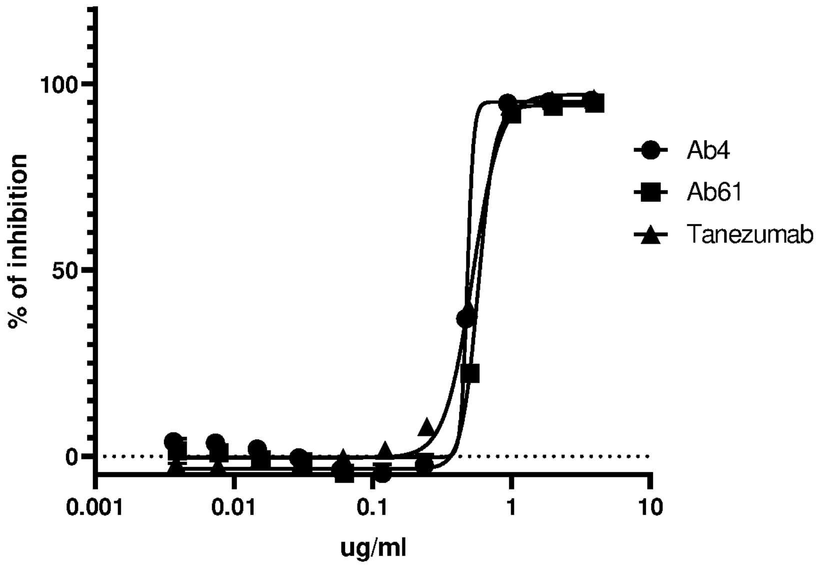
FIG. 2 shows result of the inhibitory effect of the optimized anti-NGF antibodies Ab4 or Ab61 on the binding of NGF to receptor p75, compared with the reference antibody Tanezumab.

As shown in FIG. 2 and Table 7, the optimized anti-NGF antibodies Ab4, and Ab61 exhibited better or comparable efficacy in blocking NGF binding to its receptor p75 when compared with the reference antibody Tanezumab.

TABLE 7

| p75 Inhibition Assay | |
|---|---|
| Antibody | IC50 (ng/mL) |
| Ab4 | 481 |
| Ab61 | 577 |
| Tanezumab | 525 |

Example 3: Characterizing the Specificity and Affinity of Optimized Anti-NGF Antibodies Specificity of Anti-NGF Antibodies The specificity of the optimized anti-NGF antibodies were characterized by measuring cross-reactivity to neurotrophins and polyspecificity assays.

Figure 3A:
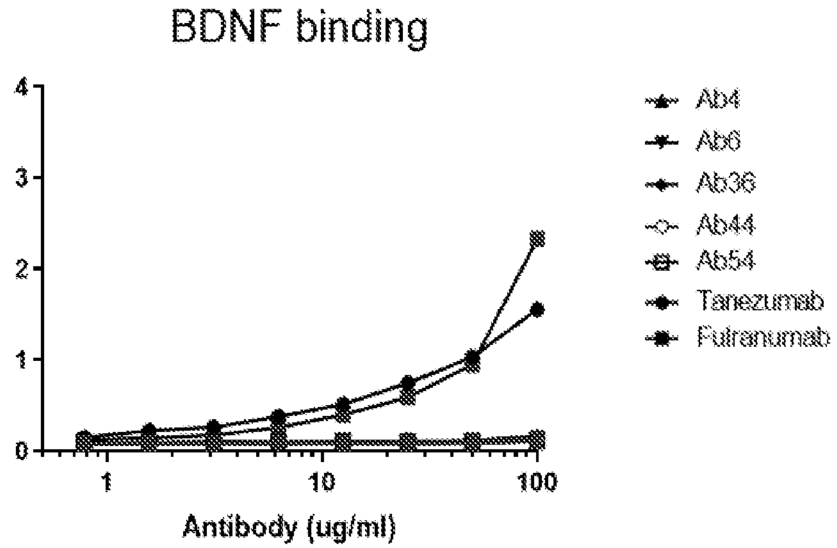
FIGS. 3A-3C show cross reactivities of the optimized anti-NGF antibodies with neurotrophins compared with the reference antibody Tanezumab or Fulranumab.
Figure 3B:
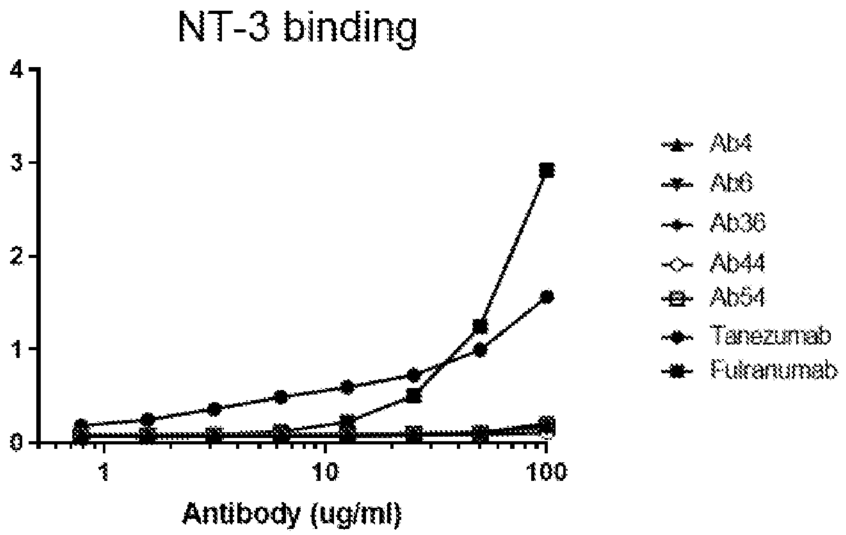
Figure 3C:
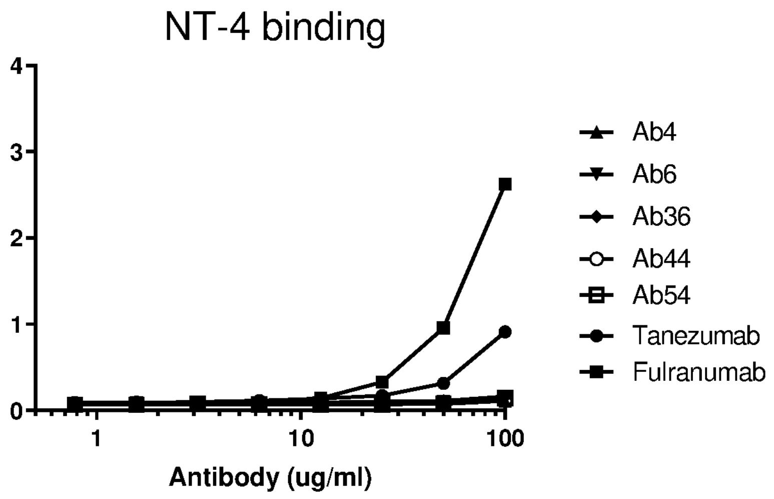

Cross-reactivity to neurotrophins: It has been well known that there is higher sequence homogeneity among neurotrophins, including NGF, BDNF, NT3 and NT4. In fact, they share a common receptor p75. ELISA methods were used for the detection of the cross-reactions between the optimized NGF antibodies and BDNF, NT3, or NT4, respectively. Two reference antibodies, Tanezumab (Pfizer), a humanized antibody from mouse hybridoma, and Fulranumab (Amgen), a fully-human antibody from transgenic mouse, were chosen as controls and subjected to the same test in parallel. As shown in FIGS. 3A-3C, compared with two reference antibodies Tanezumab and Fulranumab, the optimized antibodies Ab4, Ab6, Ab36, Ab44 and Ab54 didn't exhibit any significant cross reactions with BDNF, NT3 or NT4, even at a very high concentration of 100 μg/mL.

Polyspecificity assays: Polyspecificity of an antibody is believed to be related to pharmacokinetic and pharmacodynamics properties.

In dsDNA or insulin assays, the Corning 3366 high binding 96 well plates were coated with 5 μg/mL of dsDNA (Sigma) or insulin (Sigma) in 1×PBS solution, with 50 μL per well. The plates were incubated at 4 °C overnight. The next day, ELISA plates were washed three times with 1×PBS to remove unbound dsDNA or Insulin.

In Baculovirus particles (BVP) assay, the BVP stock (BlueSky Biotech) was diluted at the ratio of 1:100 with 50 mM sodium carbonate (pH 9.6), with 50 μL per well, and incubated on ELISA plates (3369; Corning) at 4 °C overnight. The next day, ELISA plates were washed manually three times with 1×PBS to remove unbound BVPs.

All remaining steps were performed at room temperature. 200 μL of blocking buffer (PBS with 1% BSA, No Tween) was added to each well and incubated for 1 h before three washes with 200 μL 1×PBS. Next, 50 μL of 100 μg/ml testing antibodies in blocking buffer was added to each well with serially 2-fold dilution. Primary antibodies were incubated for 1 h followed by three washes with 200 μL of 1×PBS. 50 μL of 1:2000 diluted anti-human IgG Fc antibody AP conjugated (Southern Biotech) was added to each well and incubated for 1 h followed by three washes as before. Finally, 50 μL of PNPP substrate was added to each well and incubated for 20-30 min. The absorbance was read at 405 nm and dsDNA or Insulin score was determined by normalization by absorbance in blank wells without test antibody.

Figure 4A:
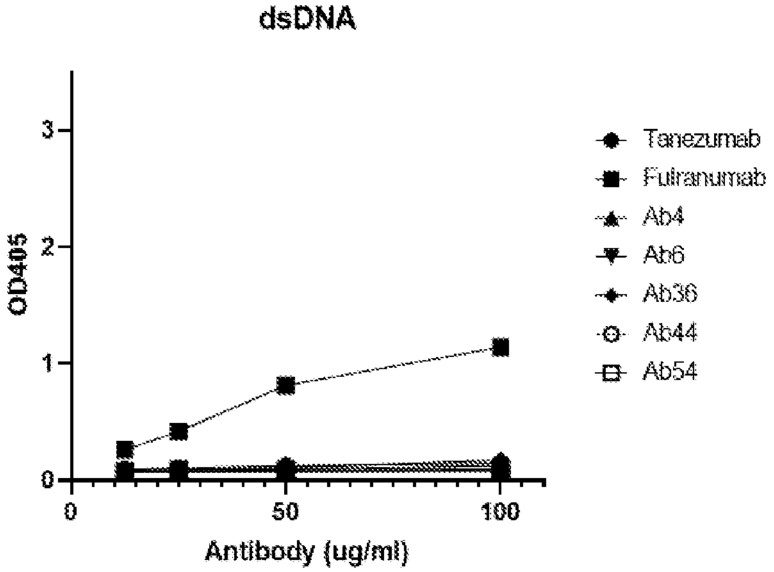
FIGS. 4A-4C show the polyspecificity results of the optimized anti-NGF antibodies compared with the reference antibody Tanezumab or Fulranumab.
Figure 4B:
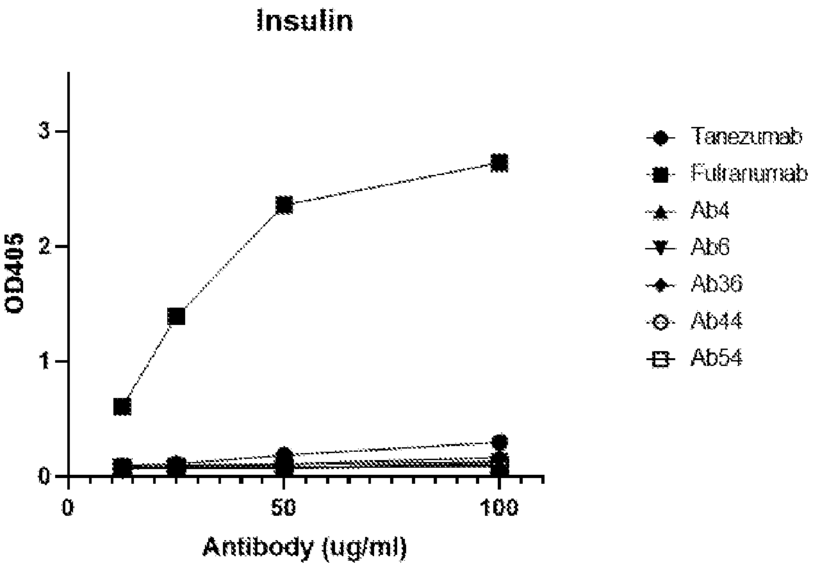
Figure 4C:
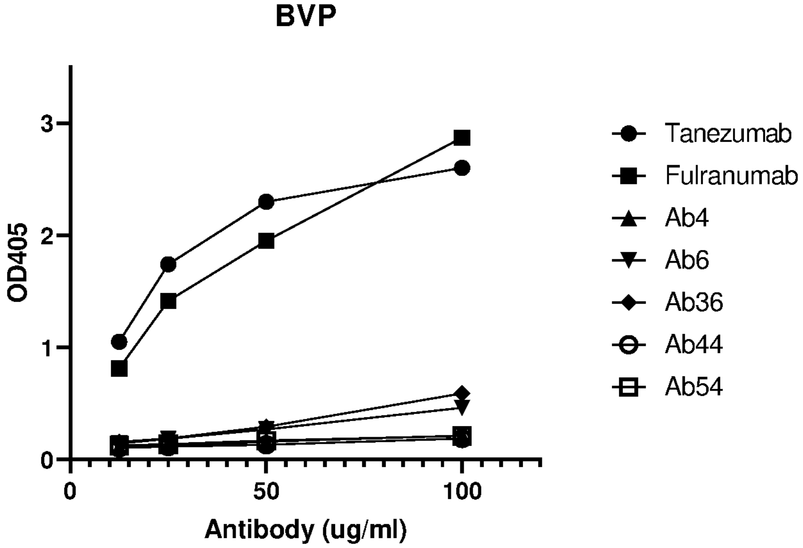

Two reference antibodies Tanezumab and Fulranumab were chosen as references and subjected to the same tests in parallel. Compared with two references, as shown in FIGS. 4A-4C, the optimized antibodies Ab4, Ab6, Ab36, Ab44 and Ab54 didn't exhibit any significant polyspecificity reactions to dsDNA, insulin or BVP, even at a very high concentration of 100 μg/mL.

Characterization of Binding Affinity and Dissociation Constant (Kd)

ForteBio BioLayer Interferometry (BLI) technology was chosen as the method for affinity determination by using Octet Red system. NGF is a homodimer protein in its nature form. When it binds with full-length antibodies, the binding model does not show 1:1 bimolecular interaction, resulting in the kinetic behavior of avidity instead of affinity. For the purpose of affinity measurement, monovalent Fab fragments of IgG were prepared using Fab preparation kit (Pierce).

After purification, the Fab concentration was determined by OD280 according to the extinction coefficient calculated based on its sequence. In affinity assay, human NGF-Fc protein was captured by the anti-human Fc sensors (AHC, Pall) with the loading concentration of 2 μg/mL in kinetic buffer for 300 seconds. For each assay, an array of Fab concentrations from about 50 nM to less than 1 nM in kinetic buffer (PALL) were tested by NGF-Fc sensors with the association time of 300 seconds and dissociation time of 1200 seconds. The kinetic data were analyzed using program Data Analysis HT 10.0 according to the manual. All the tests were repeated at least twice in independent assays. Table 8 shows the Kd, Ka, and Kdis of the optimized anti-NGF antibodies and the reference antibody Tanezumab.

TABLE 8

| Binding affinity and dissociation constant (Kd) | | | |
|---|---|---|---|
| Antibody | Kd (M) | Ka(1/Ms) | Kdis(1/s) |
| Ab4 | 7.46E−11 | 4.01E+05 | 2.99E−05 |
| Ab6 | 8.66E−10 | 7.31E+04 | 6.33E−05 |
| Ab10 | 6.48E−10 | 1.15E+04 | 7.48E−05 |
| Ab16 | 1.37E−09 | 5.17E+04 | 7.11E−05 |
| Ab36 | 2.58E−10 | 2.85E+05 | 7.35E−05 |
| Ab37 | 3.25E−09 | 1.62E+04 | 5.27E−05 |
| Ab44 | 7.04E−10 | 8.38E+04 | 5.90E−05 |
| Ab46 | 2.89E−09 | 3.71E+04 | 1.07E−04 |
| Ab47 | 3.48E−09 | 4.07E+04 | 1.42E−04 |

TABLE 8-continued

| Binding affinity and dissociation constant (Kd) | | | |
|---|---|---|---|
| Antibody | Kd (M) | Ka(1/Ms) | Kdis(1/s) |
| Ab54 | 1.48E−10 | 3.00E+05 | 4.43E−05 |
| Ab61 | 1.39E−10 | 3.70E+05 | 5.13E−05 |
| Tanezumab | 1.69E−10 | 3.64E+05 | 6.14E−05 |

Example 4: The Inhibition of NGF Induced TF1 Cell Proliferation Assay

TF-1 Cell Proliferation Assay

TF1 cell is a human erythroleukemic cell line that is factor-dependent and can proliferate in the presence of cytokines such as GM-CSF, IL-4 and NGF. TF1 cells express TrkA receptor but not p75. The ability of the optimized anti-NGF antibodies Ab4, Ab6, Ab10, Ab16, Ab36, Ab37, Ab44, Ab46, Ab47, Ab54 to inhibit NGF-induced proliferation of TF1 cell line was determined according to the following protocol.

The TF1 cell line (ATCC) was maintained in growth media containing RPMI 1640+10% FBS+1% L Glutamine+0.1% Pen/Strep, with the addition of GM-CSF at 2 ng/ml (R&D system). Before the assay, the GM-CSF was removed by 3 cycles of spinning down at 300×g for 5 minutes and the cells were re-suspended in the assay media (the same growth media as above but without GM-CSF). After this process the TF1 cells were re-resuspended in assay media at a final concentration of $4\times10^5$/mL and incubated in a 37 °C, 5% CO2 for 1 hour, i.e NGF starvation. Anti-NGF antibodies were diluted serially at different concentrations in the assay media and pre-incubated in triplicate with human NGF (R&D system) of 20 ng/ml for 1 hour at room temperature. By mixing 50 µl of the TF1 cells with 50 µl of antibody/NGF reaction solution, a total of 100 µl of the mixture were transferred to each well of the white 96 well culture plates (PerkinElmer), with a final cell density at $1\times10^4$/well and 10 ng/ml of human NGF. Assay plates were incubated for 48 hrs at 37 °C in 5% $CO_2$ in a humidified chamber. The results of TF1 cell proliferation under anti-NGF antibodies were determined by using ATPlite 1 step Luminescence Assay kit (PerkinElmer). According to its manual, 100 µl of the substrate solution was added to each well of the 96-well plates. After mixing 2 minutes by shake at 700 rpm, the plates were read for luminescence in Biotek Synergy Neo2 reader.

Figure 5A:
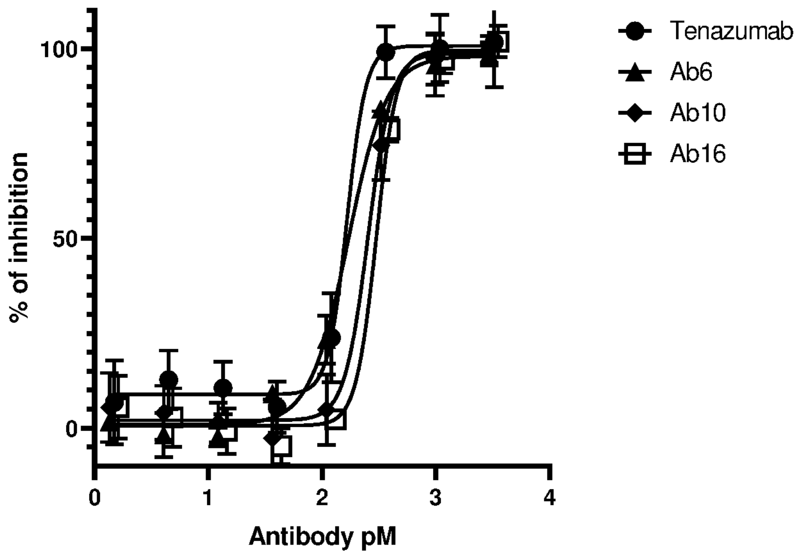
FIGS. 5A-5B show inhibitory effects on NGF-induced TF-1 cell proliferation assay of the optimized anti-NGF antibodies.
Figure 5B:
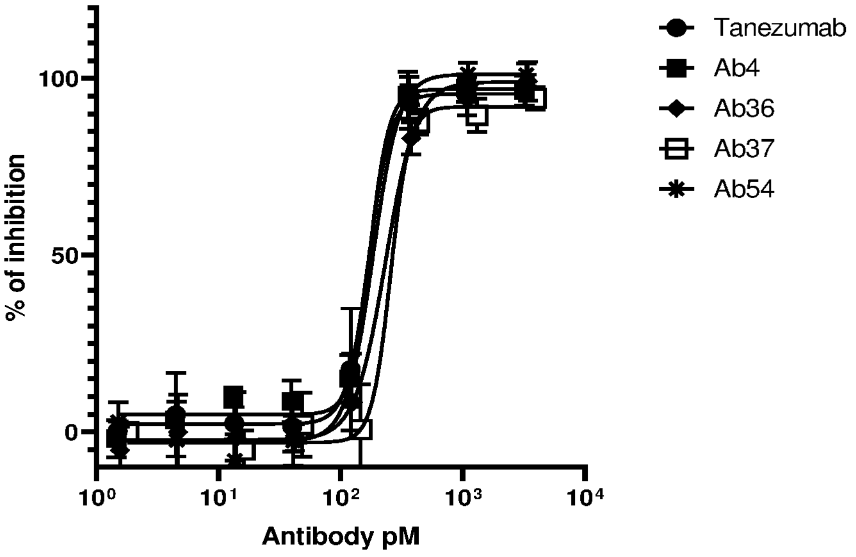

As shown in FIG. 5A-5B and Table 9, the optimized anti-NGF antibodies Ab4, Ab6, Ab10, Ab16, Ab36, Ab37, Ab54, Ab55, Ab61 and the reference antibody Tanezumab all exhibited good efficacy in inhibiting NGF-induced proliferation of TF1 cell line.

TABLE 9

| TF1 Cell Proliferation Inhibition Assay | |
|---|---|
| Antibody | IC50 (pM) |
| Ab4 | 173.9 |
| Ab6 | 169.9 |
| Ab10 | 254.2 |
| Ab16 | 300.2 |
| Ab36 | 234.4 |
| Ab37 | 256.8 |

TABLE 9-continued

| TF1 Cell Proliferation Inhibition Assay | |
|---|---|
| Antibody | IC50 (pM) |
| Ab54 | 183.5 |
| Ab55 | 184.5 |
| Ab61 | 346 |
| Tanezumab | 170.3 |

Example 5: The Inhibition of NGF-Dependent ERK1/2 Phosphorylation Assay

PC12 Cell ERK1/2 Signaling Pathway

PC12 cells are a rat pheochromocytoma-derived cell line and express both TrkA and p75 receptors on cell surface. The PC12 cell can grow and differentiate in response to NGF, which is involved with multiple signaling pathways, including ERK1/2 phosphorylation. The ability of the optimized anti-NGF antibodies Ab4, Ab61 and the reference antibody Tanezumab to inhibit NGF dependent ERK1/2 phosphorylation was determined according to the following protocol.

In this assay, the PC12 cells were purchased from the Sigma company (ECACC) and maintained in suspension in RPMI 1640+2 mM Glutamine, 10% horse serum, 5% fetal bovine serum (FBS). Before signaling assays, PC12 cells were transferred into the assay media of Opti-MEM/0.1% BSA by repeatedly pelleting at 300 g for 5 minutes and re-suspended in the media. The cells were then prepared into a single cell suspension, plated at $1.0\times10^5$ cells/well into collagen Type IV coated 96-well microplates (BioCoat™; BD Biosciences), and incubated overnight at 37 °C in 5% $CO_2$, i.e. serum starvation. Anti-NGF antibodies serially diluted in different concentration were pre-incubated with human NGF (R&D Systems, final concentration of 10 ng/ml) in the assay media of Opti-MEM/0.1% BSA for 1 hr at 37 °C, and then added into each well of the 96-well microplates in triples. After stimulating PC12 cells for 15 min at 37 °C by human NGF, the cells were lysed by using freshly prepared 1×lysis buffer from AlphaScreen® kit (PerkinElmer) according to the manufacturer's instructions for adherent cells. The levels of phosphorylated ERK1/2 protein under different anti-NGF antibody concentrations were detected using AlphaScreen® SureFire® p-ERK1/2 (Thr202/Tyr204) Assay kit (PerkinElmer) according to the manufacturer's instructions for adherent cells in white ½ area 96 plate (PerkinElmer). Plates were read for luminescence in Biotek Synergy Neo2 reader.

Figure 6:
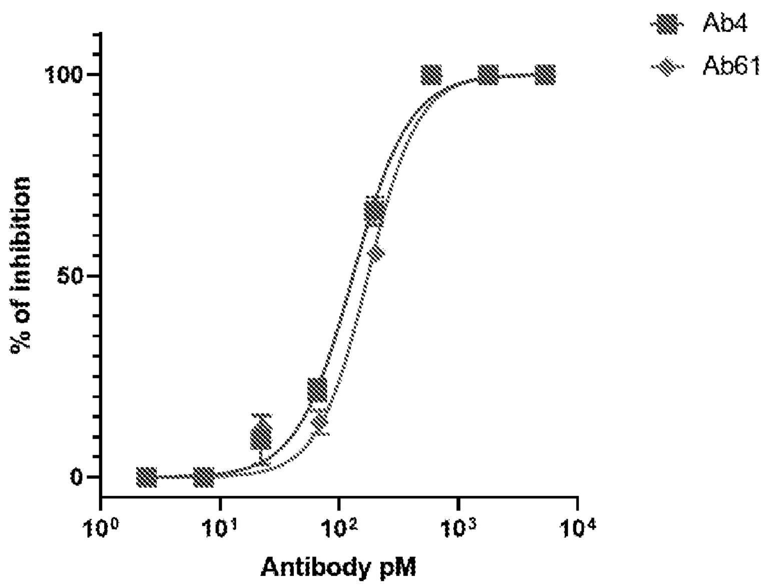
FIG. 6 shows the result of the optimized anti-NGF antibody Ab4 or Ab61 in inhibiting the NGF-dependent ERK1/2 phosphorylation in PC12 cells.

As shown in FIG. 6 and Table 10, the optimized anti-NGF antibodies Ab4, Ab61 exhibited good efficacy in inhibiting NGF dependent ERK1/2 phosphorylation.

TABLE 10

| ERK1/2 Signaling Pathway Inhibition Assay | | |
|---|---|---|
| Antibody | Ab4 | Ab61 |
| IC50 (pM) | 130.9 | 174.5 |

Example 6: NGF-Induced Chicken DRG Neurite Outgrowth Inhibition Assay

In the presence of NGF, the neuron cells of chicken dorsal root ganglia (DRG) can survive and differentiate to outgrow neurites in vitro. The ability of the optimized anti-NGF antibodies Ab4, Ab61 and the reference antibody Tanezumab to induce chicken DRG neurite outgrowth was determined according to the following protocol.

In the assay, DRGs were isolated from the lumbar regions of embryos on embryonic day 8 (E8), and collected by a mechanical treatment under a dissecting microscope. The isolated DRGs were plated onto the culture bottles coated with mouse tail collagen. Each bottle contained 4 collected DRGs. For each anti-NGF antibody tested in the assay, 6 concentration titers were set up, with two control bottles having no-NGF or no-antibody respectively. 2 mL of serum-free Dulbecco's modified Eagle's medium (DMEM) (Gibco-BRL) was added to each DRG culture bottle, containing human NGF (final concentration of 4 ng/mL) and the tested antibody with a variety of concentrations. The DRGs were incubated for 24 hrs at 37 °C with 5% $CO_2$ in water-saturated air. Digital images of DRGs were taken to quantify neurite outgrowth of DRGs under an inverted microscope. Three of the four DRGs were chosen for analysis from each culture bottle. The results were scored as (−) and (+ to ++++), based on the neurite's lengths and density around DRG.

Figure 7:
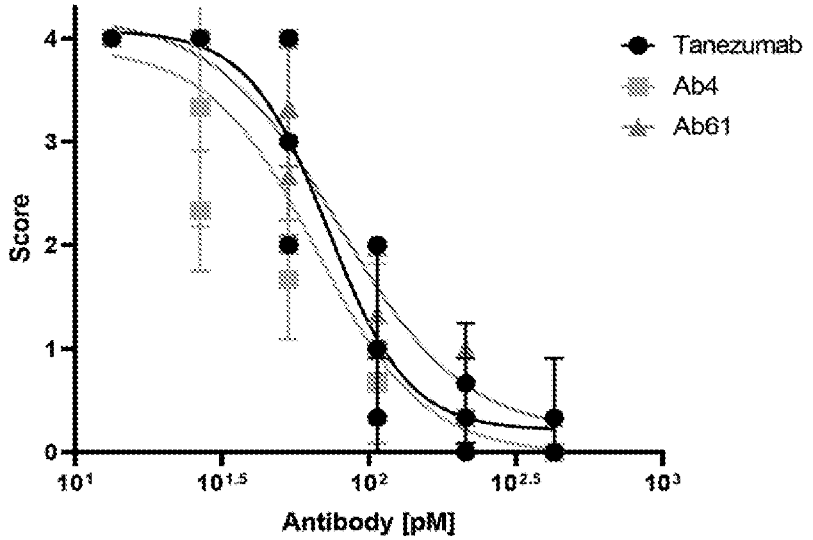
FIG. 7 shows results of the optimized anti-NGF antibody Ab4 or Ab61 in the inhibition of NGF-induced chicken DRG neurite outgrowth as compared to Tanezumab.

As shown in FIG. 7 and Table 11, the optimized anti-NGF antibodies Ab4, Ab61 exhibited better or comparable efficacy in inducing chicken DRG neurite outgrowth when compared with the reference antibody Tanezumab.

TABLE 11

| Chicken DRG Neurite Outgrowth Inhibition Assay | | | |
|---|---|---|---|
| Antibody | Ab4 | Ab61 | Tanezumab |
| IC50 (pM) | 66.3 | 78.6 | 72.7 |

Example 7: Plantar Incision Prevention Test

Animals and husbandry: CD-1 mice (7-8 weeks of age) were used in the studies. They were housed in a temperature (19.5-24.5 °C) and relative humidity (45-65%) controlled room with a 12-h light/dark cycle, with ad libitum access to filtered tap-water and Rodent Diet throughout the study. Upon receipt at animal facilities, they were housed and observed for a 3-day acclimatization period before any testing.

Screening of qualified mice: the paw withdrawal threshold (PWT) was measured with a dynamic plantar esthesiometer after stimulating the paws of the mouse (inside the foot pads) with a mechanical blunt tip. The PWT was measured 4 times, followed by calculating the average threshold of the left and right paws of the mouse, respectively. The mice with thresholds between 7.0 and 10.0 were qualified for further studies. T-test was also used to statistically analyze the P-value of left and right paw thresholds of the same mouse, and the mice with P-value >0.05 were qualified.

Antibody administration: Subcutaneously antibody administration was performed 24 h before Plantar incision surgery. Mice were randomly divided into four groups (6 mice per group) as follows: i) blank control group, subcutaneously injected with 10 μl/g PBS (n=6) instead of Plantar incision surgery; ii) negative control group, subcutaneously injected with 25 mg/kg irrelevant antibody (not anti-NGF antibody) (n=6); iii) 3 low-dose experimental groups, subcutaneously injected with 10 mg/kg anti-NGF antibodies (Tanezumab, Ab4, Ab61), respectively (n=6); and iv) 3 high-dose experimental groups, subcutaneously injected with 25 mg/kg anti-NGF antibodies (Tanezumab, Ab4, Ab61), respectively (n=6).

Plantar incision: The plantar surgery was performed as previously described (Brennan T J, Vandermeulen E P, Gebhart G. Characterization of a rat model of incisional pain. Pain 1996; 64:493-502). In brief, after aseptic preparation and draping, a 1-cm longitudinal skin incision was made on the plantar surface of the left hind paw, starting 0.5 cm distal to the tibiotarsus, and extending toward the digits. The plantaris muscle was elevated with forceps and incised longitudinally, leaving muscle origin and insertion intact. After hemostasis with gentle pressure, the incision was closed with two interrupted horizontal mattress sutures of 5-0 nylon. The incision was checked daily, and animals that exhibited any sign of wound infection or dehiscence were excluded from the study. Blank control group mice didn't perform Plantar incision surgery.

Paw withdrawal threshold (PWT) testing: At 24 h before Plantar incision surgery (baseline) and 6 h, 24 h, 48 h, 72 h, and 96 h after the surgery, the paw withdrawal threshold (PWT) of the mice were measured with a dynamic plantar esthesiometer. GraphPad Prism software and analysis of ANOVA was used to analyze the differences between each experimental group and the negative control group. P<0.05 indicates a statistically significant difference, and P<0.01 indicates a highly statistically significant difference.

The PWT in the negative control group before Plantar incision was highly statistically significantly different from that in the blank control group, in the entire process of the experiment (p<0.01), indicating that the experiments were successful in modeling and the model was feasible and workable.

Figure 8A:
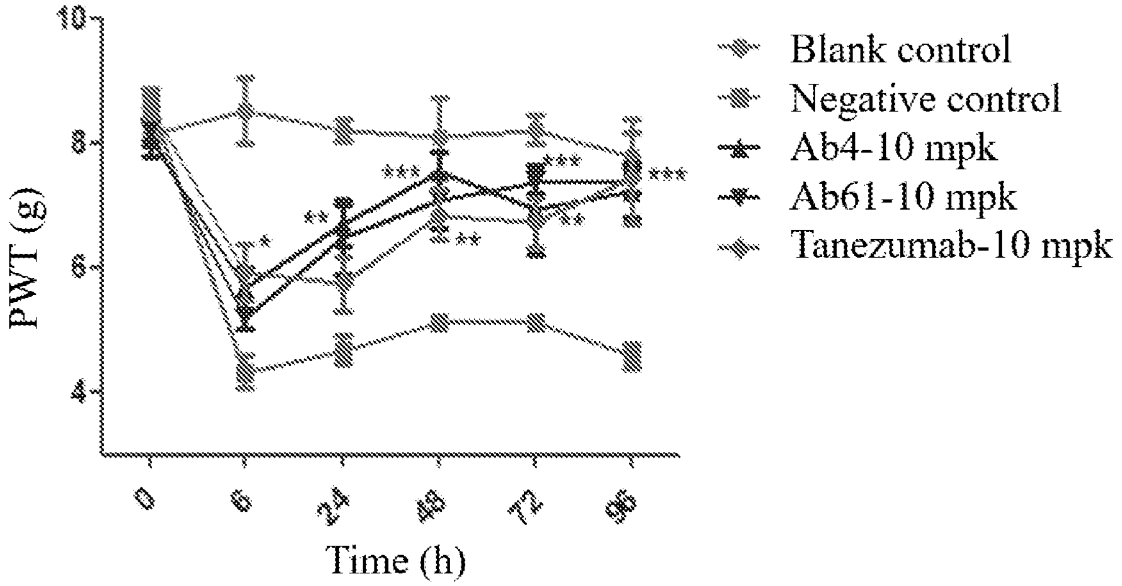
FIGS. 8A-8B show the PWT results of the optimized anti-NGF antibody Ab4 or Ab61 in the plantar incision prevention test as compared to Tanezumab.

As shown in FIG. 8A, in the low-dose antibody group (10 mg/kg): at 6 h after surgery, PWTs increased in all of the experiment groups. PWT of the mice in the Ab4 or Tanezumab group was statistically significantly different from that in the negative control group (P<0.05). At 24 h after surgery, PWT in the Ab4 or Ab61 group was highly statistically significantly different from that in the negative control group (P<0.01). At 48 h after surgery, the Ab4 group showed highly statistically significant difference from the irrelevant antibody group (P<0.01), both the Ab61 and Tanezumab groups showed statistically significant differences from the negative control group (P<0.05). At 72 h after surgery, Ab61 showed highly statistically significant difference from the irrelevant antibody group (P<0.01), both the Ab4 and Tanezumab groups showed statistically significant difference from the irrelevant antibody group (P<0.05), and at 96 h after surgery, all experiment groups showed highly statistically significant differences from the negative control group (P<0.01).

Figure 8B:
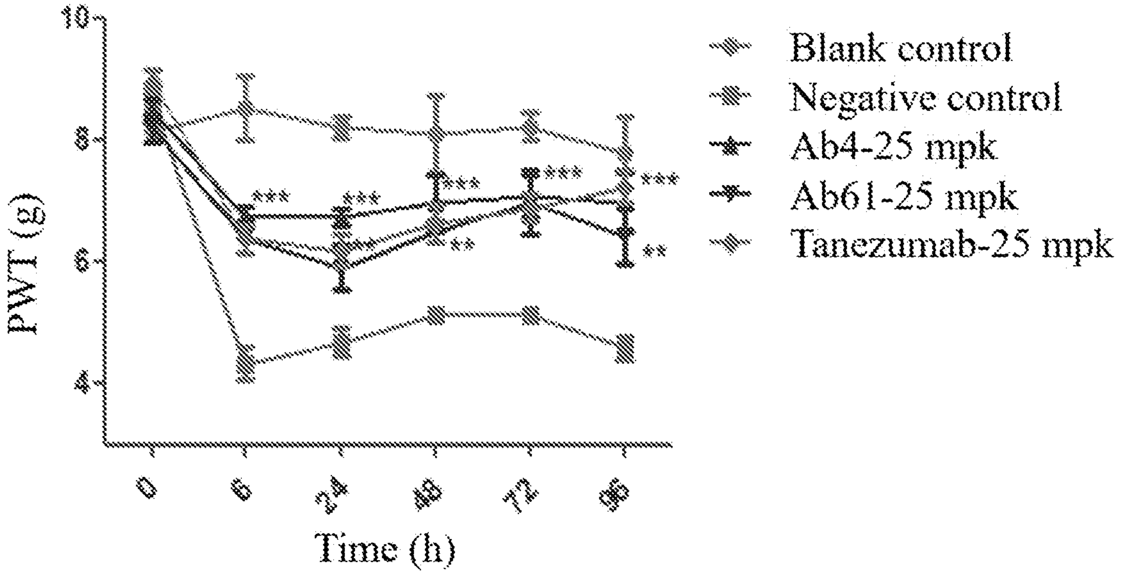

As shown in FIG. 8B, in the high-dose antibody group (25 mg/kg): at 6 h after surgery, PWTs increased in all experiment groups. PWT in Ab4 group was highly statistically significant different from the negative control group (P<0.01), and in Ab61 or Tanezumab group it was statistically significant different (P<0.05). At 24 h after surgery, PWT in Ab4 group remained highly statistically significant different from that in the negative control group (P<0.01), and in Tanezumab group it remained statistically significant different (P<0.05). However, in Ab61 group, there was no significant difference compared to the negative control group. At 48 h and 72 h after surgery, all the groups of Ab4, Ab61 and Tanezumab showed highly statistically significant difference from the irrelevant antibody group (P<0.01). And at 96 h after surgery, both groups of Ab4 and Tanezumab showed highly statistically significant differences from the negative control group ($P<0.01$), and Ab61 group showed statistically significant difference from the negative control group ($P<0.05$).

In conclusion, the above results of the PWT tests suggested that the anti-NGF antibodies Ab4, Ab61 and Tanezumab all showed great effect in reducing pain as compared to the irrelevant antibody in the plantar incision prevention test, and the effect lasted for at least 96 hs after anti-NGF antibody administration.

Example 8: Complete Freund's Adjuvant (CFA)-Induced Inflammatory Pain Assay

Animals, husbandry and Screening of qualified mice: The experimental procedure is the same as described previously in Plantar incision prevention test.

CFA-induced inflammatory pain model: At 24 h before the test, the mice of experimental groups were injected with 20 μl CFA (100%) on the sole of the mouse, and the mice of blank control group were subcutaneously injected with PBS.

Antibody administration: Subcutaneously antibody administration was performed at 24 h after CFA injection. Mice were randomly divided into four groups (6 mice per group) as follows: i) blank control group, subcutaneously injected with 10 μl/g PBS (n=6); ii) negative control group, subcutaneously injected with 25 mg/kg irrelevant antibody (not anti-NGF antibody) (n=6); iii) 3 low-dose experimental groups, subcutaneously injected with 10 mg/kg anti-NGF antibodies (Ab4, Ab61, Tanezumab,), respectively (n=6); and iv) 3 high-dose experimental groups, subcutaneously injected with 25 mg/kg anti-NGF antibodies (Ab4, Ab61, Tanezumab), respectively (n=6).

Paw withdrawal threshold (PWT) testing: At 3 h, 6 h, 24 h, 48 h, and 72 h after CFA injection, the paw withdrawal threshold (PWT) of the mice were measured with a dynamic plantar esthesiometer. GraphPad Prism software and analysis of ANOVA was used to analyze the differences between each experimental group and the negative control group. $P<0.05$ indicates a statistically significant difference, and $P<0.01$ indicates a highly statistically significant difference.

The PWT in the CFA injection group was highly statistically significantly different from the blank control group in the entire process of the experiment ($p<0.01$), indicating that the CFA-induced inflammatory pain model was successful, and the model was feasible and workable.

Figure 9A:
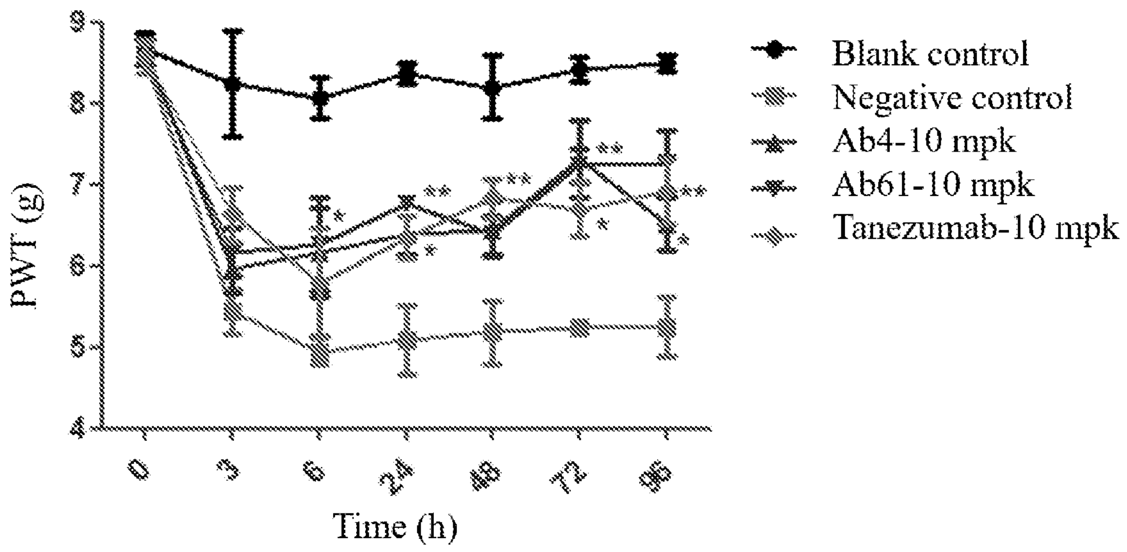
FIGS. 9A-9B show the PWT results of the optimized anti-NGF antibody Ab4 or Ab61 in the Complete Freund's adjuvant (CFA)-induced inflammatory pain assay as compared to Tanezumab.

As shown in FIG. 9A, in the low-dose antibody group (10 mg/kg): at 3 h after antibody injection, PWTs increased in all of the experiment groups. At 6 h after antibody injection, PWT of the mice in the Ab4 or Ab61 was statistically significant differences from the negative control group ($P<0.05$). At 24 h after antibody injection, PWTs in the Ab4, Ab61 or Tanezumab all showed statistically significant difference from the negative control group ($P<0.05$). At 48 h after antibody injection, PWT in the Tanezumab showed highly statistically significant difference from the negative control group ($P<0.01$). At 72 and 96 h after antibody injection, PWTs in the Ab4, Ab61 or Tanezumab all showed statistically significant difference from the negative control group ($P<0.05$).

Figure 9B:
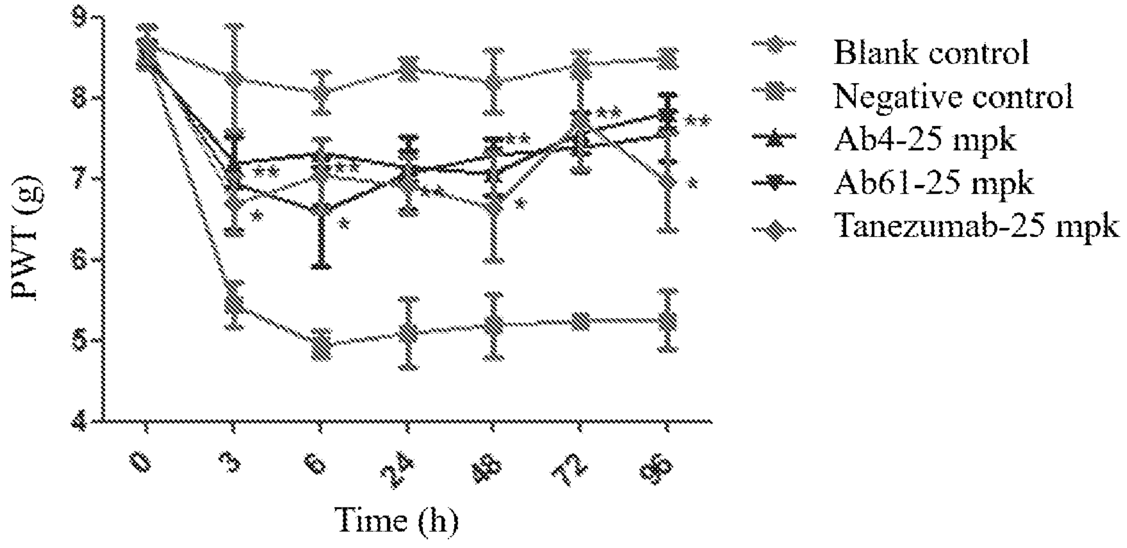

As shown in FIG. 9B, in the high-dose antibody group (25 mg/kg): at all the detection timepoint after the antibody injection, PWTs of the mice in the Ab4, Ab61 or Tanezumab all showed statistically significant difference from the negative control group ($P<0.05$).

In conclusion, the above results of the PWT tests suggested that the anti-NGF antibodies Ab4, Ab61 and Tanezumab all showed great effects in reducing CFA induced inflammatory pain as compared to the irrelevant antibody, and the effect was dose-dependent.

The invention claimed is:

1. An isolated anti-NGF antibody, wherein the antibody comprises:

a heavy chain variable region comprising a heavy chain complementarity determining region (HC-CDR) 1 comprising TYWIS (SEQ ID NO: 1), an HC-CDR2 comprising AIDPSDSDARYSPSFQG (SEQ ID NO: 2), and an HC-CDR3 comprising SDPGYSGYSLLY-GFDS (SEQ ID NO: 3), or a variant thereof comprising up to about 5 amino acid substitutions in the HC-CDRs; and a light chain variable region comprising a light chain complementarity determining region (LC-CDR) 1 comprising RSSQSLVQRNGNTYLS (SEQ ID NO: 4), or RSSQSLVQRNANTYLS (SEQ ID NO: 7), an LC-CDR2 comprising QVSNRYS (SEQ ID NO: 5), and an LC-CDR3 comprising GQGAHLPLT (SEQ ID NO: 6).

2. The isolated anti-NGF antibody of claim 1, wherein the anti-NGF antibody binds to the nerve growth factor with a Kd from about 0.1 μM to about 1 nM.

3. The isolated anti-NGF antibody of claim 1, comprising:

(i) a $V_H$ comprising the amino acid sequence of SEQ ID NO: 8; or a variant thereof having at least about 90% sequence identity to the Amino acid sequence of SEQ ID NO: 8; and a $V_L$ comprising the amino acid sequence of SEQ ID NO: 17 or a variant thereof having at least about 90% sequence identity to the amino acid sequence of SEQ ID NO: 17);

(ii) a $V_H$ comprising the amino acid sequence of SEQ ID NO: 8 or a variant thereof having at least 90% sequence identity to the amino acid sequence of SEQ ID NO: 8; and a $V_L$ comprising the amino acid sequence of SEQ ID NO: 19 or a variant thereof having at least about 90% sequence identity to the amino acid sequence of SEQ ID NO: 19;

(iii) a $V_H$ comprising the amino acid sequence of SEQ ID NO: 8 or a variant thereof having at least 90% sequence identity to the amino acid sequence of SEQ ID NO: 8; and a $V_L$ comprising the amino acid sequence of SEQ ID NO: 23 or a variant thereof having at least about 90% sequence identity to the amino acid sequence of SEQ ID NO: 23;

(iv) a $V_H$ comprising the amino acid sequence of SEQ ID NO: 9 or a variant thereof having at least about 90% sequence identity to the amino acid sequence of SEQ ID NO: 9; and a $V_L$ comprising the amino acid sequence of SEQ ID NO: 19 or a variant thereof having at last about 90% sequence identity to the amino acid sequence of SEQ ID NO: 19;

(v) a $V_H$ comprising the amino acid sequence of SEQ ID NO: 11 or a variant thereof having at last about 90% sequence identity to the amino acid sequence of SEQ ID NO: 11; and a $V_L$ comprising the amino acid sequence of SEQ ID NO: 19 or a variant thereof having at last about 90% sequence identity to the amino acid sequence of SEQ ID NO: 19;

(vi) a $V_H$ comprising the amino acid sequence of SEQ ID NO: 11 or a variant thereof having at last about 90% sequence identity to the amino acid sequence of SEQ ID NO: 11; and a $V_L$ comprising the amino acid sequence of SEQ ID NO: 20 or a variant thereof having at last about 90% sequence identity to the amino acid sequence of SEQ ID NO: 20;

(vii) a $V_H$ comprising the amino acid sequence of SEQ ID NO: 12 or a variant thereof having at last about 90% sequence identity to the amino acid sequence of SEQ ID NO: 12; and a $V_L$ comprising the amino acid sequence of SEQ ID NO: 17 or a variant thereof having at last about 90% sequence identity to the amino acid sequence of SEQ ID NO: 17;

(viii) a $V_H$ comprising the amino acid sequence of SEQ ID NO: 12 or a variant thereof having at last about 90% sequence identity to the amino acid sequence of SEQ ID NO: 12; and a $V_L$ comprising the amino acid sequence of SEQ ID NO: 19 or a variant thereof having at last about 90% sequence identity to the amino acid sequence of SEQ ID NO: 19;

(ix) a $V_H$ comprising the amino acid sequence of SEQ ID NO: 12 or a variant thereof having at last about 90% sequence identity to the amino acid sequence of SEQ ID NO: 12; and a $V_L$ comprising the amino acid sequence of SEQ ID NO: 20 or a variant thereof having at last about 90% sequence identity to the amino acid sequence of SEQ ID NO: 20;

(x) a $V_H$ comprising the amino acid sequence of SEQ ID NO: 13 or a variant thereof having at last about 90% sequence identity to the amino acid sequence of SEQ ID NO: 13; and a $V_L$ comprising the amino acid sequence of SEQ ID NO: 17 or a variant thereof having at last about 90% sequence identity to the amino acid sequence of SEQ ID NO: 17; or (xi) a $V_H$ comprising the amino acid sequence of SEQ ID NO: 8 or a variant thereof having at last about 90% sequence identity to the amino acid sequence of SEQ ID NO: 8; and a $V_L$ comprising the amino acid sequence of SEQ ID NO: 24 or a variant thereof having at last about 90% sequence identity to the amino acid sequence of SEQ ID NO: 24.

4. The isolated anti-NGF antibody according to claim 1, wherein the anti-NGF antibody comprises an Fc fragment.

5. The isolated anti-NGF antibody of claim 4, wherein the anti-NGF antibody is a full-length IgG antibody.

6. The isolated anti-NGF antibody of claim 5, wherein the anti-NGF antibody is a full-length IgG1 or IgG4 antibody.

7. The isolated anti-NGF antibody of claim 1, wherein the anti-NGF antibody is human antibody.

8. The isolated anti-NGF antibody according to claim 1, wherein the anti-NGF antibody is an antigen binding fragment selected from the group consisting of a Fab, a Fab', a F(ab)'2, a Fab'-SH, a single-chain Fv (scFv), an Fv fragment, and a diabody.

9. A pharmaceutical composition comprising the anti-NGF antibody according to claim 1, and a pharmaceutically acceptable carrier.

10. A method of treating a disease or condition in an individual in need thereof, comprising administering to the individual an effective amount of the pharmaceutical composition of claim 9, wherein the disease or condition is caused by increased expression of NGF or increased sensitivity to NGF, and wherein the disease or condition is selected from the group consisting of inflammatory pain, post-operative incision pain, neuropathic pain, fracture pain, gout joint pain, pain resulting from burns, cancer pain, osteoarthritis or rheumatoid arthritis pain, sciatica, pain associated with sickle cell crises, and post-herpetic neuralgia.

* * * * *

SEQUENCE LISTING

```
<160> NUMBER OF SEQ ID NOS: 39

<210> SEQ ID NO 1
<211> LENGTH: 5
<212> TYPE: PRT
<213> ORGANISM: Artificial Sequence
<220> FEATURE:
<223> OTHER INFORMATION: HC-CDR1

<400> SEQUENCE: 1

Thr Tyr Trp Ile Ser
1               5


<210> SEQ ID NO 2
<211> LENGTH: 17
<212> TYPE: PRT
<213> ORGANISM: Artificial Sequence
<220> FEATURE:
<223> OTHER INFORMATION: HC-CDR2

<400> SEQUENCE: 2

Ala Ile Asp Pro Ser Asp Ser Asp Ala Arg Tyr Ser Pro Ser Phe Gln
1               5                   10                  15

Gly


<210> SEQ ID NO 3
<211> LENGTH: 16
<212> TYPE: PRT
```

<213> ORGANISM: Artificial Sequence
<220> FEATURE:
<223> OTHER INFORMATION: HC-CDR3

<400> SEQUENCE: 3

Ser Asp Pro Gly Tyr Ser Gly Tyr Ser Leu Leu Tyr Gly Phe Asp Ser
1 5 10 15

<210> SEQ ID NO 4
<211> LENGTH: 16
<212> TYPE: PRT
<213> ORGANISM: Artificial Sequence
<220> FEATURE:
<223> OTHER INFORMATION: LC-CDR1

<400> SEQUENCE: 4

Arg Ser Ser Gln Ser Leu Val Gln Arg Asn Gly Asn Thr Tyr Leu Ser
1 5 10 15

<210> SEQ ID NO 5
<211> LENGTH: 7
<212> TYPE: PRT
<213> ORGANISM: Artificial Sequence
<220> FEATURE:
<223> OTHER INFORMATION: LC-CDR2

<400> SEQUENCE: 5

Gln Val Ser Asn Arg Tyr Ser
1 5

<210> SEQ ID NO 6
<211> LENGTH: 9
<212> TYPE: PRT
<213> ORGANISM: Artificial Sequence
<220> FEATURE:
<223> OTHER INFORMATION: LC-CDR3

<400> SEQUENCE: 6

Gly Gln Gly Ala His Leu Pro Leu Thr
1 5

<210> SEQ ID NO 7
<211> LENGTH: 16
<212> TYPE: PRT
<213> ORGANISM: Artificial Sequence
<220> FEATURE:
<223> OTHER INFORMATION: LC-CDR1

<400> SEQUENCE: 7

Arg Ser Ser Gln Ser Leu Val Gln Arg Asn Ala Asn Thr Tyr Leu Ser
1 5 10 15

<210> SEQ ID NO 8
<211> LENGTH: 125
<212> TYPE: PRT
<213> ORGANISM: Artificial Sequence
<220> FEATURE:
<223> OTHER INFORMATION: isolated anti-NGF antibody VH

<400> SEQUENCE: 8

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Ile Thr Tyr
20 25 30

Trp Ile Ser Trp Val Gln Gln Ala Pro Gly Lys Gly Leu Glu Trp Met
35 40 45

```
Gly Ala Ile Asp Pro Ser Asp Ser Asp Ala Arg Tyr Ser Pro Ser Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Lys Ser Asp Pro Gly Tyr Ser Gly Tyr Ser Leu Leu Tyr Gly Phe
            100                 105                 110

Asp Ser Trp Gly Gln Gly Thr Leu Val Thr Val Ser Ser
        115                 120                 125


<210> SEQ ID NO 9
<211> LENGTH: 125
<212> TYPE: PRT
<213> ORGANISM: Artificial Sequence
<220> FEATURE:
<223> OTHER INFORMATION: isolated anti-NGF antibody VH

<400> SEQUENCE: 9

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Ile Thr Tyr
            20                  25                  30

Trp Ile Ser Trp Val Gln Gln Ala Pro Gly Lys Gly Leu Glu Trp Met
        35                  40                  45

Gly Ala Ile Asp Pro Ser Asp Ser Asp Ala Arg Tyr Ser Pro Ser Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Lys Ser Asp Pro Gly Tyr Ser Gly Tyr Ser Leu Leu Tyr Gly Phe
            100                 105                 110

Asp Ser Trp Gly Gln Gly Thr Leu Val Thr Val Ser Ser
        115                 120                 125


<210> SEQ ID NO 10
<211> LENGTH: 125
<212> TYPE: PRT
<213> ORGANISM: Artificial Sequence
<220> FEATURE:
<223> OTHER INFORMATION: isolated anti-NGF antibody VH

<400> SEQUENCE: 10

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Ile Thr Tyr
            20                  25                  30

Trp Ile Ser Trp Val Gln Gln Ala Pro Gly Lys Gly Leu Glu Trp Met
        35                  40                  45

Gly Ala Ile Asp Pro Ser Asp Ser Asp Ala Arg Tyr Ser Pro Ser Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Lys Ser Asp Pro Gly Tyr Ser Gly Tyr Ser Leu Leu Tyr Gly Phe
```

```
            100                 105                 110

Asp Ser Trp Gly Gln Gly Thr Leu Val Thr Val Ser Ser
        115                 120                 125


<210> SEQ ID NO 11
<211> LENGTH: 125
<212> TYPE: PRT
<213> ORGANISM: Artificial Sequence
<220> FEATURE:
<223> OTHER INFORMATION: isolated anti-NGF antibody VH

<400> SEQUENCE: 11

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Ile Thr Tyr
            20                  25                  30

Trp Ile Ser Trp Val Gln Gln Ala Pro Gly Lys Gly Leu Glu Trp Met
        35                  40                  45

Gly Ala Ile Asp Pro Ser Asp Ser Asp Ala Arg Tyr Ser Pro Ser Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Lys Ser Asp Pro Gly Tyr Ser Gly Tyr Ser Leu Leu Tyr Gly Phe
            100                 105                 110

Asp Ser Trp Gly Gln Gly Thr Leu Val Thr Val Ser Ser
        115                 120                 125


<210> SEQ ID NO 12
<211> LENGTH: 125
<212> TYPE: PRT
<213> ORGANISM: Artificial Sequence
<220> FEATURE:
<223> OTHER INFORMATION: isolated anti-NGF antibody VH

<400> SEQUENCE: 12

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ile Thr Tyr
            20                  25                  30

Trp Ile Ser Trp Val Arg Gln Met Pro Gly Lys Gly Leu Glu Trp Met
        35                  40                  45

Gly Ala Ile Asp Pro Ser Asp Ser Asp Ala Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Lys Ser Asp Pro Gly Tyr Ser Gly Tyr Ser Leu Leu Tyr Gly Phe
            100                 105                 110

Asp Ser Trp Gly Gln Gly Thr Leu Val Thr Val Ser Ser
        115                 120                 125


<210> SEQ ID NO 13
<211> LENGTH: 125
<212> TYPE: PRT
<213> ORGANISM: Artificial Sequence
<220> FEATURE:
```

<223> OTHER INFORMATION: isolated anti-NGF antibody VH

<400> SEQUENCE: 13

Glu Val Gln Leu Val Gln Ser Gly Ala Glu Val Lys Lys Pro Gly Glu
1               5                   10                  15

Ser Leu Lys Ile Ser Cys Lys Ile Ser Gly Tyr Ser Phe Ile Thr Tyr
            20                  25                  30

Trp Ile Ser Trp Val Arg Gln Met Pro Gly Lys Gly Leu Glu Trp Met
        35                  40                  45

Gly Ala Ile Asp Pro Ser Asp Ser Asp Ala Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Lys Ser Asp Pro Gly Tyr Ser Gly Tyr Ser Leu Leu Tyr Gly Phe
            100                 105                 110

Asp Ser Trp Gly Gln Gly Thr Leu Val Thr Val Ser Ser
        115                 120                 125

<210> SEQ ID NO 14
<211> LENGTH: 112
<212> TYPE: PRT
<213> ORGANISM: Artificial Sequence
<220> FEATURE:
<223> OTHER INFORMATION: isolated anti-NGF antibody VL

<400> SEQUENCE: 14

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Gln Arg
            20                  25                  30

Asn Gly Asn Thr Tyr Leu Ser Trp Leu Gln Gln Arg Pro Gly Gln Pro
        35                  40                  45

Pro Arg Leu Leu Ile Tyr Gln Val Ser Asn Arg Tyr Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Ala His Leu Pro Leu Thr Phe Gly Gln Gly Thr Lys Val Glu Ile Lys
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: isolated anti-NGF antibody VL

<400> SEQUENCE: 15

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Gln Arg
            20                  25                  30

Asn Gly Asn Thr Tyr Leu Ser Trp Tyr Gln Gln Arg Pro Gly Gln Pro
        35                  40                  45

Pro Arg Leu Leu Ile Tyr Gln Val Ser Asn Arg Tyr Ser Gly Val Pro

```
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Ala His Leu Pro Leu Thr Phe Gly Gln Gly Thr Lys Val Glu Ile Lys
            100                 105                 110


<210> SEQ ID NO 16
<211> LENGTH: 112
<212> TYPE: PRT
<213> ORGANISM: Artificial Sequence
<220> FEATURE:
<223> OTHER INFORMATION: isolated anti-NGF antibody VL

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Gln Arg
            20                  25                  30

Asn Gly Asn Thr Tyr Leu Ser Trp Phe Gln Gln Arg Pro Gly Gln Ser
        35                  40                  45

Pro Arg Leu Leu Ile Tyr Gln Val Ser Asn Arg Tyr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Ala His Leu Pro Leu Thr Phe Gly Gln Gly Thr Lys Val Glu Ile Lys
            100                 105                 110


<210> SEQ ID NO 17
<211> LENGTH: 112
<212> TYPE: PRT
<213> ORGANISM: Artificial Sequence
<220> FEATURE:
<223> OTHER INFORMATION: isolated anti-NGF antibody VL

<400> SEQUENCE: 17

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Gln Arg
            20                  25                  30

Asn Gly Asn Thr Tyr Leu Ser Trp Tyr Gln Gln Arg Pro Gly Gln Ser
        35                  40                  45

Pro Arg Leu Leu Ile Tyr Gln Val Ser Asn Arg Tyr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Ala His Leu Pro Leu Thr Phe Gly Gln Gly Thr Lys Val Glu Ile Lys
            100                 105                 110


<210> SEQ ID NO 18
<211> LENGTH: 112
<212> TYPE: PRT
<213> ORGANISM: Artificial Sequence
<220> FEATURE:
```

<223> OTHER INFORMATION: isolated anti-NGF antibody VL

<400> SEQUENCE: 18

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Gln Arg
20 25 30

Asn Gly Asn Thr Tyr Leu Ser Trp Tyr Gln Gln Arg Pro Gly Gln Pro
35 40 45

Pro Arg Leu Leu Ile Tyr Gln Val Ser Asn Arg Tyr Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Gly Gln Gly
85 90 95

Ala His Leu Pro Leu Thr Phe Gly Gln Gly Thr Lys Val Glu Ile Lys
100 105 110

<210> SEQ ID NO 19
<211> LENGTH: 112
<212> TYPE: PRT
<213> ORGANISM: Artificial Sequence
<220> FEATURE:
<223> OTHER INFORMATION: isolated anti-NGF antibody VL

<400> SEQUENCE: 19

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Gln Arg
20 25 30

Asn Gly Asn Thr Tyr Leu Ser Trp Phe Gln Gln Arg Pro Gly Gln Pro
35 40 45

Pro Arg Leu Leu Ile Tyr Gln Val Ser Asn Arg Tyr Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Gly Gln Gly
85 90 95

Ala His Leu Pro Leu Thr Phe Gly Gln Gly Thr Lys Val Glu Ile Lys
100 105 110

<210> SEQ ID NO 20
<211> LENGTH: 112
<212> TYPE: PRT
<213> ORGANISM: Artificial Sequence
<220> FEATURE:
<223> OTHER INFORMATION: isolated anti-NGF antibody VL

<400> SEQUENCE: 20

Asp Ile Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Gln Arg
20 25 30

Asn Gly Asn Thr Tyr Leu Ser Trp Phe Gln Gln Arg Pro Gly Gln Ser
35 40 45

Pro Arg Leu Leu Ile Tyr Gln Val Ser Asn Arg Tyr Ser Gly Val Pro
50 55 60

Asp Arg Phe Ser Gly Ser Gly Ser Gly Thr Asp Phe Thr Leu Lys Ile 65 70 75 80

Ser Arg Val Glu Ala Glu Asp Val Gly Val Tyr Tyr Cys Gly Gln Gly
85 90 95

Ala His Leu Pro Leu Thr Phe Gly Gln Gly Thr Lys Val Glu Ile Lys
100 105 110

<210> SEQ ID NO 21
<211> LENGTH: 112
<212> TYPE: PRT
<213> ORGANISM: Artificial Sequence
<220> FEATURE:
<223> OTHER INFORMATION: isolated anti-NGF antibody VL

<400> SEQUENCE: 21

Asp Ile Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Gln Arg
20 25 30

Asn Gly Asn Thr Tyr Leu Ser Trp Tyr Gln Gln Arg Pro Gly Gln Ser
35 40 45

Pro Arg Leu Leu Ile Tyr Gln Val Ser Asn Arg Tyr Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Gly Gln Gly
85 90 95

Ala His Leu Pro Leu Thr Phe Gly Gln Gly Thr Lys Val Glu Ile Lys
100 105 110

<210> SEQ ID NO 22
<211> LENGTH: 112
<212> TYPE: PRT
<213> ORGANISM: Artificial Sequence
<220> FEATURE:
<223> OTHER INFORMATION: isolated anti-NGF antibody VL

<400> SEQUENCE: 22

Asp Ile Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Gln Arg
20 25 30

Asn Gly Asn Thr Tyr Leu Ser Trp Tyr Gln Gln Arg Pro Gly Gln Pro
35 40 45

Pro Arg Leu Leu Ile Tyr Gln Val Ser Asn Arg Tyr Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Gly Gln Gly
85 90 95

Ala His Leu Pro Leu Thr Phe Gly Gln Gly Thr Lys Val Glu Ile Lys
100 105 110

<210> SEQ ID NO 23
<211> LENGTH: 112
<212> TYPE: PRT
<213> ORGANISM: Artificial Sequence
<220> FEATURE:
<223> OTHER INFORMATION: isolated anti-NGF antibody VL

<400> SEQUENCE: 23

Asp Ile Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Gln Arg
20 25 30

Asn Gly Asn Thr Tyr Leu Ser Trp Phe Gln Gln Arg Pro Gly Gln Pro
35 40 45

Pro Arg Leu Leu Ile Tyr Gln Val Ser Asn Arg Tyr Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Gly Gln Gly
85 90 95

Ala His Leu Pro Leu Thr Phe Gly Gln Gly Thr Lys Val Glu Ile Lys
100 105 110

<210> SEQ ID NO 24
<211> LENGTH: 112
<212> TYPE: PRT
<213> ORGANISM: Artificial Sequence
<220> FEATURE:
<223> OTHER INFORMATION: isolated anti-NGF antibody VL

<400> SEQUENCE: 24

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Gln Arg
20 25 30

Asn Ala Asn Thr Tyr Leu Ser Trp Tyr Gln Gln Arg Pro Gly Gln Ser
35 40 45

Pro Arg Leu Leu Ile Tyr Gln Val Ser Asn Arg Tyr Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Gly Gln Gly
85 90 95

Ala His Leu Pro Leu Thr Phe Gly Gln Gly Thr Lys Val Glu Ile Lys
100 105 110

<210> SEQ ID NO 25
<211> LENGTH: 330
<212> TYPE: PRT
<213> ORGANISM: Artificial Sequence
<220> FEATURE:
<223> OTHER INFORMATION: the heavy chain constant region

<400> SEQUENCE: 25

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys

```
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 26
<211> LENGTH: 327
<212> TYPE: PRT
<213> ORGANISM: Artificial Sequence
<220> FEATURE:
<223> OTHER INFORMATION: the heavy chain constant region

<400> SEQUENCE: 26

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
```

```
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 27
<211> LENGTH: 107
<212> TYPE: PRT
<213> ORGANISM: Artificial Sequence
<220> FEATURE:
<223> OTHER INFORMATION: the light chain constant region

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 28
<211> LENGTH: 120
<212> TYPE: PRT
<213> ORGANISM: Artificial Sequence
<220> FEATURE:
<223> OTHER INFORMATION: human NGF
```

<400> SEQUENCE: 28

Ser Ser Ser His Pro Ile Phe His Arg Gly Glu Phe Ser Val Cys Asp
1 5 10 15

Ser Val Ser Val Trp Val Gly Asp Lys Thr Thr Ala Thr Asp Ile Lys
20 25 30

Gly Lys Glu Val Met Val Leu Gly Glu Val Asn Ile Asn Asn Ser Val
35 40 45

Phe Lys Gln Tyr Phe Phe Glu Thr Lys Cys Arg Asp Pro Asn Pro Val
50 55 60

Asp Ser Gly Cys Arg Gly Ile Asp Ser Lys His Trp Asn Ser Tyr Cys
65 70 75 80

Thr Thr Thr His Thr Phe Val Lys Ala Leu Thr Met Asp Gly Lys Gln
85 90 95

Ala Ala Trp Arg Phe Ile Arg Ile Asp Thr Ala Cys Val Cys Val Leu
100 105 110

Ser Arg Lys Ala Val Arg Arg Ala
115 120

<210> SEQ ID NO 29
<211> LENGTH: 118
<212> TYPE: PRT
<213> ORGANISM: Artificial Sequence
<220> FEATURE:
<223> OTHER INFORMATION: human NGF

<400> SEQUENCE: 29

Ser Ser Ser His Pro Ile Phe His Arg Gly Glu Phe Ser Val Cys Asp
1 5 10 15

Ser Val Ser Val Trp Val Gly Asp Lys Thr Thr Ala Thr Asp Ile Lys
20 25 30

Gly Lys Glu Val Met Val Leu Gly Glu Val Asn Ile Asn Asn Ser Val
35 40 45

Phe Lys Gln Tyr Phe Phe Glu Thr Lys Cys Arg Asp Pro Asn Pro Val
50 55 60

Asp Ser Gly Cys Arg Gly Ile Asp Ser Lys His Trp Asn Ser Tyr Cys
65 70 75 80

Thr Thr Thr His Thr Phe Val Lys Ala Leu Thr Met Asp Gly Lys Gln
85 90 95

Ala Ala Trp Arg Phe Ile Arg Ile Asp Thr Ala Cys Val Cys Val Leu
100 105 110

Ser Arg Lys Ala Val Arg
115

<210> SEQ ID NO 30
<211> LENGTH: 16
<212> TYPE: PRT
<213> ORGANISM: Artificial Sequence
<220> FEATURE:
<223> OTHER INFORMATION: LC-CDR1
<220> FEATURE:
<221> NAME/KEY: VARIANT
<222> LOCATION: 11
<223> OTHER INFORMATION: Xaa can be any amino acid

<400> SEQUENCE: 30

Arg Ser Ser Gln Ser Leu Val Gln Arg Asn Xaa Asn Thr Tyr Leu Ser
1 5 10 15

<210> SEQ ID NO 31
<211> LENGTH: 30
<212> TYPE: PRT
<213> ORGANISM: Artificial Sequence
<220> FEATURE:
<223> OTHER INFORMATION: anti-NGF antibody heavy chain variable region FR1
<220> FEATURE:
<221> NAME/KEY: VARIANT
<222> LOCATION: 16
<223> OTHER INFORMATION: Xaa = Glu or Ala
<220> FEATURE:
<221> NAME/KEY: VARIANT
<222> LOCATION: 17
<223> OTHER INFORMATION: Xaa = Ser or Thr
<220> FEATURE:
<221> NAME/KEY: VARIANT
<222> LOCATION: 18
<223> OTHER INFORMATION: Xaa = Val or Leu
<220> FEATURE:
<221> NAME/KEY: VARIANT
<222> LOCATION: 24
<223> OTHER INFORMATION: Xaa = Val, Gly, or Ile
<220> FEATURE:
<221> NAME/KEY: VARIANT
<222> LOCATION: 28
<223> OTHER INFORMATION: Xaa = Ser or Thr

<400> SEQUENCE: 31

Glu Val Gln Leu Val Gln Ser Gly Ala Glu Val Lys Lys Pro Gly Xaa
1 5 10 15

Xaa Xaa Lys Ile Ser Cys Lys Xaa Ser Gly Tyr Xaa Phe Ile
20 25 30

<210> SEQ ID NO 32
<211> LENGTH: 14
<212> TYPE: PRT
<213> ORGANISM: Artificial Sequence
<220> FEATURE:
<223> OTHER INFORMATION: anti-NGF antibody heavy chain variable region FR2
<220> FEATURE:
<221> NAME/KEY: VARIANT
<222> LOCATION: 3
<223> OTHER INFORMATION: Xaa = Arg or Gln
<220> FEATURE:
<221> NAME/KEY: VARIANT
<222> LOCATION: 5
<223> OTHER INFORMATION: Xaa = Met or Ala

<400> SEQUENCE: 32

Trp Val Xaa Gln Xaa Pro Gly Lys Gly Leu Glu Trp Met Gly
1 5 10

<210> SEQ ID NO 33
<211> LENGTH: 32
<212> TYPE: PRT
<213> ORGANISM: Artificial Sequence
<220> FEATURE:
<223> OTHER INFORMATION: anti-NGF antibody heavy chain variable region FR3
<220> FEATURE:
<221> NAME/KEY: VARIANT
<222> LOCATION: 1
<223> OTHER INFORMATION: Xaa = Arg or Gln
<220> FEATURE:
<221> NAME/KEY: VARIANT
<222> LOCATION: 5
<223> OTHER INFORMATION: Xaa = Thr or Ser
<220> FEATURE:
<221> NAME/KEY: VARIANT
<222> LOCATION: 8
<223> OTHER INFORMATION: Xaa = Lys or Thr
<220> FEATURE:

<221> NAME/KEY: VARIANT
<222> LOCATION: 10
<223> OTHER INFORMATION: Xaa = Ile or Thr
<220> FEATURE:
<221> NAME/KEY: VARIANT
<222> LOCATION: 11
<223> OTHER INFORMATION: Xaa = Asp or Ser
<220> FEATURE:
<221> NAME/KEY: VARIANT
<222> LOCATION: 15
<223> OTHER INFORMATION: Xaa = Leu or Met
<220> FEATURE:
<221> NAME/KEY: VARIANT
<222> LOCATION: 16
<223> OTHER INFORMATION: Xaa = Gln or Glu
<220> FEATURE:
<221> NAME/KEY: VARIANT
<222> LOCATION: 17
<223> OTHER INFORMATION: Xaa = Leu or Trp
<220> FEATURE:
<221> NAME/KEY: VARIANT
<222> LOCATION: 21
<223> OTHER INFORMATION: Xaa = Arg or Lys
<220> FEATURE:
<221> NAME/KEY: VARIANT
<222> LOCATION: 22
<223> OTHER INFORMATION: Xaa = Ala or Ser
<220> FEATURE:
<221> NAME/KEY: VARIANT
<222> LOCATION: 23
<223> OTHER INFORMATION: Xaa = Ser or Glu
<220> FEATURE:
<221> NAME/KEY: VARIANT
<222> LOCATION: 27
<223> OTHER INFORMATION: Xaa = Val or Met

<400> SEQUENCE: 33

```
Xaa Val Thr Ile Xaa Ala Asp Xaa Ser Xaa Xaa Thr Ala Tyr Xaa Xaa
1               5                   10                  15

Xaa Ser Ser Leu Xaa Xaa Xaa Asp Thr Ala Xaa Tyr Tyr Cys Ala Lys
            20                  25                  30
```

<210> SEQ ID NO 34
<211> LENGTH: 11
<212> TYPE: PRT
<213> ORGANISM: Artificial Sequence
<220> FEATURE:
<223> OTHER INFORMATION: anti-NGF antibody heavy chain variable region FR4

<400> SEQUENCE: 34

```
Trp Gly Gln Gly Thr Leu Val Thr Val Ser Ser
1               5                   10
```

<210> SEQ ID NO 35
<211> LENGTH: 23
<212> TYPE: PRT
<213> ORGANISM: Artificial Sequence
<220> FEATURE:
<223> OTHER INFORMATION: anti-NGF antibody light chain variable region FR1
<220> FEATURE:
<221> NAME/KEY: VARIANT
<222> LOCATION: 2
<223> OTHER INFORMATION: Xaa = Val or Ile
<220> FEATURE:
<221> NAME/KEY: VARIANT
<222> LOCATION: 7
<223> OTHER INFORMATION: Xaa = Thr or Ser
<220> FEATURE:
<221> NAME/KEY: VARIANT
<222> LOCATION: 11
<223> OTHER INFORMATION: Xaa = Ser or Leu

<400> SEQUENCE: 35

Asp Xaa Val Met Thr Gln Xaa Pro Leu Ser Xaa Pro Val Thr Leu Gly
1 5 10 15

Gln Pro Ala Ser Ile Ser Cys
20

<210> SEQ ID NO 36
<211> LENGTH: 15
<212> TYPE: PRT
<213> ORGANISM: Artificial Sequence
<220> FEATURE:
<223> OTHER INFORMATION: anti-NGF antibody light chain variable region FR2
<220> FEATURE:
<221> NAME/KEY: VARIANT
<222> LOCATION: 2
<223> OTHER INFORMATION: Xaa = Leu, Tyr, or Phe
<220> FEATURE:
<221> NAME/KEY: VARIANT
<222> LOCATION: 9
<223> OTHER INFORMATION: Xaa = Pro or Ser

<400> SEQUENCE: 36

Trp Xaa Gln Gln Arg Pro Gly Gln Xaa Pro Arg Leu Leu Ile Tyr
1 5 10 15

<210> SEQ ID NO 37
<211> LENGTH: 32
<212> TYPE: PRT
<213> ORGANISM: Artificial Sequence
<220> FEATURE:
<223> OTHER INFORMATION: anti-NGF antibody light chain variable region FR3
<220> FEATURE:
<221> NAME/KEY: VARIANT
<222> LOCATION: 11
<223> OTHER INFORMATION: Xaa = Ala or Ser

<400> SEQUENCE: 37

Gly Val Pro Asp Arg Phe Ser Gly Ser Gly Xaa Gly Thr Asp Phe Thr
1 5 10 15

Leu Lys Ile Ser Arg Val Glu Ala Glu Asp Val Gly Val Tyr Tyr Cys
20 25 30

<210> SEQ ID NO 38
<211> LENGTH: 10
<212> TYPE: PRT
<213> ORGANISM: Artificial Sequence
<220> FEATURE:
<223> OTHER INFORMATION: anti-NGF antibody light chain variable region FR4

<400> SEQUENCE: 38

Phe Gly Gln Gly Thr Lys Val Glu Ile Lys
1 5 10

<210> SEQ ID NO 39
<211> LENGTH: 16
<212> TYPE: PRT
<213> ORGANISM: Artificial Sequence
<220> FEATURE:
<223> OTHER INFORMATION: LC-CDR1
<220> FEATURE:
<221> NAME/KEY: VARIANT -continued

```
<222> LOCATION: 11
<223> OTHER INFORMATION: Xaa = Gly, Ala, Ser, or Thr

<400> SEQUENCE: 39

Arg Ser Ser Gln Ser Leu Val Gln Arg Asn Xaa Asn Thr Tyr Leu Ser
1               5                   10                  15
```